(12) United States Patent
Lau et al.

(10) Patent No.: US 12,702,509 B2
(45) Date of Patent: Aug. 11, 2026

(54) STERILE PACKAGING ASSEMBLY FOR ROBOTIC INTERVENTIONAL DEVICE

(71) Applicant: Imperative Care, Inc., Campbell, CA (US)

(72) Inventors: Lilip Lau, Los Altos, CA (US); Albert Harris, Livermore, CA (US)

(73) Assignee: Imperative Care, Inc., Campbell, CA (US)

( * ) Notice: Subject to any disclaimer, the term of this patent is extended or adjusted under 35 U.S.C. 154(b) by 1142 days.

(21) Appl. No.: 17/527,460

(22) Filed: Nov. 16, 2021

(65) Prior Publication Data

US 2023/0052862 A1 Feb. 16, 2023

Related U.S. Application Data

(60) Provisional application No. 63/232,444, filed on Aug. 12, 2021.

(51) Int. Cl.
*A61B 34/37* (2016.01)
*A61B 5/00* (2006.01)
(Continued)

(52) U.S. Cl.
CPC ............ *A61B 34/37* (2016.02); *A61B 5/6852* (2013.01); *A61B 17/22* (2013.01); *A61B 34/30* (2016.02);
(Continued)

(58) Field of Classification Search
CPC ....... A61B 34/37; A61B 5/6852; A61B 17/22; A61B 34/30; A61B 34/71; A61B 2017/22038; A61B 2034/301; A61B 2034/715; A61B 5/0215; A61B 5/14503; A61B 2017/00876; A61B 2090/064; A61B 50/30; A61M 25/0097; A61M 25/0127; A61M 25/09; A61M 25/002;
(Continued)

(56) References Cited

U.S. PATENT DOCUMENTS 1,286,033 A 11/1918 Lambeth
3,605,750 A 9/1971 Sheridan et al.
(Continued)

FOREIGN PATENT DOCUMENTS

AU 758458 B2 3/2003
AU 2006268156 B2 4/2012
(Continued)

OTHER PUBLICATIONS

US 12,076,032 B1, 09/2024, Teigen et al. (withdrawn)
(Continued)

*Primary Examiner* — Bhisma Mehta
*Assistant Examiner* — Haden Matthew Ritchie
(74) *Attorney, Agent, or Firm* — Knobbe, Martens, Olson & Bear, LLP

(57) ABSTRACT

A sterile packaging assembly for transporting interventional devices to a robotic surgery site includes a sterile barrier having a hub support portion and configured to enclose a sterile volume; and at least a first interventional device within the sterile volume. The first interventional device includes a hub and an elongate flexible body. The hub includes at least one magnet and at least one roller configured to roll on the hub support portion of the sterile barrier.

40 Claims, 14 Drawing Sheets

(51) Int. Cl.
*A61B 17/22* (2006.01)
*A61B 34/00* (2016.01)
*A61B 34/30* (2016.01)
*A61M 25/00* (2006.01)
*A61M 25/01* (2006.01)
*A61M 25/09* (2006.01)

(52) U.S. Cl.
CPC ......... *A61B 34/71* (2016.02); *A61M 25/0097* (2013.01); *A61M 25/0127* (2013.01); *A61M 25/09* (2013.01); *A61B 2017/22038* (2013.01); *A61B 2017/22079* (2013.01); *A61B 2034/301* (2016.02); *A61B 2034/715* (2016.02); *A61B 2562/0261* (2013.01); *A61M 25/002* (2013.01); *A61M 25/0113* (2013.01); *A61M 2205/3306* (2013.01); *A61M 2205/332* (2013.01); *A61M 2205/3331* (2013.01); *A61M 2205/3592* (2013.01); *A61M 2205/583* (2013.01)

(58) Field of Classification Search
CPC ...... A61M 25/0113; A61M 2205/3592; A61M 2205/583
See application file for complete search history.

(56) References Cited

U.S. PATENT DOCUMENTS 3,884,242 A 5/1975 Bazell et al.
3,890,976 A 6/1975 Bazell et al.
3,965,901 A 6/1976 Penny et al.
4,030,503 A 6/1977 Clark, III
4,319,580 A 3/1982 Colley et al.
4,611,594 A 9/1986 Grayhack et al.
4,617,019 A 10/1986 Fecht et al.
4,619,274 A 10/1986 Morrison
4,628,168 A 12/1986 Nebergall et al.
4,762,129 A 8/1988 Bonzel
4,762,130 A 8/1988 Fogarty et al.
4,767,399 A 8/1988 Bollish
4,810,582 A 3/1989 Gould et al.
4,819,653 A 4/1989 Marks
4,844,064 A 7/1989 Thimsen et al.
4,898,575 A 2/1990 Fischell et al.
4,923,462 A 5/1990 Stevens
4,925,444 A 5/1990 Orkin
5,011,488 A 4/1991 Ginsburg
5,037,404 A 8/1991 Gold et al.
5,040,548 A 8/1991 Yock
5,103,827 A 4/1992 Smith
5,120,323 A 6/1992 Shockey et al.
5,131,391 A 7/1992 Sakai et al.
5,217,705 A 6/1993 Reno et al.
5,226,909 A 7/1993 Evans et al.
5,234,416 A 8/1993 Macaulay et al.
5,243,997 A 9/1993 Uflacker et al.
5,261,916 A 11/1993 Engelson et al.
5,290,247 A 3/1994 Crittenden
5,308,327 A 5/1994 Heaven et al.
5,328,472 A 7/1994 Steinke et al.
5,380,268 A 1/1995 Wheeler
5,413,560 A 5/1995 Solar
5,417,697 A 5/1995 Wilk et al.
5,423,846 A 6/1995 Fischell
5,439,445 A 8/1995 Kontos
5,441,051 A 8/1995 Hileman et al.
5,454,795 A 10/1995 Samson
5,466,222 A 11/1995 Ressemann et al.
5,474,563 A 12/1995 Myler et al.
5,527,292 A 6/1996 Adams et al.
5,549,119 A 8/1996 Solar
5,569,178 A 10/1996 Henley
5,569,277 A 10/1996 Evans et al.
5,591,187 A 1/1997 Dekel
5,638,818 A 6/1997 Diab et al.
5,643,254 A 7/1997 Scheldrup et al.
5,658,263 A 8/1997 Dang et al.
5,662,622 A 9/1997 Gore et al.
5,690,613 A 11/1997 Verbeek
5,695,483 A 12/1997 Samson
5,702,373 A 12/1997 Samson
5,713,848 A 2/1998 Dubrul et al.
5,766,191 A 6/1998 Trerotola
5,776,141 A 7/1998 Klein et al.
5,792,124 A 8/1998 Horrigan et al.
5,827,242 A 10/1998 Follmer et al.
5,843,103 A 12/1998 Wulfman
5,873,882 A 2/1999 Straub et al.
5,876,414 A 3/1999 Straub
5,882,333 A 3/1999 Schaer et al.
5,885,209 A 3/1999 Green
5,891,114 A 4/1999 Chien et al.
5,895,398 A 4/1999 Wensel et al.
5,899,892 A 5/1999 Mortier et al.
5,916,192 A 6/1999 Nita et al.
5,935,112 A 8/1999 Stevens
5,951,539 A 9/1999 Nita
5,989,208 A 11/1999 Nita
6,007,530 A 12/1999 Dornhofer et al.
6,056,837 A 5/2000 Lieber et al.
6,059,745 A 5/2000 Gelbfish
6,090,118 A 7/2000 McGuckin, Jr.
6,096,004 A 8/2000 Meglan et al.
6,152,909 A 11/2000 Bagaoisan et al.
6,159,230 A 12/2000 Samuels
6,165,163 A 12/2000 Chien et al.
6,165,199 A 12/2000 Barbut
6,171,295 B1 1/2001 Garabedian et al.
6,179,859 B1 1/2001 Bates et al.
6,197,014 B1 3/2001 Samson et al.
6,206,852 B1 3/2001 Lee
6,217,557 B1 4/2001 Hakansson et al.
6,221,038 B1 4/2001 Brisken
6,228,046 B1 5/2001 Brisken
6,258,052 B1 7/2001 Milo
6,267,783 B1 7/2001 Letendre et al.
6,285,903 B1 9/2001 Rosenthal et al.
6,355,027 B1 3/2002 Le et al.
6,375,471 B1 4/2002 Wendlandt et al.
6,394,976 B1 5/2002 Winston et al.
6,400,971 B1 6/2002 Firanov et al.
6,451,005 B1 9/2002 Saitou et al.
6,451,036 B1 9/2002 Heitzmann et al.
6,458,139 B1 10/2002 Palmer et al.
6,468,219 B1 10/2002 Njemanze
6,482,217 B1 11/2002 Pintor et al.
6,511,492 B1 1/2003 Rosenbluth et al.
6,520,934 B1 2/2003 Lee et al.
6,524,303 B1 2/2003 Garibaldi et al.
6,533,751 B2 3/2003 Cragg et al.
6,554,820 B1 4/2003 Wendlandt et al.
6,554,827 B2 4/2003 Chandrasekaran et al.
6,558,377 B2 5/2003 Lee et al.
6,569,148 B2 5/2003 Bagaoisan et al.
6,579,246 B2 6/2003 Jacobsen et al.
6,582,440 B1 6/2003 Brumbach
6,591,472 B1 7/2003 Noone et al.
6,638,268 B2 10/2003 Niazi
6,663,613 B1 12/2003 Evans et al.
6,666,874 B2 12/2003 Heitzmann
6,669,670 B1 12/2003 Muni et al.
6,719,717 B1 4/2004 Johnson et al.
6,726,675 B1 4/2004 Beyar
6,776,770 B1 8/2004 Trerotola
6,821,287 B1 11/2004 Jang
6,824,550 B1 11/2004 Pintor et al.
6,824,553 B1 11/2004 Samson et al.
6,929,633 B2 8/2005 Evans et al.
6,977,068 B1 12/2005 Nair et al.
7,004,954 B1 2/2006 Voss et al.
7,008,434 B2 3/2006 Kurz et al.
7,029,482 B1 4/2006 Vargas et al.
7,037,267 B1 5/2006 Lipson et al.
7,104,979 B2 9/2006 Jansen et al.

(56) References Cited

U.S. PATENT DOCUMENTS

| | | | |
|---|---|---|---|
| 7,112,298 | B2 | 9/2006 | Kampa et al. |
| 7,172,620 | B2 | 2/2007 | Gilson |
| 7,175,653 | B2 | 2/2007 | Gaber |
| 7,192,433 | B2 | 3/2007 | Osypka et al. |
| 7,207,980 | B2 | 4/2007 | Christian et al. |
| 7,214,230 | B2 | 5/2007 | Brock et al. |
| 7,223,274 | B2 | 5/2007 | Vargas et al. |
| 7,229,461 | B2 | 6/2007 | Chin et al. |
| 7,232,452 | B2 | 6/2007 | Adams et al. |
| 7,235,088 | B2 | 6/2007 | Pintor et al. |
| 7,306,585 | B2 | 12/2007 | Ross |
| 7,309,334 | B2 | 12/2007 | von Hoffmann |
| 7,331,967 | B2 | 2/2008 | Lee et al. |
| 7,335,216 | B2 | 2/2008 | Bender et al. |
| 7,379,790 | B2 | 5/2008 | Toth et al. |
| 7,416,555 | B2 | 8/2008 | Krivoruchko |
| 7,491,210 | B2 | 2/2009 | Dubrul et al. |
| 7,507,229 | B2 | 3/2009 | Hewitt et al. |
| 7,537,568 | B2 | 5/2009 | Moehring |
| 7,556,611 | B2 | 7/2009 | Kolenbrander et al. |
| 7,558,622 | B2 | 7/2009 | Tran |
| 7,567,233 | B2 | 7/2009 | Garibaldi et al. |
| 7,601,138 | B2 | 10/2009 | Goebel et al. |
| 7,608,083 | B2 | 10/2009 | Lee et al. |
| 7,615,042 | B2 | 11/2009 | Beyar et al. |
| 7,678,100 | B2 | 3/2010 | Chin et al. |
| 7,713,227 | B2 | 5/2010 | Wholey et al. |
| 7,727,185 | B2 | 6/2010 | Weitzner |
| 7,747,960 | B2 | 6/2010 | Garibaldi et al. |
| 7,756,308 | B2 | 7/2010 | Viswanathan |
| 7,761,133 | B2 | 7/2010 | Viswanathan et al. |
| 7,763,196 | B2 | 7/2010 | Goebel et al. |
| 7,766,871 | B2 | 8/2010 | Hirszowicz et al. |
| 7,766,894 | B2 | 8/2010 | Weitzner et al. |
| 7,771,358 | B2 | 8/2010 | Moehring et al. |
| 7,789,874 | B2 | 9/2010 | Yu et al. |
| 7,803,136 | B2 | 9/2010 | Schatz |
| D626,250 | S | 10/2010 | Wenderow et al. |
| 7,818,076 | B2 | 10/2010 | Viswanathan |
| 7,831,294 | B2 | 11/2010 | Viswanathan |
| 7,837,692 | B2 | 11/2010 | Mulholland et al. |
| 7,842,055 | B2 | 11/2010 | Pintor et al. |
| 7,850,623 | B2 | 12/2010 | Griffin et al. |
| 7,850,640 | B2 | 12/2010 | Williams et al. |
| 7,850,642 | B2 | 12/2010 | Moll et al. |
| 7,853,306 | B2 | 12/2010 | Viswanathan et al. |
| 7,884,727 | B2 | 2/2011 | Tran |
| 7,886,743 | B2 | 2/2011 | Cooper et al. |
| 7,887,549 | B2 | 2/2011 | Wenderow et al. |
| 7,905,891 | B2 | 3/2011 | Self |
| 7,909,798 | B2 | 3/2011 | Osypka |
| 7,931,659 | B2 | 4/2011 | Bose et al. |
| 7,938,820 | B2 | 5/2011 | Webster et al. |
| 7,951,243 | B2 | 5/2011 | Boyle, Jr. et al. |
| 7,955,316 | B2 | 6/2011 | Weitzner et al. |
| 7,955,344 | B2 | 6/2011 | Finitsis |
| 7,955,345 | B2 | 6/2011 | Kucharczyk et al. |
| 7,963,288 | B2 | 6/2011 | Rosenberg et al. |
| 7,988,646 | B2 | 8/2011 | Taber |
| 8,004,229 | B2 | 8/2011 | Nowlin et al. |
| 8,021,326 | B2 | 9/2011 | Moll et al. |
| 8,021,351 | B2 | 9/2011 | Boldenow et al. |
| RE42,804 | E | 10/2011 | Dedig et al. |
| 8,048,032 | B2 | 11/2011 | Root et al. |
| 8,052,636 | B2 | 11/2011 | Moll et al. |
| 8,057,497 | B1 | 11/2011 | Raju et al. |
| 8,062,316 | B2 | 11/2011 | Patel et al. |
| 8,070,694 | B2 | 12/2011 | Galdonik et al. |
| 8,079,978 | B2 | 12/2011 | Hirszowicz et al. |
| 8,083,753 | B2 | 12/2011 | Solar et al. |
| 8,084,246 | B2 | 12/2011 | Hoon et al. |
| 8,108,069 | B2 | 1/2012 | Stahler et al. |
| 8,114,032 | B2 | 2/2012 | Ferry et al. |
| 8,114,106 | B2 | 2/2012 | Straub |
| 8,123,726 | B2 | 2/2012 | Searfoss et al. |
| 8,123,769 | B2 | 2/2012 | Osborne |
| 8,131,379 | B2 | 3/2012 | Hauck |
| 8,137,317 | B2 | 3/2012 | Osypka |
| 8,142,413 | B2 | 3/2012 | Root et al. |
| 8,146,874 | B2 | 4/2012 | Yu |
| 8,157,792 | B2 | 4/2012 | Dolliver et al. |
| 8,165,684 | B2 | 4/2012 | Putz et al. |
| 8,190,238 | B2 | 5/2012 | Moll et al. |
| 8,211,023 | B2 | 7/2012 | Swan et al. |
| 8,220,468 | B2 | 7/2012 | Cooper et al. |
| 8,235,968 | B2 | 8/2012 | Tremaglio |
| 8,242,972 | B2 | 8/2012 | Garibaldi et al. |
| 8,244,824 | B2 | 8/2012 | Garibaldi et al. |
| 8,246,641 | B2 | 8/2012 | Osborne et al. |
| 8,257,302 | B2 | 9/2012 | Beyar et al. |
| 8,262,671 | B2 | 9/2012 | Osypka |
| 8,281,807 | B2 | 10/2012 | Trombley et al. |
| 8,292,850 | B2 | 10/2012 | Root et al. |
| 8,298,591 | B2 | 10/2012 | Srivastava et al. |
| 8,307,693 | B2 | 11/2012 | Uram et al. |
| D674,484 | S | 1/2013 | Murphy et al. |
| 8,343,096 | B2 | 1/2013 | Kirschenman et al. |
| 8,343,098 | B2 | 1/2013 | Nystrom et al. |
| 8,361,095 | B2 | 1/2013 | Osborne |
| 8,366,735 | B2 | 2/2013 | Bose et al. |
| 8,377,077 | B2 | 2/2013 | Reis |
| 8,382,739 | B2 | 2/2013 | Walak et al. |
| 8,390,438 | B2 | 3/2013 | Olson et al. |
| 8,394,078 | B2 | 3/2013 | Torrance et al. |
| 8,399,871 | B2 | 3/2013 | Beyar et al. |
| 8,403,909 | B2 | 3/2013 | Spohn et al. |
| 8,403,912 | B2 | 3/2013 | McFerran et al. |
| D680,645 | S | 4/2013 | Murphy et al. |
| 8,409,172 | B2 | 4/2013 | Moll et al. |
| 8,419,748 | B2 | 4/2013 | Valaie |
| 8,449,566 | B2 | 5/2013 | Finitsis |
| 8,460,312 | B2 | 6/2013 | Bose et al. |
| 8,467,853 | B2 | 6/2013 | Hunter et al. |
| D685,468 | S | 7/2013 | Murphy et al. |
| 8,480,618 | B2 | 7/2013 | Wenderow et al. |
| 8,480,697 | B2 | 7/2013 | Kucharczyk et al. |
| 8,485,969 | B2 | 7/2013 | Grayzel et al. |
| 8,498,691 | B2 | 7/2013 | Moll et al. |
| 8,506,555 | B2 | 8/2013 | Morales |
| 8,517,955 | B2 | 8/2013 | Keast et al. |
| 8,521,331 | B2 | 8/2013 | Itkowitz |
| 8,529,582 | B2 | 9/2013 | Devengenzo et al. |
| 8,535,293 | B2 | 9/2013 | Faherty et al. |
| 8,540,698 | B2 | 9/2013 | Spohn et al. |
| 8,551,084 | B2 | 10/2013 | Hauck et al. |
| 8,568,432 | B2 | 10/2013 | Straub |
| 8,603,068 | B2 | 12/2013 | Weitzner et al. |
| 8,603,122 | B2 | 12/2013 | Pokorney et al. |
| 8,608,754 | B2 | 12/2013 | Wensel et al. |
| 8,608,761 | B2 | 12/2013 | Osborne et al. |
| 8,609,426 | B2 | 12/2013 | Silver |
| 8,613,730 | B2 | 12/2013 | Hieb et al. |
| 8,617,102 | B2 | 12/2013 | Moll et al. |
| 8,620,473 | B2 | 12/2013 | Diolaiti et al. |
| 8,663,259 | B2 | 3/2014 | Levine et al. |
| 8,671,817 | B1 | 3/2014 | Bogusky |
| 8,672,880 | B2 | 3/2014 | Cohen et al. |
| 8,679,150 | B1 | 3/2014 | Janardhan |
| 8,682,411 | B2 | 3/2014 | Kassab et al. |
| 8,684,953 | B2 | 4/2014 | Cabiri |
| 8,684,962 | B2 | 4/2014 | Kirschenman et al. |
| 8,684,963 | B2 | 4/2014 | Qiu et al. |
| 8,694,157 | B2 | 4/2014 | Wenderow et al. |
| 8,696,698 | B2 | 4/2014 | Chomas et al. |
| 8,702,680 | B2 | 4/2014 | Jimenez et al. |
| 8,702,724 | B2 | 4/2014 | Olsen et al. |
| 8,725,249 | B2 | 5/2014 | Bar-Yoseph et al. |
| 8,734,374 | B2 | 5/2014 | Aklog et al. |
| 8,740,840 | B2 | 6/2014 | Foley et al. |
| 8,747,358 | B2 | 6/2014 | Trombley et al. |
| 8,758,325 | B2 | 6/2014 | Webster et al. |
| 8,758,364 | B2 | 6/2014 | Eckhouse et al. |
| 8,764,779 | B2 | 7/2014 | Levine et al. |
| 8,784,441 | B2 | 7/2014 | Rosenbluth et al. |

(56) References Cited

U.S. PATENT DOCUMENTS 8,790,297 B2 7/2014 Bromander et al.
8,799,792 B2 8/2014 Garibaldi et al.
8,800,881 B2 8/2014 Biset et al.
8,801,661 B2 8/2014 Moll et al.
8,806,359 B2 8/2014 Garibaldi et al.
8,814,892 B2 8/2014 Galdonik et al.
8,827,948 B2 9/2014 Romo
8,828,021 B2 9/2014 Wenderow et al.
8,833,293 B2 9/2014 Horn
8,840,628 B2 9/2014 Green et al.
8,852,162 B2 10/2014 Williams et al.
8,852,167 B2 10/2014 Trombley et al.
8,852,184 B2 10/2014 Kucklick
8,864,792 B2 10/2014 Eckhouse et al.
8,876,726 B2 11/2014 Amit
8,876,854 B2 11/2014 Christiansen et al.
8,894,610 B2 11/2014 Macnamara et al.
8,900,257 B2 12/2014 Straub et al.
8,905,969 B2 12/2014 Nystrom et al.
8,932,320 B1 1/2015 Janardhan et al.
8,939,963 B2 1/2015 Rogers et al.
RE45,380 E 2/2015 Root et al.
8,961,491 B2 2/2015 Uber et al.
8,968,333 B2 3/2015 Yu et al.
8,968,383 B1 3/2015 Johnson et al.
8,974,408 B2 3/2015 Wallace et al.
8,974,411 B2 3/2015 Mckinnon
8,974,420 B2 3/2015 Searfoss et al.
8,979,871 B2 3/2015 Tye
8,986,246 B2 3/2015 Foley et al.
8,992,506 B2 3/2015 Gulachenski
8,996,095 B2 3/2015 Anderson et al.
8,998,946 B2 4/2015 Morero
9,005,237 B2 4/2015 Eckhouse et al.
9,005,271 B2 4/2015 Ivancev
9,014,786 B2 4/2015 Carmeli et al.
9,017,309 B2 4/2015 Tanikawa et al.
9,023,070 B2 5/2015 Levine et al.
9,034,008 B2 5/2015 Eckhouse et al.
9,039,715 B2 5/2015 Diamant et al.
9,056,200 B2 6/2015 Uber et al.
9,066,740 B2 6/2015 Carlson et al.
9,070,486 B2 6/2015 Guerrera et al.
9,079,000 B2 7/2015 Hanson et al.
9,095,681 B2 8/2015 Wenderow et al.
9,101,379 B2 8/2015 Au et al.
9,107,691 B2 8/2015 Fojtik
9,111,016 B2 8/2015 Besson et al.
9,119,625 B2 9/2015 Bachman et al.
9,119,656 B2 9/2015 Bose et al.
9,132,949 B2 9/2015 Bidet et al.
9,138,307 B2 9/2015 Valaie
9,138,566 B2 9/2015 Cabiri
9,144,383 B2 9/2015 Zharov
9,144,662 B2 9/2015 DiCaprio et al.
RE45,760 E 10/2015 Root et al.
RE45,776 E 10/2015 Root et al.
9,168,356 B2 10/2015 Wenderow et al.
9,186,046 B2 11/2015 Ramamurthy et al.
9,199,033 B1 12/2015 Cowan et al.
9,199,064 B2 12/2015 Morero
9,205,227 B2 12/2015 Cohen et al.
9,206,309 B2 12/2015 Appleby
9,211,396 B2 12/2015 Aboytes
9,220,568 B2 12/2015 Bromander et al.
9,233,225 B2 1/2016 Hebert
9,238,124 B2 1/2016 Grayzel et al.
9,241,699 B1 1/2016 Kume et al.
9,241,768 B2 1/2016 Sandhu et al.
9,242,252 B2 1/2016 Eberle et al.
9,259,215 B2 2/2016 Chou et al.
9,259,228 B2 2/2016 Cruise et al.
9,259,526 B2 2/2016 Barron et al.
9,265,512 B2 2/2016 Garrison et al.
9,278,201 B2 3/2016 Rapaport et al.
9,282,992 B2 3/2016 Levine et al.
9,295,527 B2 3/2016 Kirschenman et al.
9,295,817 B2 3/2016 Chang
9,314,268 B2 4/2016 Cahill
9,314,306 B2 4/2016 Yu
9,314,307 B2 4/2016 Richmond et al.
9,314,310 B2 4/2016 Kirschenman et al.
9,314,311 B2 4/2016 Wenderow et al.
9,314,594 B2 4/2016 Kirschenman
9,315,663 B2 4/2016 Appleby
9,320,479 B2 4/2016 Wenderow et al.
9,320,573 B2 4/2016 Sandhu et al.
9,333,324 B2 5/2016 Cohen et al.
9,339,282 B2 5/2016 Green et al.
9,345,508 B2 5/2016 Hendrick
9,345,856 B2 5/2016 Witte
9,345,859 B2 5/2016 Blacker
9,351,735 B2 5/2016 Nagano et al.
9,351,993 B2 5/2016 Cruise et al.
9,370,639 B2 6/2016 Plassman et al.
9,375,223 B2 6/2016 Wallace
9,375,729 B2 6/2016 Eberle et al.
9,381,278 B2 7/2016 Constant et al.
9,398,946 B2 7/2016 Valaie
9,399,118 B2 7/2016 Kume et al.
RE46,116 E 8/2016 Root et al.
9,402,977 B2 8/2016 Wenderow et al.
9,408,669 B2 8/2016 Kokish et al.
9,408,916 B2 8/2016 Cruise et al.
9,414,819 B2 8/2016 Fitz et al.
9,421,328 B2 8/2016 Brueckner et al.
9,427,515 B1 8/2016 Nystrom
9,427,562 B2 8/2016 Blacker
9,439,736 B2 9/2016 Olson
9,439,791 B2 9/2016 Vong et al.
9,440,018 B2 9/2016 Levin et al.
9,446,216 B2 9/2016 Olesky et al.
9,447,890 B2 9/2016 Jennings et al.
9,451,884 B2 9/2016 Palovich et al.
9,451,963 B2 9/2016 Cruise et al.
9,452,276 B2 9/2016 Duindam et al.
9,452,277 B2 9/2016 Blacker
9,463,006 B2 10/2016 Forde et al.
9,474,857 B2 10/2016 Riley et al.
9,480,797 B1 11/2016 Swantner et al.
9,480,813 B2 11/2016 Fukuoka et al.
9,486,221 B2 11/2016 Cruise et al.
9,488,971 B2 11/2016 Yip et al.
9,492,637 B2 11/2016 Garrison et al.
9,498,291 B2 11/2016 Gilbert et al.
9,504,476 B2 11/2016 Gulachenski
9,510,855 B2 12/2016 Rapaport et al.
9,510,912 B2 12/2016 Bencteux et al.
9,517,305 B2 12/2016 Uram et al.
9,526,504 B2 12/2016 Chang
9,526,505 B2 12/2016 Marks et al.
9,532,792 B2 1/2017 Galdonik et al.
9,532,840 B2 1/2017 Wong et al.
9,533,121 B2 1/2017 Pacheco et al.
9,533,344 B2 1/2017 Monetti et al.
9,539,022 B2 1/2017 Bowman
9,539,122 B2 1/2017 Burke et al.
9,545,497 B2 1/2017 Wenderow et al.
9,546,236 B2 1/2017 Cruise et al.
9,549,783 B2 1/2017 Zirps
9,561,121 B2 2/2017 Sudin et al.
9,561,125 B2 2/2017 Bowman et al.
9,561,345 B2 2/2017 Garrison et al.
9,566,201 B2 2/2017 Yu
9,566,414 B2 2/2017 Wong et al.
9,572,481 B2 2/2017 Duindam et al.
9,585,806 B2 3/2017 Herrig
9,586,029 B2 3/2017 Shekalim et al.
9,597,101 B2 3/2017 Galdonik et al.
9,597,212 B2 3/2017 Thompson et al.
9,603,573 B2 3/2017 Leininger et al.
9,615,832 B2 4/2017 Bose et al.
9,622,753 B2 4/2017 Cox
9,623,209 B2 4/2017 Wenderow et al.

(56) References Cited

U.S. PATENT DOCUMENTS 9,623,228 B2 4/2017 Ryan et al.
9,629,595 B2 4/2017 Walker et al.
9,636,479 B2 5/2017 Bencteux et al.
9,655,633 B2 5/2017 Leynov et al.
9,655,755 B2 5/2017 Chou et al.
9,655,989 B2 5/2017 Cruise et al.
9,662,118 B2 5/2017 Chang
9,662,129 B2 5/2017 Galdonik et al.
9,662,480 B2 5/2017 Kume et al.
9,669,183 B2 6/2017 Chang
9,669,191 B2 6/2017 Chou et al.
9,681,882 B2 6/2017 Garrison et al.
9,687,304 B2 6/2017 Bencteux et al.
9,688,788 B2 6/2017 Plotkin et al.
9,693,789 B2 7/2017 Garrison et al.
9,693,852 B2 7/2017 Lam et al.
9,700,698 B2 7/2017 Pacheco et al.
9,707,377 B2 7/2017 Cohen et al.
9,707,380 B2 7/2017 Qiu et al.
9,717,500 B2 8/2017 Tieu et al.
9,717,552 B2 8/2017 Cosman
9,724,103 B2 8/2017 Cruise et al.
9,724,491 B2 8/2017 Solar et al.
9,744,305 B2 8/2017 Cowan et al.
9,750,576 B2 9/2017 Murphy et al.
9,750,953 B2 9/2017 Kalafut
9,764,111 B2 9/2017 Gulachenski
9,764,114 B2 9/2017 Murphy et al.
9,770,251 B2 9/2017 Bowman et al.
9,770,301 B2 9/2017 Bencteux et al.
9,775,730 B1 10/2017 Waltzman
9,782,130 B2 10/2017 Hauck et al.
9,782,564 B2 10/2017 Zirps et al.
9,789,242 B2 10/2017 Criado et al.
9,789,283 B2 10/2017 Richter et al.
9,789,285 B1 10/2017 Blacker
9,801,643 B2 10/2017 Hansen et al.
9,803,043 B2 10/2017 Cruise et al.
9,808,610 B2 11/2017 Li et al.
9,814,534 B2 11/2017 Wenderow et al.
9,820,761 B2 11/2017 Garrison et al.
9,825,455 B2 11/2017 Sandhu et al.
9,827,047 B2 11/2017 Fudaba et al.
9,827,410 B2 11/2017 Cowan et al.
9,828,157 B2 11/2017 Roesler
9,833,293 B2 12/2017 Wenderow et al.
9,839,481 B2 12/2017 Blumenkranz et al.
9,855,072 B2 1/2018 Moberg et al.
9,855,101 B2 1/2018 Wenderow et al.
9,861,783 B2 1/2018 Garrison et al.
9,877,731 B2 1/2018 Cruise et al.
9,877,742 B2 1/2018 Milner et al.
9,883,885 B2 2/2018 Hendrick et al.
9,907,880 B2 3/2018 Cruise et al.
9,913,960 B2 3/2018 Blanchard et al.
9,931,129 B2 4/2018 Walish et al.
9,943,321 B2 4/2018 Nita
9,943,958 B2 4/2018 Blacker et al.
9,949,799 B2 4/2018 Hingwe et al.
9,962,229 B2 5/2018 Blacker et al.
9,981,109 B2 5/2018 Blacker et al.
9,987,027 B2 6/2018 Ben-Ami
9,987,028 B2 6/2018 Lowinger et al.
9,993,614 B2 6/2018 Pacheco et al.
9,993,615 B2 6/2018 Blacker
9,999,355 B2 6/2018 Kirenko
9,999,751 B2 6/2018 Pacheco et al.
10,010,698 B2 7/2018 Watanabe et al.
10,010,699 B2 7/2018 Cohen et al.
10,028,854 B2 7/2018 Tatalovich et al.
10,029,072 B2 7/2018 Hebert
10,039,906 B2 8/2018 Kume et al.
10,046,140 B2 8/2018 Kokish et al.
10,052,761 B2 8/2018 Langenfeld et al.
10,070,878 B2 9/2018 Ma
10,071,224 B2 9/2018 Hebert
10,071,225 B2 9/2018 Hebert
10,085,805 B1 10/2018 Blacker
10,086,167 B2 10/2018 Hebert
10,086,169 B2 10/2018 Grayzel et al.
10,105,154 B1 10/2018 Green
10,105,486 B2 10/2018 Trombley et al.
10,111,703 B2 10/2018 Cosman, Jr
10,123,843 B2 11/2018 Wong et al.
10,123,844 B2 11/2018 Nowlin et al.
10,124,149 B2 11/2018 Hebert
10,130,427 B2 11/2018 Tanner et al.
10,138,025 B2 11/2018 Nakamura
10,145,747 B1 12/2018 Lin et al.
10,149,698 B2 12/2018 Wulfman et al.
10,178,995 B2 1/2019 Cragg
10,179,224 B2 1/2019 Yang et al.
10,183,145 B2 1/2019 Yang et al.
10,183,146 B2 1/2019 Yang et al.
10,183,147 B2 1/2019 Yang et al.
10,201,314 B2 2/2019 Frederick et al.
10,207,077 B2 2/2019 Griggin et al.
10,207,315 B2 2/2019 Appleby
10,213,582 B2 2/2019 Garrison et al.
10,226,277 B2 3/2019 Smith et al.
10,231,788 B2 3/2019 Olson et al.
10,238,456 B2 3/2019 Murphy et al.
10,238,833 B2 3/2019 Christian et al.
10,245,112 B2 4/2019 Kottenstette et al.
10,258,285 B2 4/2019 Hauck et al.
10,258,452 B2 4/2019 Eckhouse et al.
10,265,086 B2 4/2019 Vale
10,271,864 B2 4/2019 Greenhalgh et al.
10,271,910 B2 4/2019 Wenderow et al.
RE47,376 E 5/2019 Pokorney et al.
10,278,678 B2 5/2019 Peliks
10,278,816 B2 5/2019 Miller
10,299,867 B2 5/2019 Wenderow et al.
10,300,256 B2 5/2019 Aboytes
10,307,061 B2 6/2019 Cohen
10,307,570 B2 6/2019 Blacker
10,322,277 B2 6/2019 Nystrom
10,327,790 B2 6/2019 Garrison et al.
10,335,186 B2 7/2019 Rosenbluth et al.
10,342,570 B2 7/2019 Richter et al.
10,342,606 B2 7/2019 Cosman
10,342,953 B2 7/2019 Wenderow et al.
10,363,062 B2 7/2019 Spencer et al.
10,363,109 B2 7/2019 Dachs et al.
10,368,951 B2 8/2019 Moll et al.
10,383,691 B2 8/2019 Hendrick et al.
10,383,751 B2 8/2019 Ferrera et al.
10,384,034 B2 8/2019 Garrison et al.
10,391,234 B2 8/2019 Sams et al.
10,420,537 B2 9/2019 Salahieh et al.
10,420,581 B2 9/2019 Hehrlein
10,426,557 B2 10/2019 Amiri et al.
10,426,559 B2 10/2019 Graetzel et al.
10,426,926 B2 10/2019 Blacker et al.
10,441,745 B2 10/2019 Yang et al.
10,449,007 B2 10/2019 Deboeuf et al.
10,456,552 B2 10/2019 Goyal
10,456,556 B2 10/2019 Cabiri
10,471,233 B2 11/2019 Garrison et al.
10,512,514 B2 12/2019 Nowlin et al.
10,522,250 B2 12/2019 Spohn et al.
10,524,814 B2 1/2020 Chang et al.
10,531,883 B1 1/2020 Deville et al.
10,531,929 B2 1/2020 Widenhouse et al.
10,537,400 B2 1/2020 Dachs et al.
10,537,706 B2 1/2020 Kanemasa et al.
10,539,478 B2 1/2020 Lin et al.
10,549,071 B2 2/2020 Falb et al.
10,549,084 B2 2/2020 Sokolov et al.
10,555,780 B2 2/2020 Tanner et al.
10,556,092 B2 2/2020 Yu et al.
10,561,821 B2 2/2020 Wenderow et al.
10,568,539 B2 2/2020 Kowshik et al.
10,568,700 B2 2/2020 Donhowe et al.

(56) References Cited

U.S. PATENT DOCUMENTS 10,569,049 B2 2/2020 Garrison et al.
10,583,276 B2 3/2020 Zirps
10,588,656 B2 3/2020 Trosper et al.
10,589,018 B2 3/2020 Uber et al.
D881,234 S 4/2020 Capela
10,610,256 B2 4/2020 Bowman
10,610,668 B2 4/2020 Burkholz et al.
10,611,391 B1 4/2020 Klem et al.
10,639,098 B2 5/2020 Cosman
10,646,239 B2 5/2020 Garrison et al.
10,647,007 B2 5/2020 Cordoba et al.
10,653,426 B2 5/2020 Yang et al.
10,653,434 B1 5/2020 Yang et al.
10,653,863 B1 5/2020 Blacker et al.
10,660,814 B2 5/2020 Soundararajan et al.
10,661,053 B2 5/2020 Yang et al.
10,661,453 B2 5/2020 Koenig et al.
10,668,192 B2 6/2020 Raney et al.
10,687,903 B2 6/2020 Lewis et al.
10,695,140 B2 6/2020 Overmyer et al.
10,695,159 B2 6/2020 Hauser
10,695,533 B2 6/2020 Deboeuf et al.
10,695,536 B2 6/2020 Weitzner et al.
10,709,510 B2 7/2020 Kottenstette
10,709,512 B2 7/2020 Bajo et al.
10,716,726 B2 7/2020 Bergman et al.
10,716,880 B2 7/2020 Culbert et al.
10,716,915 B2 7/2020 Ogle et al.
10,722,251 B2 7/2020 Garrison et al.
10,722,253 B2 7/2020 Deville et al.
10,722,683 B2 7/2020 Solar et al.
10,729,825 B2 8/2020 Boyle, Jr. et al.
10,736,706 B2 8/2020 Scheib
10,737,061 B2 8/2020 Parmar
10,743,893 B2 8/2020 Garrison et al.
10,744,302 B2 8/2020 Pacheco et al.
10,751,073 B2 8/2020 Eckhouse et al.
10,765,303 B2 9/2020 Graetzel et al.
10,765,486 B2 9/2020 Bajo et al.
10,772,647 B2 9/2020 Ben-Ami
10,779,775 B2 9/2020 Bergman et al.
10,779,895 B2 9/2020 Wenderow et al.
10,783,993 B2 9/2020 Spohn et al.
10,786,268 B2 9/2020 Ben-Ami
10,786,270 B2 9/2020 Yang et al.
10,792,056 B2 10/2020 Vale et al.
10,799,305 B2 10/2020 Murphy et al.
10,806,905 B2 10/2020 Asmus
10,813,713 B2 10/2020 Koch et al.
10,814,102 B2 10/2020 Laby et al.
10,820,951 B2 11/2020 Soundararajan et al.
10,820,954 B2 11/2020 Marsot et al.
10,827,913 B2 11/2020 Ummalaneni et al.
10,828,463 B2 11/2020 Blacker
10,835,153 B2 11/2020 Rafii-Tari et al.
10,835,272 B2 11/2020 Yang et al.
10,835,278 B2 11/2020 Wilke et al.
10,835,329 B2 11/2020 Wenderow et al.
10,835,668 B2 11/2020 Novickoff et al.
10,835,711 B2 11/2020 Yang et al.
10,849,702 B2 12/2020 Hsu et al.
10,856,898 B2 12/2020 Matsushita et al.
10,864,629 B2 12/2020 Guerrera et al.
10,874,468 B2 12/2020 Wallace et al.
10,881,472 B2 1/2021 Sen et al.
10,881,474 B2 1/2021 Blacker et al.
10,881,765 B2 1/2021 Igarashi
10,888,280 B2 1/2021 Newberry
10,898,082 B2 1/2021 Sandgaard
10,898,288 B2 1/2021 Dachs, II et al.
10,900,771 B2 1/2021 Kottenstette et al.
10,905,850 B2 2/2021 Christian et al.
10,912,624 B2 2/2021 Prentakis et al.
10,912,924 B2 2/2021 Park et al.
10,945,904 B2 3/2021 de Jesus Ruiz et al.
10,953,206 B2 3/2021 Blacker
10,959,789 B2 3/2021 Yi et al.
10,959,792 B1 3/2021 Huang et al.
10,987,179 B2 4/2021 Ummalaneni et al.
10,987,491 B2 4/2021 Wenderow et al.
10,994,102 B2 5/2021 Blacker
11,007,118 B2 5/2021 Cowan et al.
11,007,348 B2 5/2021 Blacker
11,020,030 B2 6/2021 Tao et al.
11,020,059 B2 6/2021 Sheth et al.
11,040,147 B2 6/2021 Wagner
11,045,274 B2 6/2021 Dachs, II et al.
11,052,226 B2 7/2021 Salahieh et al.
11,058,508 B2 7/2021 Scheib et al.
11,065,018 B2 7/2021 Buck et al.
11,076,876 B2 8/2021 Vale
11,076,924 B2 8/2021 Kim et al.
11,078,945 B2 8/2021 Grout et al.
11,083,842 B2 8/2021 Chassot
11,083,873 B2 8/2021 Hebert
11,083,882 B2 8/2021 Schrauder et al.
11,096,712 B2 8/2021 Teigen et al.
11,104,012 B2 8/2021 Cordoba et al.
11,109,919 B2 9/2021 Murphy et al.
11,109,920 B2 9/2021 Al-Jadda et al.
11,109,921 B2 9/2021 Kottenstette et al.
11,110,217 B2 9/2021 O'Brien et al.
11,114,918 B2 9/2021 Zirps
11,123,090 B2 9/2021 Yang et al.
11,129,602 B2 9/2021 Wong et al.
11,134,859 B2 10/2021 Strasser
11,141,566 B2 10/2021 Cabiri
11,147,949 B2 10/2021 Yang et al.
11,147,950 B2 10/2021 Destrebecq et al.
11,179,213 B2 11/2021 Huang et al.
11,179,546 B2 11/2021 Martin
11,185,455 B2 11/2021 Cagle et al.
11,191,893 B2 12/2021 Capone et al.
11,197,683 B1 12/2021 Teigen et al.
11,197,771 B2 12/2021 Ferrera et al.
11,207,096 B2 12/2021 To et al.
11,207,147 B2 12/2021 Diamond et al.
11,207,497 B1 12/2021 Yee et al.
11,209,300 B2 12/2021 Johnson
11,213,356 B2 1/2022 Tanner et al.
11,213,362 B2 1/2022 Sharon et al.
11,213,654 B2 1/2022 Murphy et al.
11,224,457 B2 1/2022 Brinkmann et al.
11,234,779 B2 2/2022 Fuerst et al.
11,234,781 B2 2/2022 Penny et al.
11,234,784 B2 2/2022 Alden
11,241,291 B2 2/2022 Sharon et al.
11,253,292 B2 2/2022 Mcguckin, Jr et al.
11,259,881 B2 3/2022 Garcia Kilroy et al.
11,266,424 B2 3/2022 Hofmann et al.
11,291,515 B2 4/2022 Sharon et al.
11,298,198 B2 4/2022 Fournier et al.
11,304,668 B2 4/2022 Wenderow et al.
11,318,618 B2 5/2022 Desai
11,331,157 B2 5/2022 Russell et al.
11,337,712 B2 5/2022 Teigen et al.
11,337,764 B2 5/2022 Deboeuf et al.
11,357,586 B2 6/2022 Huang et al.
11,357,597 B2 6/2022 Jhaveri et al.
11,359,156 B2 6/2022 Long et al.
11,376,086 B2 7/2022 McGrogan et al.
11,389,360 B2 7/2022 Koenig et al.
11,400,214 B2 8/2022 Porter
11,406,402 B2 8/2022 Deville et al.
11,413,101 B2 8/2022 Sen et al.
11,413,431 B2 8/2022 Blacker
11,419,977 B2 8/2022 Cowan et al.
11,426,246 B2 8/2022 Asadian et al.
11,432,835 B2 9/2022 Shaffer et al.
11,432,840 B2 9/2022 Grothe et al.
11,448,327 B2 9/2022 Heffner et al.
11,464,587 B2 10/2022 Yu et al.
11,472,030 B2 10/2022 Ho et al.
11,478,329 B2 10/2022 Gee et al.

(56) References Cited

U.S. PATENT DOCUMENTS 11,490,911 B2 11/2022 Panian
11,491,313 B2 11/2022 Fischel
11,497,481 B2 11/2022 Penny et al.
11,497,523 B2 11/2022 Trosper et al.
11,497,568 B2 11/2022 Ho et al.
11,510,736 B2 11/2022 Rafii-Tari et al.
D976,399 S 1/2023 Carmi
11,547,426 B2 1/2023 Deville et al.
11,547,511 B2 1/2023 Asadian et al.
11,564,649 B2 1/2023 Kedmi-Shahar et al.
11,571,267 B2 2/2023 Gonenc et al.
11,576,743 B2 2/2023 Venkataraman et al.
11,577,382 B2 2/2023 Cagle et al.
11,589,931 B2 2/2023 Desai et al.
11,607,108 B2 3/2023 Yu et al.
11,628,024 B2 4/2023 Kapadia
11,633,247 B2 4/2023 Johnson et al.
11,642,181 B2 5/2023 Nobles et al.
11,653,905 B2 5/2023 Wong et al.
11,660,151 B2 5/2023 Schena
11,660,437 B2 5/2023 Verma
11,672,602 B2 6/2023 Monteverde et al.
11,678,943 B2 6/2023 Zhou et al.
11,678,948 B2 6/2023 Vargas et al.
11,684,759 B2 6/2023 Hayzelden
11,690,985 B2 7/2023 Calhoun et al.
11,696,808 B2 7/2023 Blacker et al.
11,696,810 B2 7/2023 Asadian et al.
11,701,196 B2 7/2023 Scheib et al.
11,703,604 B2 7/2023 Dissertori et al.
11,712,805 B2 8/2023 Zhou et al.
11,713,376 B2 8/2023 Leroux et al.
11,717,356 B2 8/2023 Amiri et al.
11,717,640 B2 8/2023 Fantuzzi et al.
11,723,739 B2 8/2023 Asadian et al.
11,723,744 B2 8/2023 Ergueta Tejerina et al.
11,737,821 B2 8/2023 Algawi et al.
11,744,989 B2 9/2023 Blacker
11,759,269 B2 9/2023 Zhou et al.
11,764,873 B2 9/2023 Burla et al.
11,766,786 B2 9/2023 Cordoba et al.
11,780,092 B2 10/2023 Desai et al.
11,785,938 B2 10/2023 Clavien et al.
11,786,329 B2 10/2023 Fuerst et al.
11,793,500 B2 10/2023 Vargas
11,793,597 B2 10/2023 Vargas et al.
11,801,365 B2 10/2023 Blacker et al.
11,813,203 B2 11/2023 Timm et al.
11,819,295 B2 11/2023 Wenderow et al.
11,832,904 B2 12/2023 Wenderow et al.
11,844,580 B2 12/2023 Sen et al.
11,844,732 B2 12/2023 Klem et al.
11,883,119 B2 1/2024 Sen et al.
11,883,245 B2 1/2024 Fathollahi Ghezelghieh et al.
11,890,024 B2 2/2024 Panian
11,890,432 B2 2/2024 Awad et al.
11,896,325 B2 2/2024 Clark et al.
11,903,669 B2 2/2024 Cope et al.
11,906,009 B2 2/2024 Klem
11,911,120 B2 2/2024 Freiin Von Kapri et al.
11,911,910 B2 2/2024 Gonenc et al.
11,918,240 B2 3/2024 Deville et al.
11,918,312 B2 3/2024 Yu
11,918,423 B2 3/2024 Kottenstette et al.
11,931,901 B2 3/2024 Murphy et al.
11,998,290 B2 6/2024 Murphy et al.
12,004,829 B2 6/2024 Searfoss et al.
12,005,589 B2 6/2024 Rea et al.
12,035,989 B2 7/2024 Clark et al.
12,046,363 B2 7/2024 Shrivastava et al.
12,059,161 B2 8/2024 Deville et al.
12,059,225 B2 8/2024 Zhou et al.
12,076,036 B2 9/2024 Baron et al.
12,076,099 B2 9/2024 Shrivastava et al.
12,076,497 B2 9/2024 Fantuzzi et al.
12,076,505 B2 9/2024 Haubert
12,082,982 B2 9/2024 Jhaveri et al.
12,087,024 B2 9/2024 Djelouah et al.
12,102,290 B2 10/2024 Sharon et al.
12,114,940 B2 10/2024 Garcia Kilroy et al.
12,117,624 B2 10/2024 Fuerst et al.
12,133,700 B2 11/2024 Miller et al.
12,133,702 B2 11/2024 Nowlin et al.
12,133,965 B2 11/2024 Chassot et al.
12,137,990 B2 11/2024 Walker et al.
12,138,004 B2 11/2024 Cone et al.
12,138,130 B2 11/2024 Garbus et al.
12,144,564 B2 11/2024 Barbagli et al.
12,144,569 B2 11/2024 Cone et al.
12,144,575 B2 11/2024 Torabi
12,150,660 B1 11/2024 Teigen et al.
12,150,796 B2 11/2024 Wenderow et al.
12,156,666 B2 12/2024 Trosper et al.
12,156,667 B2 12/2024 Trosper et al.
12,156,711 B2 12/2024 Liao et al.
12,157,238 B2 12/2024 Fredrickson et al.
12,161,419 B2 12/2024 Fuerst et al.
12,171,505 B2 12/2024 Barbagli et al.
12,171,543 B2 12/2024 Duindam et al.
12,177,411 B2 12/2024 Culman
12,178,387 B2 12/2024 McDowall et al.
12,178,399 B2 12/2024 Itkowitz et al.
12,178,526 B2 12/2024 McKenney et al.
12,178,534 B2 12/2024 Asadian et al.
12,185,947 B2 1/2025 Hart
12,191,031 B2 1/2025 Azizian et al.
12,201,484 B2 1/2025 Itkowitz et al.
12,201,485 B2 1/2025 McDowall et al.
12,212,240 B2 1/2025 Schulz
12,329,397 B2 6/2025 Bartholomew
12,350,415 B2 7/2025 Kumar et al.
12,383,668 B2 8/2025 Batarilo et al.
12,397,099 B2 8/2025 Aaron et al.
12,419,501 B2 9/2025 Canale et al.
D1,102,447 S 11/2025 Bartholomew et al.
2001/0031980 A1 10/2001 Wensel et al.
2001/0031981 A1 10/2001 Evans et al.
2001/0049486 A1 12/2001 Evans et al.
2002/0016565 A1 2/2002 Zadno-Azizi et al.
2002/0026145 A1 2/2002 Bagaoisan et al.
2002/0074276 A1 6/2002 Nakashima
2002/0091372 A1 7/2002 Cragg et al.
2002/0113501 A1 8/2002 Doi
2002/0156459 A1 10/2002 Ye et al.
2002/0156460 A1 10/2002 Ye et al.
2002/0169467 A1 11/2002 Heitzmann et al.
2002/0173812 A1 11/2002 McGuckin et al.
2002/0177899 A1 11/2002 Eum et al.
2002/0188314 A1 12/2002 Anderson et al.
2002/0192113 A1 12/2002 Uffenheimer et al.
2003/0071285 A1 4/2003 Tsukernik
2003/0088266 A1 5/2003 Bowlin
2003/0100849 A1 5/2003 Jang
2003/0105451 A1 6/2003 Westlund et al.
2003/0114739 A1 6/2003 Fuimaono et al.
2003/0125673 A1 7/2003 Houde et al.
2003/0135193 A1 7/2003 Hilgers et al.
2003/0135198 A1 7/2003 Berhow et al.
2003/0153847 A1 8/2003 Sandler et al.
2003/0153874 A1 8/2003 Tal
2003/0195467 A1 10/2003 Mickley
2003/0195546 A1 10/2003 Solar et al.
2003/0225336 A1 12/2003 Callister et al.
2004/0010280 A1 1/2004 Adams et al.
2004/0059290 A1 3/2004 Palasis
2004/0068248 A1 4/2004 Mooney et al.
2004/0097805 A1 5/2004 Verard et al.
2004/0138693 A1 7/2004 Eskuri et al.
2004/0143225 A1 7/2004 Callan
2004/0153049 A1 8/2004 Hewitt et al.
2004/0199201 A1 10/2004 Kellett et al.
2004/0215222 A1 10/2004 Krivoruchko
2004/0236215 A1 11/2004 Mihara et al.
2004/0243102 A1 12/2004 Berg et al.

(56) References Cited

U.S. PATENT DOCUMENTS

2005/0004523 A1 1/2005 Osborne et al.
2005/0004553 A1 1/2005 Douk
2005/0021002 A1 1/2005 Deckman et al.
2005/0055047 A1 3/2005 Greenhalgh
2005/0059957 A1 3/2005 Campbell et al.
2005/0077225 A1 4/2005 Usher et al.
2005/0080400 A1 4/2005 Corcoran et al.
2005/0103332 A1 5/2005 Gingles et al.
2005/0107667 A1 5/2005 Danitz
2005/0124985 A1 6/2005 Takayama et al.
2005/0137680 A1 6/2005 Ortiz et al.
2005/0165276 A1 7/2005 Belson et al.
2005/0182386 A1 8/2005 Aggerholm
2005/0187570 A1 8/2005 Nguyen et al.
2005/0228417 A1 10/2005 Teitelbaum
2005/0277912 A1 12/2005 John
2006/0011501 A1 1/2006 Itou et al.
2006/0020285 A1 1/2006 Niermann
2006/0020286 A1 1/2006 Niermann
2006/0030835 A1 2/2006 Sherman et al.
2006/0064036 A1 3/2006 Osborne et al.
2006/0074401 A1 4/2006 Ross
2006/0089618 A1 4/2006 McFerran et al.
2006/0095022 A1 5/2006 Moll et al.
2006/0095062 A1 5/2006 Stephens
2006/0100530 A1 5/2006 Kliot et al.
2006/0111649 A1 5/2006 Zhou
2006/0124212 A1 6/2006 Zhou
2006/0146010 A1 7/2006 Schneider
2006/0149355 A1 7/2006 Mitelberg et al.
2006/0200026 A1 9/2006 Wallace et al.
2006/0200191 A1 9/2006 Zadno-Azizi
2006/0217664 A1 9/2006 Hattler et al.
2006/0247755 A1 11/2006 Pal et al.
2006/0264759 A1 11/2006 Moehring et al.
2007/0016132 A1 1/2007 Oepen et al.
2007/0038225 A1 2/2007 Osborne et al.
2007/0043333 A1 2/2007 Kampa et al.
2007/0060879 A1 3/2007 Weitzner
2007/0060888 A1 3/2007 Goff et al.
2007/0060915 A1 3/2007 Kucklick
2007/0106208 A1 5/2007 Uber et al.
2007/0142824 A1 6/2007 Devengenzo
2007/0179473 A1 8/2007 Masters et al.
2007/0185521 A1 8/2007 Bui et al.
2007/0197956 A1 8/2007 Le et al.
2007/0225614 A1 9/2007 Naghavi et al.
2007/0239182 A1 10/2007 Glines et al.
2007/0270639 A1 11/2007 Long
2008/0027464 A1 1/2008 Moll et al.
2008/0045881 A1 2/2008 Teitelbaum et al.
2008/0064984 A1 3/2008 Pflueger et al.
2008/0086051 A1 4/2008 Voegele
2008/0086110 A1 4/2008 Galdonik et al.
2008/0097251 A1 4/2008 Babaev et al.
2008/0188928 A1 8/2008 Salahieh et al.
2008/0234631 A1 9/2008 Reis
2008/0234715 A1 9/2008 Pesce
2008/0255505 A1 10/2008 Carlson et al.
2008/0262350 A1 10/2008 Unger
2008/0262513 A1 10/2008 Stahler et al.
2008/0294058 A1 11/2008 Shklarski
2008/0300544 A1 12/2008 Palm et al.
2008/0312639 A1 12/2008 Weber
2008/0319387 A1 12/2008 Amisar et al.
2009/0012464 A1 1/2009 Martin
2009/0030400 A1 1/2009 Bose et al.
2009/0043330 A1 2/2009 To
2009/0076445 A1 3/2009 Furnish
2009/0082722 A1 3/2009 Munger et al.
2009/0093829 A1 4/2009 Melsheimer et al.
2009/0131955 A1 5/2009 Wenderow et al.
2009/0138031 A1 5/2009 Tsukernik
2009/0153374 A1 6/2009 Maw et al.
2009/0171332 A1 7/2009 Bonneau
2009/0171368 A1 7/2009 Pearce et al.
2009/0182370 A1 7/2009 Volobuyev et al.
2009/0187143 A1 7/2009 Vreeman
2009/0204078 A1 8/2009 Mitchell et al.
2009/0209857 A1 8/2009 Secretain et al.
2009/0210048 A1 8/2009 Amplatz et al.
2009/0227992 A1 9/2009 Nir et al.
2009/0234321 A1 9/2009 Shapland et al.
2009/0247943 A1 10/2009 Kirschenman et al.
2009/0247993 A1 10/2009 Kirschenman et al.
2009/0254083 A1 10/2009 Wallace et al.
2009/0259200 A1 10/2009 Lampropoulos
2009/0264785 A1 10/2009 Causevic et al.
2009/0264865 A1 10/2009 Kawai
2009/0270800 A1 10/2009 Spurchise et al.
2009/0270888 A1 10/2009 Patel et al.
2009/0275974 A1 11/2009 Marchand et al.
2009/0287190 A1 11/2009 Shippert
2009/0312699 A1 12/2009 Pudelko
2010/0023033 A1 1/2010 Mauch et al.
2010/0030256 A1 2/2010 Dubrul et al.
2010/0049168 A1 2/2010 Parker et al.
2010/0057051 A1 3/2010 Howat et al.
2010/0069833 A1 3/2010 Wenderow et al.
2010/0114017 A1 5/2010 Lenker et al.
2010/0114022 A1 5/2010 Hirszowicz et al.
2010/0125253 A1 5/2010 Olson et al.
2010/0137793 A1 6/2010 Hirszowicz et al.
2010/0175701 A1 7/2010 Reis et al.
2010/0204712 A1 8/2010 Mallaby
2010/0204713 A1 8/2010 Ruiz Morales
2010/0217235 A1 8/2010 Thorstenson et al.
2010/0217276 A1 8/2010 Garrison et al.
2010/0280363 A1 11/2010 Skarda et al.
2010/0286756 A1 11/2010 Dorn
2010/0305502 A1 12/2010 Ferry et al.
2010/0312141 A1 12/2010 Keast et al.
2010/0331916 A1 12/2010 Parramon et al.
2011/0004223 A1 1/2011 Leeflang
2011/0009875 A1 1/2011 Grandfield et al.
2011/0015484 A1 1/2011 Alvarez et al.
2011/0028894 A1 2/2011 Foley et al.
2011/0034986 A1 2/2011 Chou
2011/0054504 A1 3/2011 Porter
2011/0077620 A1 3/2011 deBeer
2011/0082373 A1 4/2011 Gurley et al.
2011/0106200 A1 5/2011 Ziegler
2011/0137399 A1 6/2011 Chomas et al.
2011/0144658 A1 6/2011 Wenderow et al.
2011/0152920 A1 6/2011 Eckhouse et al.
2011/0152998 A1 6/2011 Berez et al.
2011/0166447 A1 7/2011 Windolf
2011/0172700 A1 7/2011 Bose et al.
2011/0178418 A1 7/2011 Avidor et al.
2011/0230859 A1 9/2011 Galdonik et al.
2011/0238010 A1 9/2011 Kirschenman
2011/0238041 A1 9/2011 Lim et al.
2011/0288544 A1 11/2011 Verin et al.
2011/0295217 A1 12/2011 Tanaka et al.
2011/0313318 A1 12/2011 Rule et al.
2012/0016407 A1 1/2012 Sakai
2012/0040858 A1 2/2012 Ford et al.
2012/0041474 A1 2/2012 Eckhouse
2012/0065479 A1 3/2012 Lahiji et al.
2012/0065490 A1 3/2012 Zharov et al.
2012/0071822 A1 3/2012 Romo
2012/0071895 A1 3/2012 Stahler et al.
2012/0078140 A1 3/2012 Nita
2012/0083868 A1 4/2012 Shrivastava et al.
2012/0123327 A1 5/2012 Miller
2012/0143237 A1 6/2012 Cam et al.
2012/0150147 A1 6/2012 Leynov et al.
2012/0172798 A1 7/2012 Miller et al.
2012/0179032 A1 7/2012 Bromander et al.
2012/0245595 A1 9/2012 Kesavadas et al.
2012/0259718 A1 10/2012 Miller et al.
2012/0290067 A1 11/2012 Cam et al.
2012/0296362 A1 11/2012 Cam et al.
2012/0316458 A1 12/2012 Rahman et al.

(56) References Cited

U.S. PATENT DOCUMENTS

2012/0330196 A1 12/2012 Nita
2013/0006225 A1 1/2013 Cucin
2013/0012924 A1 1/2013 Davis et al.
2013/0018318 A1 1/2013 Ravichandran et al.
2013/0018359 A1 1/2013 Coyle
2013/0030408 A1 1/2013 Piferi
2013/0030461 A1 1/2013 Marks et al.
2013/0035537 A1 2/2013 Wallace
2013/0035628 A1 2/2013 Garrison et al.
2013/0046285 A1 2/2013 Griffin et al.
2013/0046374 A1 2/2013 Jones-McMeans
2013/0053704 A1 2/2013 Bernak et al.
2013/0096551 A1 4/2013 Govari et al.
2013/0116701 A1 5/2013 Wang et al.
2013/0131499 A1 5/2013 Chan et al.
2013/0131641 A1 5/2013 Jimenez et al.
2013/0131710 A1 5/2013 Carmeli et al.
2013/0144328 A1 6/2013 Weber et al.
2013/0158511 A1 6/2013 Aggerholm et al.
2013/0158578 A1 6/2013 Ghodke et al.
2013/0214912 A1 8/2013 Beyar et al.
2013/0231678 A1* 9/2013 Wenderow ............ A61B 34/30
606/130
2013/0325055 A1 12/2013 Eckhouse et al.
2014/0025043 A1 1/2014 Wang et al.
2014/0039461 A1 2/2014 Anderson et al.
2014/0046243 A1 2/2014 Ray et al.
2014/0046244 A1 2/2014 Ray et al.
2014/0058321 A1 2/2014 Wenderow et al.
2014/0066900 A1 3/2014 Blacker
2014/0074144 A1 3/2014 Shrivastava et al.
2014/0114287 A1 4/2014 Beasley et al.
2014/0118931 A1 5/2014 Hata
2014/0121555 A1 5/2014 Scott et al.
2014/0121746 A1 5/2014 Kusleika et al.
2014/0150782 A1 6/2014 Vazales
2014/0155932 A1 6/2014 Bose et al.
2014/0155980 A1 6/2014 Turjman et al.
2014/0163364 A1 6/2014 Perers
2014/0163367 A1 6/2014 Eskuri
2014/0200608 A1 7/2014 Brady et al.
2014/0216250 A1 8/2014 Meyer
2014/0228762 A1 8/2014 Capone
2014/0228808 A1 8/2014 Webster et al.
2014/0243742 A1 8/2014 Pacheco et al.
2014/0243882 A1 8/2014 Ma
2014/0249508 A1 9/2014 Wang et al.
2014/0273920 A1 9/2014 Smith
2014/0275832 A1 9/2014 Muehlsteff et al.
2014/0275852 A1 9/2014 Hong et al.
2014/0276016 A1 9/2014 Stigall
2014/0276167 A1 9/2014 Dasgupta et al.
2014/0276233 A1 9/2014 Murphy
2014/0276389 A1 9/2014 Walker
2014/0276618 A1 9/2014 Di Caprio et al.
2014/0276920 A1 9/2014 Hendrick et al.
2014/0276923 A1 9/2014 Miller
2014/0276948 A1 9/2014 Zirps
2014/0277003 A1 9/2014 Hendrick
2014/0288525 A1 9/2014 Fudaba et al.
2014/0296889 A1 10/2014 Avneri et al.
2014/0309533 A1 10/2014 Yamashita et al.
2014/0318702 A1 10/2014 Tegg
2014/0330286 A1 11/2014 Wallace
2014/0343537 A1 11/2014 Eversull et al.
2014/0350645 A1 11/2014 Diller et al.
2014/0358123 A1 12/2014 Ueda
2014/0371718 A1 12/2014 Alvarez et al.
2015/0005704 A1 1/2015 Heisel et al.
2015/0005738 A1 1/2015 Blacker
2015/0005745 A1 1/2015 Bergman et al.
2015/0046148 A1 2/2015 Oh et al.
2015/0073391 A1 3/2015 Hutchins et al.
2015/0088002 A1 3/2015 Podhajsky et al.
2015/0105729 A1 4/2015 Valeti et al.
2015/0119859 A1 4/2015 Cajamarca et al.
2015/0126861 A1 5/2015 Gambhir et al.
2015/0133978 A1 5/2015 Paul, Jr.
2015/0157220 A1 6/2015 Fish et al.
2015/0157252 A1 6/2015 Sabesan
2015/0157772 A1 6/2015 Li et al.
2015/0173782 A1 6/2015 Garrison et al.
2015/0174363 A1 6/2015 Sutermeister et al.
2015/0174368 A1 6/2015 Garrison et al.
2015/0257659 A1 9/2015 Broers et al.
2015/0272683 A1 10/2015 Yang et al.
2015/0290390 A1 10/2015 Ring et al.
2015/0314105 A1 11/2015 Gasparyan
2015/0320478 A1 11/2015 Cosman, Jr.
2015/0320479 A1 11/2015 Cosman, Jr.
2015/0320480 A1 11/2015 Cosman, Jr.
2015/0320481 A1 11/2015 Cosman, Jr.
2015/0327875 A1 11/2015 Look
2015/0335288 A1 11/2015 Toth et al.
2015/0335857 A1 11/2015 Ishikawa
2015/0359547 A1 12/2015 Vale et al.
2015/0366518 A1 12/2015 Sampson
2015/0374483 A1 12/2015 Janardhan
2016/0000443 A1 1/2016 Lilburn et al.
2016/0008572 A1 1/2016 Di Caprio
2016/0030079 A1 2/2016 Cohen
2016/0038174 A1 2/2016 Bruzzi et al.
2016/0051386 A1 2/2016 Haarmann-Theimann
2016/0058459 A1 3/2016 Bowman
2016/0058513 A1 3/2016 Giorgi
2016/0067448 A1 3/2016 Blacker et al.
2016/0074057 A1 3/2016 Jezierski et al.
2016/0081825 A1 3/2016 Sudin et al.
2016/0082502 A1 3/2016 Appleby
2016/0100819 A1 4/2016 Tieu
2016/0128688 A1 5/2016 Garrison et al.
2016/0129221 A1 5/2016 Haverkost et al.
2016/0135829 A1 5/2016 Holochwost et al.
2016/0144157 A1 5/2016 Gulachenski et al.
2016/0151010 A1 6/2016 Erez
2016/0166265 A1 6/2016 Nita
2016/0166266 A1 6/2016 Nita
2016/0184032 A1 6/2016 Romo
2016/0199204 A1 7/2016 Pung et al.
2016/0199620 A1 7/2016 Pokorney et al.
2016/0206216 A1 7/2016 Kirenko
2016/0206322 A1 7/2016 Fitz et al.
2016/0213396 A1 7/2016 Dowell et al.
2016/0220265 A1 8/2016 Pokorney et al.
2016/0220741 A1 8/2016 Garrison et al.
2016/0242764 A1 8/2016 Garrison et al.
2016/0242893 A1 8/2016 Joshi et al.
2016/0243157 A1 8/2016 Cruise et al.
2016/0256611 A1 9/2016 Fitz
2016/0270806 A1 9/2016 Wallace
2016/0271315 A1 9/2016 Chang
2016/0296690 A1 10/2016 Kume et al.
2016/0310702 A1 10/2016 Cabiri
2016/0311990 A1 10/2016 Cruise et al.
2016/0317156 A1 11/2016 Fitz et al.
2016/0317173 A1 11/2016 Hendrick
2016/0317288 A1 11/2016 Rogers et al.
2016/0345904 A1 12/2016 Bowman
2016/0346508 A1 12/2016 Williams et al.
2016/0346515 A1 12/2016 Buller
2016/0354532 A1 12/2016 Olesky et al.
2016/0361180 A1 12/2016 Vong et al.
2016/0361459 A1 12/2016 Baldwin
2016/0367274 A1 12/2016 Wallace
2016/0367275 A1 12/2016 Wallace
2016/0374590 A1 12/2016 Wong et al.
2017/0000576 A1 1/2017 Zirps
2017/0007264 A1 1/2017 Cruise et al.
2017/0007277 A1 1/2017 Drapeau et al.
2017/0014998 A1 1/2017 Langenfeld et al.
2017/0020540 A1 1/2017 Chou et al.
2017/0020627 A1 1/2017 Tesar et al.
2017/0021172 A1 1/2017 Perez et al.
2017/0027604 A1 2/2017 Wallace

(56) References Cited

U.S. PATENT DOCUMENTS

2017/0027653 A1 2/2017 Kirschenman
2017/0028170 A1 2/2017 Ho
2017/0035436 A1 2/2017 Morita
2017/0035446 A1 2/2017 Rapaport et al.
2017/0042548 A1 2/2017 Lam
2017/0043124 A1 2/2017 Vreeman
2017/0056061 A1 3/2017 Ogle et al.
2017/0072163 A1 3/2017 Lim et al.
2017/0072165 A1 3/2017 Lim et al.
2017/0072452 A1 3/2017 Monetti et al.
2017/0079680 A1 3/2017 Bowman
2017/0079812 A1 3/2017 Lam et al.
2017/0079817 A1 3/2017 Sepetka et al.
2017/0079819 A1 3/2017 Pung et al.
2017/0079820 A1 3/2017 Lam et al.
2017/0087340 A1 3/2017 Peralta et al.
2017/0100126 A1 4/2017 Bowman et al.
2017/0100142 A1 4/2017 Look et al.
2017/0105743 A1 4/2017 Vale et al.
2017/0135773 A1 5/2017 Lohmeier et al.
2017/0143416 A1 5/2017 Guler et al.
2017/0143938 A1 5/2017 Ogle et al.
2017/0147765 A1 5/2017 Mehta
2017/0164964 A1 6/2017 Galdonik et al.
2017/0172581 A1 6/2017 Bose et al.
2017/0172766 A1 6/2017 Vong et al.
2017/0181835 A1 6/2017 Kleshinski et al.
2017/0189033 A1 7/2017 Sepetka et al.
2017/0209260 A1 7/2017 Garrison et al.
2017/0215902 A1 8/2017 Leynov et al.
2017/0216484 A1 8/2017 Cruise et al.
2017/0224224 A1 8/2017 Yu
2017/0224350 A1 8/2017 Shimizu et al.
2017/0224355 A1 8/2017 Bowman et al.
2017/0224953 A1 8/2017 Tran et al.
2017/0246014 A1 8/2017 Rapaport et al.
2017/0252025 A1 9/2017 Cabiri et al.
2017/0252057 A1 9/2017 Bonnette et al.
2017/0259037 A1 9/2017 Kern et al.
2017/0265869 A1 9/2017 Cibulski et al.
2017/0265983 A1 9/2017 Lam et al.
2017/0274180 A1 9/2017 Garrison et al.
2017/0281054 A1 10/2017 Stever et al.
2017/0281192 A1 10/2017 Tieu et al.
2017/0281204 A1 10/2017 Garrison et al.
2017/0281288 A1 10/2017 Au
2017/0283536 A1 10/2017 Cruise et al.
2017/0303949 A1 10/2017 Jacobi et al.
2017/0311908 A1 11/2017 Kariv et al.
2017/0317937 A1 11/2017 Dillon
2017/0333000 A1 11/2017 Nystrom et al.
2017/0340867 A1 11/2017 Accisano
2017/0348060 A1 12/2017 Blacker
2017/0348514 A1 12/2017 Guyon et al.
2017/0354421 A1 12/2017 Maguire et al.
2017/0354523 A1 12/2017 Chou et al.
2017/0354803 A1 12/2017 Kume et al.
2017/0360450 A1 12/2017 Tompkins et al.
2017/0361072 A1 12/2017 Chou et al.
2017/0367713 A1 12/2017 Green et al.
2017/0367857 A1 12/2017 Bennett et al.
2017/0368296 A1 12/2017 Chang
2017/0368309 A1 12/2017 Garrison et al.
2018/0008294 A1 1/2018 Garrison et al.
2018/0008439 A9 1/2018 Tieu et al.
2018/0014840 A1 1/2018 Paniam
2018/0028205 A1 2/2018 Chou et al.
2018/0028209 A1 2/2018 Sudin et al.
2018/0036155 A1 2/2018 Tieu et al.
2018/0042623 A1 2/2018 Batiste
2018/0055364 A1 3/2018 Pierro
2018/0055516 A1 3/2018 Bagaoisan et al.
2018/0104390 A1 4/2018 Kilcran
2018/0126122 A1 5/2018 Cabiri
2018/0153477 A1 6/2018 Nagale et al.
2018/0161001 A1 6/2018 Seip
2018/0168751 A1 6/2018 Yi et al.
2018/0169508 A1 6/2018 Billardello et al.
2018/0185104 A1 7/2018 Olson et al.
2018/0199916 A1 7/2018 Sugihara et al.
2018/0200478 A1 7/2018 Lorenzo et al.
2018/0207395 A1 7/2018 Bulman et al.
2018/0207399 A1 7/2018 Chou et al.
2018/0228502 A1 8/2018 Shaffer et al.
2018/0242962 A1 8/2018 Walen et al.
2018/0242980 A1 8/2018 Lubock et al.
2018/0242989 A1 8/2018 Nita
2018/0242999 A1 8/2018 Thatipelli
2018/0250013 A1 9/2018 Wallace et al.
2018/0250086 A1 9/2018 Grubbs
2018/0263632 A1 9/2018 Seifert et al.
2018/0263642 A1 9/2018 Nita
2018/0279965 A1 10/2018 Pandit et al.
2018/0289340 A1 10/2018 Trindade Rodrigues et al.
2018/0296236 A1 10/2018 Goldfarb et al.
2018/0304040 A1 10/2018 Jalgaonkar
2018/0307362 A1 10/2018 Komala et al.
2018/0353194 A1 12/2018 Shaffer et al.
2018/0360398 A1 12/2018 Wenderow et al.
2019/0008360 A1 1/2019 Peh et al.
2019/0008591 A1 1/2019 Desai
2019/0022363 A1 1/2019 Grayzel et al.
2019/0029825 A1 1/2019 Fitterer et al.
2019/0030305 A1 1/2019 Aboytes
2019/0030324 A1 1/2019 Grace et al.
2019/0070387 A1 3/2019 Goyal
2019/0076640 A1 3/2019 Bhatnagar et al.
2019/0108540 A1 4/2019 Look et al.
2019/0111237 A1 4/2019 Cabiri et al.
2019/0125393 A1 5/2019 Hendrick
2019/0133666 A1 5/2019 Johnson
2019/0167124 A1 6/2019 Verkruijsse et al.
2019/0167367 A1 6/2019 Walker et al.
2019/0175030 A1 6/2019 Verkruijsse et al.
2019/0183517 A1 6/2019 Ogle
2019/0200871 A1 7/2019 De Haan
2019/0209026 A1 7/2019 Han et al.
2019/0231373 A1* 8/2019 Quick .................. A61B 17/221
2019/0239910 A1 8/2019 Brade et al.
2019/0254690 A1 8/2019 Cabiri et al.
2019/0254754 A1 8/2019 Johnson
2019/0255297 A1 8/2019 Fischell et al.
2019/0269368 A1 9/2019 Hauck et al.
2019/0274809 A1* 9/2019 Kapec .................. B65D 75/326
2019/0275290 A1 9/2019 Yamashita et al.
2019/0290884 A1 9/2019 Kanemasa et al.
2019/0301913 A1 10/2019 Johnson
2019/0304108 A1 10/2019 Carrell et al.
2019/0329003 A1 10/2019 Watanabe
2019/0336142 A1 11/2019 Torrie
2019/0336227 A1 11/2019 Murphy et al.
2019/0336674 A1 11/2019 Schermeier
2019/0351182 A1 11/2019 Chou et al.
2019/0365485 A1 12/2019 Kottenstette
2019/0380825 A1 12/2019 Perkins et al.
2020/0001046 A1 1/2020 Yang et al.
2020/0008820 A1 1/2020 Aboytes et al.
2020/0008891 A1 1/2020 Wenderow et al.
2020/0008896 A1 1/2020 Cone et al.
2020/0009301 A1 1/2020 Yee
2020/0009350 A1 1/2020 Goyal
2020/0009354 A1 1/2020 Wenderow et al.
2020/0016371 A1 1/2020 Blacker
2020/0022712 A1 1/2020 Deville et al.
2020/0023160 A1 1/2020 Chou et al.
2020/0025845 A1 1/2020 Ferguson et al.
2020/0028181 A1 1/2020 Arugula et al.
2020/0046368 A1 2/2020 Merritt et al.
2020/0046937 A1 2/2020 Nakagawa et al.
2020/0054399 A1 2/2020 Duindam
2020/0054403 A1 2/2020 Zhou et al.
2020/0085528 A1 3/2020 Olson et al.
2020/0129740 A1 4/2020 Kottenstette et al.
2020/0163726 A1 5/2020 Tanner et al.

(56) References Cited

U.S. PATENT DOCUMENTS

2020/0170521 A1 6/2020 Gupta et al.
2020/0170630 A1 6/2020 Wong et al.
2020/0171276 A1 6/2020 Onozuka
2020/0171277 A1 6/2020 Garrison et al.
2020/0187979 A1 6/2020 Bowman
2020/0188630 A1 6/2020 Fujita et al.
2020/0205845 A1 7/2020 Yang et al.
2020/0242767 A1 7/2020 Zhao et al.
2020/0276411 A1 9/2020 Ogle et al.
2020/0282186 A1 9/2020 Blacker et al.
2020/0289136 A1 9/2020 Chou
2020/0289219 A1 9/2020 Denlinger et al.
2020/0297362 A1 9/2020 Deville et al.
2020/0297444 A1 9/2020 Camarillo et al.
2020/0297972 A1 9/2020 Yee et al.
2020/0297973 A1 9/2020 Blacker et al.
2020/0306064 A1 10/2020 Perkins et al.
2020/0306501 A1 10/2020 Yee et al.
2020/0316340 A1 10/2020 Wenderow et al.
2020/0323535 A1 10/2020 Yang et al.
2020/0324084 A1 10/2020 Falb et al.
2020/0337716 A1 10/2020 Garrison et al.
2020/0338308 A1 10/2020 Saber et al.
2020/0345979 A1 11/2020 Loh et al.
2020/0352494 A1 11/2020 Gable et al.
2020/0368494 A1 11/2020 Parmar
2020/0375671 A1 12/2020 Wenderow et al.
2020/0376249 A1 12/2020 Lockhart
2020/0390503 A1 12/2020 Casas et al.
2020/0397451 A1 12/2020 Feltyberger et al.
2020/0405408 A1 12/2020 Shelton, IV et al.
2020/0405410 A1 12/2020 Shelton, IV et al.
2020/0405950 A1* 12/2020 Burren .................. A61M 5/285
2021/0001141 A1 1/2021 Pfiffner
2021/0007816 A1 1/2021 Huang et al.
2021/0022816 A1 1/2021 DeBuys et al.
2021/0030492 A1 2/2021 Wenderow et al.
2021/0045622 A1 2/2021 Petroff et al.
2021/0045758 A1 2/2021 Garrison et al.
2021/0046284 A1 2/2021 Mauch
2021/0052296 A1 2/2021 Garrison
2021/0060767 A1 3/2021 Guerrera et al.
2021/0068852 A1* 3/2021 Spence .................. A61M 1/85
2021/0077211 A1 3/2021 Blacker et al.
2021/0093336 A1 4/2021 Roue
2021/0093406 A1 4/2021 Blacker et al.
2021/0100980 A1 4/2021 Blacker
2021/0106393 A1 4/2021 Simi et al.
2021/0106792 A1 4/2021 Rafiee
2021/0128182 A1 5/2021 Teigen et al.
2021/0145532 A1 5/2021 Tucker et al.
2021/0146094 A1 5/2021 Christian et al.
2021/0153744 A1 5/2021 Pierro
2021/0178032 A1 6/2021 Hsu et al.
2021/0178036 A1 6/2021 Nazarifar et al.
2021/0186534 A1 6/2021 Hunt et al.
2021/0186537 A1 6/2021 Buck et al.
2021/0186542 A1 6/2021 Buck et al.
2021/0187244 A1 6/2021 Buck et al.
2021/0192759 A1 6/2021 Lang
2021/0196242 A1 7/2021 Perez
2021/0196413 A1 7/2021 Inoue
2021/0212792 A1 7/2021 Shelton et al.
2021/0220064 A1 7/2021 Kottenstette et al.
2021/0228841 A1 7/2021 Falb et al.
2021/0244434 A1 8/2021 Popa
2021/0247396 A9 8/2021 Penny et al.
2021/0251472 A1 8/2021 Baez
2021/0259884 A1 8/2021 Heeren et al.
2021/0282863 A1 9/2021 Rafii-Tari et al.
2021/0282867 A1 9/2021 Tegg et al.
2021/0282875 A1 9/2021 Sharon et al.
2021/0282893 A1 9/2021 Leo et al.
2021/0290310 A1 9/2021 Laby et al.
2021/0290320 A1 9/2021 Mao et al.
2021/0290324 A1 9/2021 Mintz et al.
2021/0290327 A1 9/2021 Yates et al.
2021/0298847 A1 9/2021 Mao et al.
2021/0298850 A1 9/2021 Huang et al.
2021/0298857 A1 9/2021 Zheng et al.
2021/0298954 A1 9/2021 Alvarez et al.
2021/0305639 A1 9/2021 Ho et al.
2021/0307767 A1 10/2021 Gifford, III et al.
2021/0315596 A1 10/2021 Buck et al.
2021/0315597 A1 10/2021 Buck et al.
2021/0315598 A1 10/2021 Buck et al.
2021/0316121 A1 10/2021 Buck et al.
2021/0316127 A1 10/2021 Buck et al.
2021/0353129 A1 11/2021 Roelle et al.
2021/0361366 A1 11/2021 Murphy et al.
2021/0361909 A1 11/2021 Cottone et al.
2021/0369370 A1 12/2021 Malanoski
2021/0378527 A1 12/2021 Strasser et al.
2021/0378696 A1 12/2021 Yang et al.
2021/0393275 A1 12/2021 Whelan
2021/0393276 A1 12/2021 Whelan
2021/0393338 A1 12/2021 Graetzel et al.
2021/0401527 A1 12/2021 Hassan
2022/0031415 A1 2/2022 Vargas et al.
2022/0040450 A1 2/2022 Haubert
2022/0047344 A1 2/2022 Stepanauskas
2022/0047849 A1 2/2022 Yee et al.
2022/0080158 A1 3/2022 McLaughlin et al.
2022/0096120 A1 3/2022 Bajo et al.
2022/0151646 A1 5/2022 Dholakia et al.
2022/0167984 A1 6/2022 Shelton, IV
2022/0168000 A1 6/2022 Naglretter et al.
2022/0168001 A1 6/2022 Naglretter et al.
2022/0168002 A1 6/2022 Naglretter et al.
2022/0168010 A1 6/2022 Brinkmann et al.
2022/0168049 A1 6/2022 Tanner et al.
2022/0211452 A1 7/2022 Clark et al.
2022/0211975 A1 7/2022 Yang et al.
2022/0233263 A1* 7/2022 Canale .................. A61B 34/35
2022/0233264 A1 7/2022 Klem
2022/0233820 A1 7/2022 Clark et al.
2022/0241490 A1 8/2022 Marass
2022/0287785 A1 9/2022 Hassan et al.
2022/0313375 A1 10/2022 Zhang et al.
2022/0323096 A1 10/2022 Naglretter et al.
2022/0330960 A1 10/2022 Buck et al.
2022/0331085 A1 10/2022 Buck et al.
2022/0331509 A1 10/2022 Buck et al.
2022/0370161 A1 11/2022 Yu
2022/0370706 A1 11/2022 Meganck
2022/0378522 A1 12/2022 Zemlok et al.
2023/0000563 A1 1/2023 Bell et al.
2023/0035508 A1 2/2023 Clark et al.
2023/0035946 A1 2/2023 Kapadia
2023/0043432 A1 2/2023 Kapadia
2023/0046468 A1 2/2023 Lau et al.
2023/0047098 A1 2/2023 Lau et al.
2023/0048055 A1 2/2023 Lau et al.
2023/0048388 A1 2/2023 Lau et al.
2023/0107693 A1 4/2023 Walker et al.
2023/0116327 A1 4/2023 Walker et al.
2023/0116700 A1 4/2023 Yu et al.
2023/0117715 A1 4/2023 Ho et al.
2023/0126545 A1 4/2023 Liu et al.
2023/0202040 A1 6/2023 Lin et al.
2023/0218816 A1 7/2023 Germain et al.
2023/0310100 A1 10/2023 Wenderow et al.
2023/0347110 A1 11/2023 Wenderow et al.
2023/0355299 A1 11/2023 Cosman
2024/0001101 A1 1/2024 Wallin et al.
2024/0016560 A1 1/2024 Canale et al.
2024/0019042 A1 1/2024 Lim
2024/0032949 A1 2/2024 Yang et al.
2024/0033016 A1 2/2024 Yang et al.
2024/0033017 A1 2/2024 Yang et al.
2024/0033018 A1 2/2024 Yang et al.
2024/0033019 A1 2/2024 Lau et al.
2024/0033486 A1 2/2024 Lau et al.
2024/0041480 A1 2/2024 Bartholomew

(56) References Cited

U.S. PATENT DOCUMENTS

| | | | |
|---|---|---|---|
| 2024/0042124 | A1 | 2/2024 | Bartholomew |
| 2024/0042142 | A1 | 2/2024 | Bartholomew |
| 2024/0130809 | A1 | 4/2024 | Scheunert et al. |
| 2024/0165415 | A1 | 5/2024 | Grosskopf et al. |
| 2024/0180635 | A1 | 6/2024 | Lau et al. |
| 2024/0180640 | A1 | 6/2024 | Lau et al. |
| 2024/0180641 | A1 | 6/2024 | Lau et al. |
| 2024/0180642 | A1 | 6/2024 | Lau et al. |
| 2024/0180643 | A1 | 6/2024 | Lau et al. |
| 2024/0180650 | A1 | 6/2024 | Lau et al. |
| 2024/0180651 | A1 | 6/2024 | Lau et al. |
| 2024/0180652 | A1 | 6/2024 | Lau et al. |
| 2024/0180653 | A1 | 6/2024 | Lau et al. |
| 2024/0180654 | A1 | 6/2024 | Lau et al. |
| 2024/0180658 | A1 | 6/2024 | Lau et al. |
| 2024/0180659 | A1 | 6/2024 | Lau et al. |
| 2024/0181207 | A1 | 6/2024 | Lau et al. |
| 2024/0181208 | A1 | 6/2024 | Lau et al. |
| 2024/0181213 | A1 | 6/2024 | Lau et al. |
| 2024/0181214 | A1 | 6/2024 | Lau et al. |
| 2024/0181224 | A1 | 6/2024 | Lau et al. |
| 2024/0181298 | A1 | 6/2024 | Lau et al. |
| 2024/0183382 | A1 | 6/2024 | Lau et al. |
| 2024/0197416 | A1 | 6/2024 | Gonzalez |
| 2024/0197418 | A1 | 6/2024 | Jourdan |
| 2024/0198051 | A1 | 6/2024 | Jourdan |
| 2024/0207570 | A1 | 6/2024 | Mar |
| 2024/0382668 | A1 | 11/2024 | Bartholomew et al. |
| 2024/0398495 | A1 | 12/2024 | Lee et al. |
| 2025/0032201 | A1 | 1/2025 | Bartholomew et al. |
| 2025/0195835 | A1 | 6/2025 | Totten |
| 2025/0319243 | A1 | 10/2025 | Mar |
| 2025/0352717 | A1 | 11/2025 | Bartholomew |

FOREIGN PATENT DOCUMENTS

| | | | |
|---|---|---|---|
| CN | 101123918 | A | 2/2008 |
| CN | 101252958 | A | 8/2008 |
| CN | 101321552 | A | 12/2008 |
| CN | 101340849 | A | 1/2009 |
| CN | 101795631 | A | 8/2010 |
| CN | 201596219 | U | 10/2010 |
| CN | 102205161 | | 10/2011 |
| CN | 102319097 | A | 1/2012 |
| CN | 102462533 | | 5/2012 |
| CN | 102573701 | A | 7/2012 |
| CN | 102844071 | A | 12/2012 |
| CN | 102847220 | A | 1/2013 |
| CN | 203263993 | U | 11/2013 |
| CN | 103648574 | A | 3/2014 |
| CN | 103764214 | A | 4/2014 |
| CN | 103976766 | | 8/2014 |
| CN | 104042259 | | 9/2014 |
| CN | 203935213 | | 11/2014 |
| CN | 204158457 | U | 2/2015 |
| CN | 104548316 | A | 4/2015 |
| CN | 104622538 | A | 5/2015 |
| CN | 204428157 | | 7/2015 |
| CN | 105120776 | A | 12/2015 |
| CN | 105208951 | A | 12/2015 |
| CN | 204909516 | U | 12/2015 |
| CN | 105534599 | | 5/2016 |
| CN | 105616008 | | 6/2016 |
| CN | 105640648 | | 6/2016 |
| CN | 105662586 | | 6/2016 |
| CN | 105662588 | | 6/2016 |
| CN | 105662589 | | 6/2016 |
| CN | 105796179 | | 7/2016 |
| CN | 205598007 | | 9/2016 |
| CN | 106691414 | | 5/2017 |
| CN | 107307909 | | 11/2017 |
| CN | 107349514 | | 11/2017 |
| CN | 107374737 | | 11/2017 |
| CN | 107374738 | | 11/2017 |
| CN | 107374739 | | 11/2017 |
| CN | 107374740 | | 11/2017 |
| CN | 107374741 | | 11/2017 |
| CN | 107405159 | A | 11/2017 |
| CN | 107550570 | | 1/2018 |
| CN | 107684459 | | 2/2018 |
| CN | 107744405 | | 3/2018 |
| CN | 107744406 | | 3/2018 |
| CN | 107744616 | | 3/2018 |
| CN | 107811624 | | 3/2018 |
| CN | 108158656 | | 6/2018 |
| CN | 108175504 | | 6/2018 |
| CN | 207970143 | | 10/2018 |
| CN | 207979770 | | 10/2018 |
| CN | 207979771 | | 10/2018 |
| CN | 207980153 | | 10/2018 |
| CN | 109567947 | | 4/2019 |
| CN | 208693445 | | 4/2019 |
| CN | 109730779 | | 5/2019 |
| CN | 109730779 | A | 5/2019 |
| CN | 109821137 | A | 5/2019 |
| CN | 208989133 | | 6/2019 |
| CN | 209136865 | | 7/2019 |
| CN | 209137698 | | 7/2019 |
| CN | 110151310 | A | 8/2019 |
| CN | 110236679 | | 9/2019 |
| CN | 209713130 | | 12/2019 |
| CN | 211271130 | | 12/2019 |
| CN | 210056225 | | 2/2020 |
| CN | 110916768 | | 3/2020 |
| CN | 111035453 | | 4/2020 |
| CN | 111110353 | | 5/2020 |
| CN | 111110354 | | 5/2020 |
| CN | 111407416 | | 7/2020 |
| CN | 111437033 | | 7/2020 |
| CN | 111449752 | | 7/2020 |
| CN | 210962301 | | 7/2020 |
| CN | 111658154 | | 9/2020 |
| CN | 111772801 | | 10/2020 |
| CN | 211610046 | | 10/2020 |
| CN | 211723416 | U | 10/2020 |
| CN | 111916214 | | 11/2020 |
| CN | 111931626 | | 11/2020 |
| CN | 111933268 | | 11/2020 |
| CN | 112017516 | | 12/2020 |
| CN | 212089719 | | 12/2020 |
| CN | 212089720 | | 12/2020 |
| CN | 112546396 | | 3/2021 |
| CN | 112546397 | | 3/2021 |
| CN | 112587241 | | 4/2021 |
| CN | 213465314 | | 6/2021 |
| CN | 113303913 | | 8/2021 |
| CN | 113304393 | | 8/2021 |
| CN | 113693733 | | 11/2021 |
| DE | 8900059 | | 5/1989 |
| DE | 10 2010 053111 | | 6/2012 |
| DE | 10 2012 112732 | | 6/2014 |
| EP | 0 330 843 | | 12/1993 |
| EP | 0 582 533 | | 2/1994 |
| EP | 0 309 471 | | 8/1996 |
| EP | 1 776 057 | B1 | 4/2007 |
| EP | 1 349 486 | | 3/2008 |
| EP | 2 069 528 | | 3/2013 |
| EP | 2 937 108 | | 10/2015 |
| EP | 2 928 360 | | 1/2017 |
| EP | 2 211 732 | | 5/2018 |
| EP | 2 124 705 | B1 | 5/2019 |
| EP | 3 539 486 | | 9/2019 |
| EP | 3 698 740 | | 8/2020 |
| FR | 3118406 | | 7/2022 |
| GB | 2077132 | | 12/1981 |
| JP | 2002-535049 | | 10/2002 |
| JP | 2003-527925 | | 9/2003 |
| JP | 2006-087643 | | 4/2006 |
| JP | 2006-102222 | | 4/2006 |
| JP | 2006-521881 | | 9/2006 |
| JP | 2008-502378 | | 1/2008 |
| JP | 2013-504388 | | 2/2013 |
| JP | 2014-515670 | | 7/2014 |
| JP | 2015-504327 | | 2/2015 |

(56) References Cited

FOREIGN PATENT DOCUMENTS

| | | |
|---|---|---|
| WO | WO 1995/009659 | 4/1995 |
| WO | WO 2000/000100 | 1/2000 |
| WO | WO 2006/101170 | 9/2006 |
| WO | WO 2007/102134 | 9/2007 |
| WO | WO 2008/057887 | 10/2008 |
| WO | WO 2009/054968 | 4/2009 |
| WO | WO 09/125575 | 10/2009 |
| WO | WO 2009/132218 | 10/2009 |
| WO | WO 2010/126786 | 11/2010 |
| WO | WO 2013/103885 | 7/2013 |
| WO | WO 2014/151209 | 9/2014 |
| WO | WO 2014/203336 | 12/2014 |
| WO | WO 2016/001712 | 1/2016 |
| WO | WO 2016/191307 | 12/2016 |
| WO | WO 2017/025775 | 2/2017 |
| WO | WO 2017/220010 | 12/2017 |
| WO | WO 2018/121363 | 7/2018 |
| WO | WO 18/169032 | 9/2018 |
| WO | WO 2019/178165 | 9/2019 |
| WO | WO 2019/222518 | 11/2019 |
| WO | WO 2019/222641 | 11/2019 |
| WO | WO 2019/246583 | 12/2019 |
| WO | WO 2020/031147 | 2/2020 |
| WO | WO 2020/061240 | 3/2020 |
| WO | WO 2020/123671 | 6/2020 |
| WO | WO 2020/130924 | 6/2020 |
| WO | WO 2021/004255 | 6/2020 |
| WO | WO 2020/142340 | 7/2020 |
| WO | WO 2020/145928 | 7/2020 |
| WO | WO 2021/011551 | 7/2020 |
| WO | WO 2020/167749 | 8/2020 |
| WO | WO 20/263630 | 12/2020 |
| WO | WO 2021/011533 | 1/2021 |
| WO | WO 2021/011554 | 1/2021 |
| WO | WO 2021/015990 | 1/2021 |
| WO | WO 2021/016213 | 1/2021 |
| WO | WO 2021/064955 | 4/2021 |
| WO | WO 2021/090821 | 5/2021 |
| WO | WO 2021/105658 | 6/2021 |
| WO | WO 2021/126698 | 6/2021 |
| WO | WO 2021/127426 | 6/2021 |
| WO | WO 2021/183444 | 9/2021 |
| WO | WO 2021/184444 | 9/2021 |
| WO | WO 2021/242734 | 12/2021 |
| WO | WO 2022/048984 | 3/2022 |
| WO | WO 2022/115717 | 6/2022 |
| WO | WO 2022/154979 | 7/2022 |

OTHER PUBLICATIONS

US 12,108,960 B1, 10/2024, Teigen et al. (withdrawn)

Bernava et al., Sep. 23, 2019, Direct trhomboaspiration efficacy for mechanical thrombectomy is related to the angle of interaction between the catheter and the clot, J. NeuroIntervent Surg., 0:1-6, doi:10.1136/neurintsurg-2019-015113.

International Search Report and Written Opinion dated Nov. 23, 2022 in application No. PCT/US2022/074688.

International Search Report and Written Opinion dated Dec. 6, 2022 in application No. PCT/US2022/074681.

International Search Report and Written Opinion dated Nov. 16, 2022 in application No. PCT/US2022/074682.

Bell, Apr. 4, 2019, Coding for Empathy, https://www.youtube.com/watch?v=13tzbxofDVc, screenshot of video.

Bency et al., Apr. 25, 2019, Neural Path Planning: Fixed Time, Near-Optimal Path Generation via Oracle Imitation, arXiv: 1904.11102v1 [cs.RO], 8 pp.

Chen et al., Feb. 14, 2020, Deep learning robotic guidance for autonomous vascular access, Nature Machine Intelligence, https://doi.org/10.1038/s42256-020-0148-7, 12 pp.

Das et al., Feb. 21, 2019, Learning-Based Proxy Collision Detection for Robot Motion Planning Applications, arXiv:1902.08164v1 [cs.RO], 19 pp.

Das et al., May 29, 2020, Stochastic Modeling of Distance to Collision for Robot Manipulators, arXiv:2005.14391v1 [cs. RO], 8 pp.

Fagogenis et al., Apr. 2019, Autonomous Robotic Intracardiac Catheter Navigation Using Haptic Vision, Science Robotics, 4(29):1-12.

Guo et al., May 20, 2020, Machine learning-based operation skills assessment with vascular difficulty index for vascular intervention surgery, Medical & Biological Engineering & Computing, https://doi.org/10.1007/s11517-020-02195-9, 15 pp.

Guo et al., Oct. 16, 2020, An Improved Visual Auxiliary Algorithm for the Vascular Interventional Surgical Robot based on Neural Network, Proceedings of 2020 IEEE International Conference on Mechatronics and Automation, http://www.guolab.org/Papers/2020/ICMA2020-329.pdf, pp. 1923-1928.

Johnson et al., Aug. 12, 2020, Dynamically Constrained Motion Planning Networks for Non-Holonomic Robots, arXiv:2008.05112v1 [cs. RO}, 7 pp.

Kuang et al., Apr. 2020, Vibration-Based Multi-Axis Force Sensing: Design, Characterization, and Modeling, IEEE Robotics and Automation Letters, 5(2):3082-3089.

Li et al., 2022, An endovascular catheterization robotic system using collaborative operation with magnetically controlled haptic force feedback, Micromachines, 13:505.

Li et al., Jan. 17, 2021, MPC-MPNet: Model-Predictive Motion Planning Networks for Fast, Near-Optimal Planning Under Kinodynamic Constraints, arXiv:2101.06798v1 [cs. RO], 8 pp.

Qureshi et al., Feb. 2021, Motion Planning Networks: Bridging the Gap Between Learning-Based and Classical Motion Planners, IEEE Transactions on Robotics, 37(1), 19 pp.

Qureshi et al., Jul. 3, 2021, Constrained Motion Planning Networks X, arXiv:2010.08702v2 [cs.RO), 20 pp.

Qureshi et al., Oct. 25-29, 2020, Neural Manipulation Planning on Constraint Manifolds, IEEE Robotics and Automation Letters, 5(4), 8 pp.

Richter et al., Apr. 2021, Autonomous Robotic Suction to Clear the Surgical Field for Hemostasis Using Image-Based Blood Flow Detection, IEEE Robotics and Automation Letters, 6(2), 8 pp.

Sapsalev et al., 2016, Structural model of a magnetic coupling, 17th International Conference of Young Specialists on Micro/Nanotechnologies and Electron Devices EDM 2016, pp. 555-558.

Schreiber et al., Sep. 15, 2020, ARCSnake: An Archimedes Screw-Propelled, Reconfigurable Serpentine Robot for Complex Environments, 2020 IEEE International Conference on Robotics and Automation (ICRA), 6 pp.

Sganga et al., Sep. 15, 2018, OffsetNet: Deep Learning for Localization in the Lung using Rendered Images, arXiv:1809.05645v1 [cs.CV], 7 pp.

Sganga, May 22, 2020, Webinar: Autonomous Surgical Robots, https://www.youtube.com/watch?v=QRO2KnfGlgo, screenshot of video.

Wilcox et al., Jan. 2020, SOLAR-GP: Sparse Online Locally Adaptive Regression Using Gaussian Processes for Bayesian Robot Model Learning and Control, EEE Robotics and Automation Letters, 5(2), 8 pp.

Yip et al., 2017, Autonomous Control of Continuum Robot Manipulators for Complex Cardiac Ablation Tasks, Journal of Medical Robotics Research, 2(1),:1750002-1-1750002-13.

Yip et al., Jul. 10, 2017, Robot Autonomy for Surgery, https://arxiv.org/pdf/1707.03080.pdf, 33 pp.

Abay et al., 2014, Investigation of photoplethysmography and Near Infrared Spectroscopy for the assessment of tissue blood perfusion, 36th Annual International Conference of the IEEE Engineering in Medicine and Biology Society, Chicago, IL, pp. 5361-5364, doi: 10.1109/EMBC.2014.6944837.

Bao et al., Apr. 2018, Operation evaluation in-human of a novel remote-controlled vascular interventional robot, Biomedical Microdevices, 20(2):34.

Bao et al., Feb. 2018, A cooperation of catheters and guidewires-based novel remote-controlled vascular interventional robot, Biomedical Microdevices, 20(1):20.

(56) References Cited

OTHER PUBLICATIONS

Bergman et al., 2020, Robotic-assisted percutaneous coronary intervention, Handbook of Robotic and Image-Guided Surgery, doi: https.//doi.org/10.1016/B978-0-12-814245-5.00020-7.
Guidezilla Guide Extension Catheter, Boston Scientific 510k Submission, Feb. 20, 2017.
Guo et al., Apr. 13, 2018, Study on real-time force feedback for a master-slave interventional surgical robotic system, Biomedical Microdevices, 20(2):37, 12 pp.
Jiang et al., 2018, Initial clinical trial of robot of endovascular treatment with force feedback and cooperating of catheter and guidewire, Applied Bionics and Biomechanics, vol. 2018, Article ID 9735979, 10 pp.
Kagiyama et al., Jul. 31, 2019, First experience of robotic-assisted percutaneous coronary intervention in Japan, Intern Med Advance Publication, doi: 10/2016/internalmedicine.3272-19.
Korpelainen et al., 1995, Asymmetrical skin temperature in ischemic stroke, Stroke, 26(9):1543-1547.
Liu et al., 2021, Animal experiment of a novel neurointerventional surgical robotic system with master-slave mode, Applied Bionics and Biomechanics, vol. 2021, Article ID 8836268, 8 pp.
Merit Medical Systems Acquired Distal Access's SPINR Platform, Jul. 15, 2015, Digital Access, LLC; Merit Medical Systems, 5 pages.
Simon et al., *Exploring the efficacy of cyclic* vs. *static aspiration in a cerebral thrombectomy model: an initial proof of concept study*, J. NeuroIntervent Surg 2014, 6 pp. 677-683.
Simon et al., *Hydrodynamic comparison of the Penumbra system and commonly available syringes in forced—suction thrombectomy*, J. NeuroIntervent Surg 2014, 6, pp. 205-211.
Spiotta et al., Evolution of thrombectomy approaches and devices for acute stroke: a technical review, J. NeuroIntervent Surg 2015, 7, pp. 2-7.
Wang et al., Feb. 3, 2018, Online measuring and evaluation of guidewire inserting resistance for robotic interventional surgery systems, Microsystem Technologies, https://doi/org/10.1007/s00542-018-03750-4.
Zhao et al., Apr. 2, 2018, Operating force information on-line acquisition of a novel slave manipulator for vascular interventional surgery, Biomedical Microdevices, 20(2):33, 13 pp.
Zhou et al., 2021, ADRC-based control method for the vascular intervention master-slave surgical robotic system, Micromachines, 12:1439.
U.S. Appl. No. 15/862,488 (U.S. Pat. No. 10,653,426), filed Jan. 4, 2018 (May 19, 2020), Thromboresistant Coatings for Aneurysm Treatment Devices.
U.S. Appl. No. 16/863,723 (U.S. Pat. No. 11,224,434), filed Apr. 30, 2020 (Jan. 18, 2022), Thromboresistant Coatings for Aneurysm Treatment Devices.
U.S. Appl. No. 17/574,907, filed Jan. 13, 2022, Thromboresistant Coatings for Aneurysm Treatment Devices.
U.S. Appl. No. 15/442,393 (U.S. Pat. No. 10,183,145), filed Feb. 24, 2017 (Jan. 22, 2019), Enhanced Flexibility Neurovascular Catheter.
U.S. Appl. No. 15/443,874 (U.S. Pat. No. 10,835,711), filed Feb. 27, 2017 (Nov. 17, 2020), Telescoping Neurovascular Catheter With Enlargeable Distal Opening.
U.S. Appl. No. 15/443,841(U.S. Pat. No. 10,661,053), filed Feb. 27, 2017 (May 26, 2020), Method of Pulsatile Neurovascular Aspiration With Telescoping Catheter.
U.S. Appl. No. 15/443,838 (U.S. Pat. No. 10,179,224), filed Feb. 27, 2017 (Jan. 15, 2019), Enhanced Flexibility Neurovascular Catheter With Tensile Support.
U.S. Appl. No. 15/443,877 (U.S. Pat. No. 10,183,146), filed Feb. 27, 2017 (Jan. 22, 2019), Method of Making an Enhanced Flexibility Neurovascular Catheter.
U.S. Appl. No. 15/443,948 (U.S. Pat. No. 10,441,745), filed Feb. 27, 2017 (Oct. 15, 2019), Neurovascular Catheter With Enlargeable Distal End.
U.S. Appl. No. 16/542,657 (U.S. Pat. No. 11,147,949), filed Aug. 16, 2019 (Oct. 19, 2021), Method of Making an Enhanced Flexibility Neurovascular Catheter.
U.S. Appl. No. 17/502,389, filed Oct. 15, 2021, Neurovascular Catheter With Enlargeable Distal End.
U.S. Appl. No. 15/444,038 (U.S. Appl. No. 10,183,147), filed Feb. 27, 2017 (Jan. 22, 2019), Neurovascular Catheter Extension Segment.
U.S. Appl. No. 16/833,585, filed Mar. 28, 2020, Enhanced Flexibility Neurovascular Catheter.
U.S. Appl. No. 16/503,899, filed Jul. 5, 2019, Sealed Neurovascular Extendable Catheter.
U.S. Appl. No. 16/802,317, filed Feb. 26, 2020, Catheter With Seamless Flexibility Transitions.
U.S. Appl. No. 16/503,886, filed Jul. 5, 2019, Vacuum Transfer Tool for Extendable Catheter.
U.S. Appl. No. 16/398,626 (U.S. Pat. No. 10,835,272), filed Apr. 30, 2019 (Nov. 17, 2020), Devices and Methods for Removing Obstructive Material From an Intravascular Site.
U.S. Appl. No. 16/400,263 (U.S. Pat. No. 11,123,090), filed May 1, 2019 (Sep. 21, 2021), Neurovascular Catheter Having Atraumatic Angled Tip.
U.S. Appl. No. 16/570,084, filed Sep. 13, 2019, Enhanced Flexibility Neurovascular Catheter With Tensile Support.
U.S. Appl. No. 16/683,718 (U.S. Pat. No. 10,653,434), filed Nov. 14, 2019, (May 19, 2020), Devices and Methods for Removing Obstructive Material From an Intravascular Site.
U.S. Appl. No. 16/704,330 (U.S. Pat. No. 10,786,270), filed Dec. 5, 2019 (Sep. 29, 2020), Neurovascular Aspiration Catheter With Elliptical Aspiration Port.
U.S. Appl. No. 17/410,162, filed Aug. 24, 2021, Neurovascular Catheter Having Angled Tip.
U.S. Appl. No. 16/589,563, filed Oct. 1, 2019, Devices and Methods for Removing Obstructive Material From an Intravascular Site.
U.S. Appl. No. 17/036,258, filed Sep. 29, 2020, Embolic Retrieval Catheter.
U.S. Appl. No. 17/070,832 (U.S. Pat. No. 11,134,859), filed Oct. 14, 2020 (Oct. 5, 2021), Systems and Methods for Multivariate Stroke Detection.
U.S. Appl. No. 17/407,852, filed Aug. 20, 2021, Systems and Methods for Multivariate Stroke Detection.
U.S. Appl. No. 16/728,469, filed Dec. 27, 2019, Neurovascular Access With Dynamic Assistance.
U.S. Appl. No. 17/125,723 (U.S. Pat. No. 11,065,018), filed Dec. 17, 2020 (Jul. 20, 2021), Methods and Systems for Advancing a Catheter to a Target Site.
U.S. Appl. No. 17/125,217, filed Dec. 17, 2020, Methods and Systems for Treating a Pulmonary Embolism.
U.S. Appl. No. 17/125,743, filed Dec. 17, 2020, Systems for Accessing a Central Pulmonary Artery.
U.S. Appl. No. 17/125,742, filed Dec. 17, 2020, Methods and Systems for Accessing and Retrieving Thrombo-Emboli.
U.S. Appl. No. 17/357,490, filed Jun. 24, 2021, Catheter System for Treating Thromboembolic Disease.
U.S. Appl. No. 17/357,558, filed Jun. 24, 2021, Split Dilator Aspiration System.
U.S. Appl. No. 17/357,643, filed Jun. 24, 2021, Methods of Placing Large Bore Aspiration Catheters.
U.S. Appl. No. 17/357,672, filed Jun. 24, 2021, Split Dilator Aspiration System.
U.S. Appl. No. 17/357,715, filed Jun. 24, 2021, Methods of Placing Large Bore Aspiration Catheters.
U.S. Appl. No. 17/475,202, filed Sep. 14, 2021, Enhanced Flexibilitx Neurovascular Catheter.
U.S. Appl. No. 17/343,004 (U.S. Pat. No. 11,207,497), filed Jun. 9, 2021 (Dec. 28, 2021), Catheter With Enhanced Tensile Strength.
U.S. Appl. No. 17/398,244, filed Aug. 10, 2021, Catheter With a Preset Curve.
U.S. Appl. No. 29/811,884, filed Oct. 18, 2021, Inline Fluid Filter.
U.S. Appl. No. 17/527,393, filed Nov. 16, 2021, Catheter Drive System for Supra-Aortic Access.
U.S. Appl. No. 17/527,379, filed Nov. 16, 2021, Catheter Drive System for Supra-Aortic Access.
U.S. Appl. No. 17/527,460, filed Nov. 16, 2021, Sterile Packaging Assembly for Robotic Interventional Device.

(56) References Cited

OTHER PUBLICATIONS

U.S. Appl. No. 17/527,452, filed Nov. 16, 2021, Method of Rob Otically Performing a Neurovascular Procedure.
U.S. Appl. No. 17/527,456, filed Nov. 16, 2021, Multi Catheter Method of Performing a Robotic Neurovascular Procedure.
Bergam et al., 2020, Robotic assisted percutaneous coronary interventions, in Handbook of Robotic and Image Guided Surgery, Elsevier Inc., pp. 341-362.
Evard, Jun. 2018, Catheter localization utilizing a sensor-enabled guidewire design of a proof-of-concept system, Masters' Thesis, California Polytechnic State University, San Luis Obispo, 186 pp.

* cited by examiner

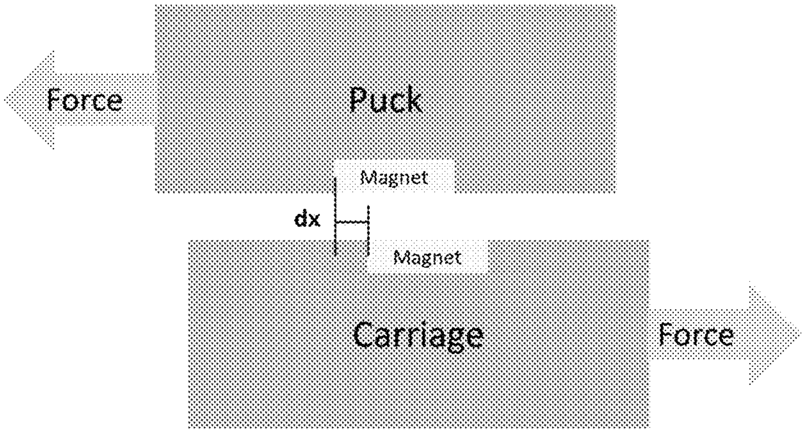
FIG. 13A
Equivalent System
FIG. 13B
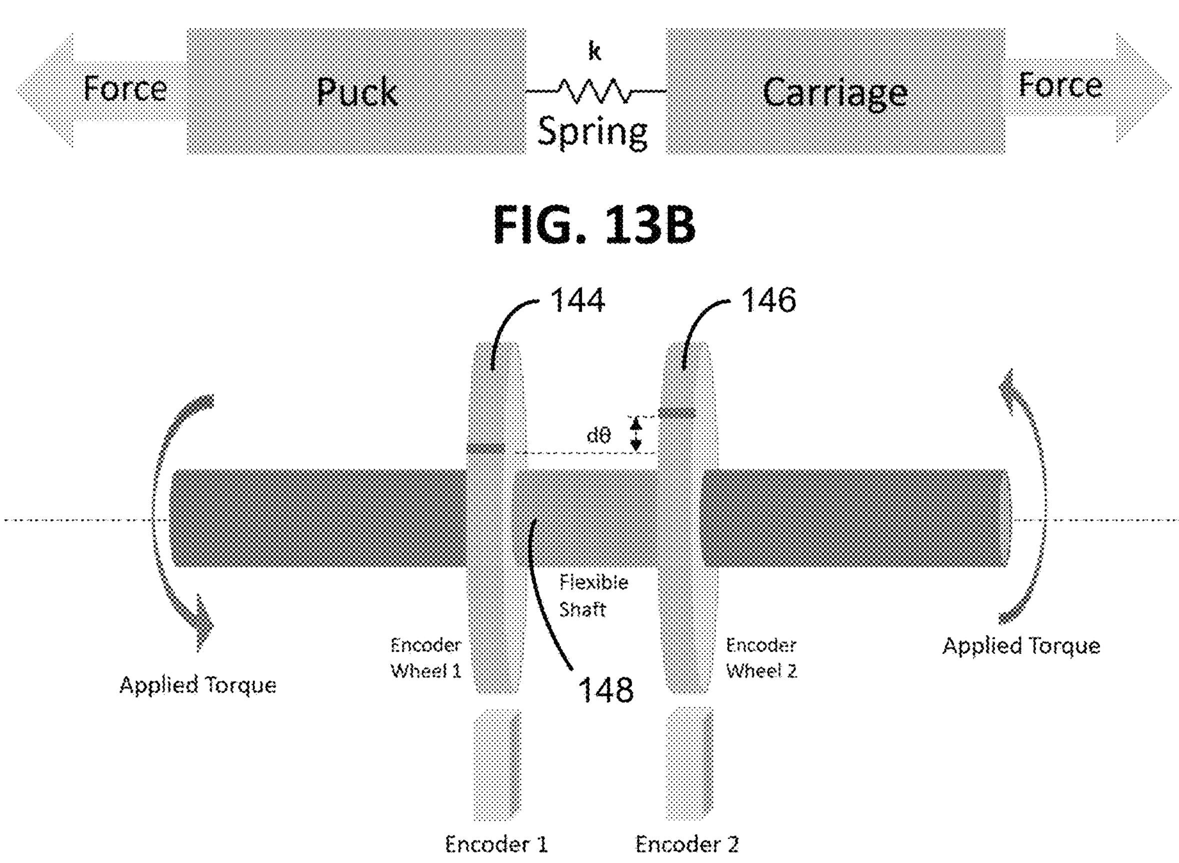
FIG. 14

352
350
381
382
384
320
330
370
380
340
360
310
342

STERILE PACKAGING ASSEMBLY FOR ROBOTIC INTERVENTIONAL DEVICE

CROSS-REFERENCE TO RELATED APPLICATIONS

This application claims the benefit of U.S. Provisional Application No. 63/232,444, filed Aug. 12, 2021, the entirety of this application is hereby incorporated by reference herein.

BACKGROUND OF THE INVENTION

A variety of neurovascular procedures can be accomplished via a transvascular access, including thrombectomy, diagnostic angiography, embolic coil deployment and stent placement. However, the delivery of neurovascular care is limited or delayed by a variety of challenges. For example, there are not enough trained interventionalists and centers to meet the current demand for neuro interventions. Neuro interventions are difficult, with complex set up requirements and demands on the surgeon's dexterity. With two hands, the surgeon must exert precise control over 3-4 coaxial catheters plus manage the fluoroscopy system and patient position. Long, tortuous anatomy, requires delicate, precise maneuvers. Inadvertent catheter motion can occur due to frictional interplay between coaxial shafts and the patient's vasculature. Supra-aortic access necessary to reach the neurovascular is challenging to achieve, especially Type III arches.

Thus, there remains a need for a supra-aortic access system that addresses some or all of these challenges, and increases the availability of neurovascular procedures. Preferably, the system is additionally capable of driving devices further distally through the supra-aortic access to accomplish procedures in the intracranial vessels.

SUMMARY OF THE INVENTION

There is provided in accordance with one aspect of the present invention a supra-aortic access robotic control system. The system comprises a guidewire hub configured to adjust each of an axial position and a rotational position of a guidewire; a guide catheter hub configured to adjust a guide catheter in an axial direction; and an access catheter hub configured to adjust each of an axial position and a rotational position of an access catheter, and also to laterally deflect a distal deflection zone of the access catheter. The guidewire hub may additionally be configured to laterally deflect a distal portion of the guidewire.

There may also be provided a procedure catheter hub configured to manipulate a procedure catheter. Following robotic placement of the guidewire, access catheter and guide catheter such that the guide catheter achieves supra-aortic access, the guidewire and access catheter may be proximally withdrawn, and the procedure catheter advanced through and beyond the guide catheter to reach a neurovascular treatment site. The procedure catheter may be an aspiration catheter; an embolic deployment catheter; a stent deployment catheter; a flow diverter deployment catheter, an access catheter; a diagnostic angiographic catheter; a guiding catheter, an imaging catheter, a physiological sensing/measuring catheter, an infusion or injection catheter, a balloon catheter or a stent retriever.

The control system may further comprise a driven magnet on each of a guidewire hub, an access catheter hub, and a guide catheter hub, configured to cooperate with corresponding drive magnets such that the driven magnet moves in response to movement of the corresponding drive magnet. The drive magnets may each be independently axially movably carried by a support table. The drive magnets may be located outside of the sterile field, separated from the driven magnets by a barrier, and the driven magnets may within the sterile field. The barrier may comprise a tray made from a thin polymer membrane, or any membrane of non-ferromagnetic material.

The control system may further comprise a control console which may be connected to the support table or may be located remotely from the support table. The position of each driven magnet and corresponding hub is movable in response to manual manipulation of a guidewire drive control, access catheter drive control or procedure catheter drive control on the console.

The control system may further comprise a processor for controlling the position of the drive magnets. The processor may be in wired communication with the control console, or in wireless communication with the control console. The driven magnets may be configured to remain engaged with the corresponding drive magnets until application of a disruption force of at least about 300 grams.

There is also provided a robotically driven interventional device. The device comprises an elongate, flexible body, having a proximal end and a distal end. A hub is provided on the proximal end. At least one rotatable roller is provided on a first surface of the hub; and at least one magnet is provided on the first surface of the hub. The roller may extend further away from the first surface than the magnet. The hub may be further provided with at least a second roller.

Any of the guidewire hub, access catheter hub and procedure catheter hub may be further provided with a rotational drive, for rotating the corresponding interventional device with respect to the hub. The hub may be further provided with an axial drive mechanism to distally advance or proximally retract a control element extending axially through the interventional device, to adjust a characteristic such as shape or flexibility of the interventional device. The control element may be an axially movable tubular body or wire such as a pull wire extending through the interventional device to, for example, a distal deflection zone.

There is also provided a control system for controlling movement of interventional devices. In one configuration, the control system comprises a guidewire control, configured to control axial travel and rotation of a guidewire; an access catheter control, configured to control axial and rotational movement of an access catheter; and a guide catheter control, configured to control axial movement of a guide catheter.

The control system may further comprise a deflection control, configured to control deflection of the access catheter, and may be configured for wired or wireless communication with a robotic catheter drive system.

The control system may be configured to independently control the three or more hubs in a variety of modes. For example, two or more hubs may be selectively ganged together so that they drive the respective devices simultaneously and with the same motion. Alternatively, the control system may be configured to drive respective devices simultaneously but with different motions.

The control system may further comprise a physician interface for operating the control system. The physician interface may be carried by a support table having a robotic interventional device drive system. Alternatively, the physician interface for operating the control system may be carried on a portable, handheld device or desktop computer, and may be located in the same room as the patient, the same facility as the patient, or in a remote facility.

The control system may further comprise a graphical user interface with at least one display for indicating the status of at least one device parameter, and/or indicating the status of at least one patient parameter.

There is also provided a sterile packaging assembly for transporting interventional devices to a robotic surgery site. The packaging assembly may comprise a base and a sterile barrier configured to enclose a sterile volume. At least one interventional device may be provided within the sterile volume, the device including a hub and an elongate flexible body. The hub may include at least one magnet and at least one roller configured to roll on the base.

In one implementation, the sterile barrier is removably attached to the base to define the enclosed volume between the sterile barrier and the base. In another implementation, the sterile barrier is in the form of a tubular enclosure for enclosing the sterile volume. The tubular enclosure may surround the base and the at least one interventional device, which are within the sterile volume.

The hub may be oriented within the packaging such that the roller and the magnet face the base. Alternatively, the base may be in the form of a tray having an elongate central axis. An upper, sterile field side of the tray may have an elongate support surface for supporting and permitting sliding movement of one or more hubs. At least one and optionally two elongate trays may be provided, extending parallel to the central axis. At least one hub and interventional device may be provided in the tray, and the sterile tray with sterile hub and interventional device may be positioned in a sterile volume defined by a sterile barrier.

The base may be configured to reside on a support table adjacent a patient, with an upper surface of the base within a sterile field and a lower surface of the base outside of the sterile field.

Any of the hubs disclosed herein may further comprises a fluid injection port and/or a wireless RF transceiver. The hub may comprise a visual indicator, for indicating the presence of a clot. The visual indicator may comprise a clot chamber having a transparent window. A filter may be provided in the clot chamber.

Any of the hubs disclosed herein may further comprise a sensor for detecting a parameter of interest such as the presence of a clot. The sensor, in some instances, may be positioned on a flexible body. The sensor may comprise a pressure sensor or an optical sensor. In some embodiments, the sensor may comprise one or more of a force sensor, a temperature sensor, and/or an oxygen sensor. In some embodiments, the sensor may comprise a Fiber Bragg grating sensor. For example, a Fiber Bragg grating sensor (e.g., an optical fiber) may detect strain locally that can facilitate the detection and/or determination of force being applied. The device may further include a plurality of sensors. The plurality of sensors may each comprise one or more of any type of sensor disclosed herein. In some embodiments, a plurality (e.g., 3 or more) of sensors (e.g., Fiber Bragg grating sensors) may be distributed around a perimeter to facilitate the detection and/or determination of shape. The position of the device, in some instance, may be determined through the use of one or more sensors to detect and/or determine the position. For example, one or more optical encoders may be located in or proximate to one or more the motors that drive linear motion such that the optical encoders may determine a position.

There is also provided a method of performing a neurovascular procedure, in which a first phase includes robotically achieving supra-aortic access, and a second phase includes manually or robotically performing a neurovascular procedure via the supra-aortic access. The method comprises the steps of providing an access catheter having an access catheter hub; coupling the access catheter hub to a hub adapter movably carried by a support table; driving the access catheter in response to movement of the hub adapter along the table until the access catheter is positioned to achieve supra-aortic access. The access catheter and access catheter hub may then be decoupled from the hub adapter; and a procedure catheter hub having a procedure catheter may then be coupled to the hub adapter.

The method may additionally comprise advancing the procedure catheter hub to position a distal end of the procedure catheter at a neurovascular treatment site. The driving the access catheter step may comprise driving the access catheter distally through a guide catheter. The driving the access catheter step may include the step of laterally deflecting a distal region of the access catheter to achieve supra-aortic access.

There is also provided a method of performing a neurovascular procedure, comprising the steps of providing an access assembly comprising a guidewire, access catheter and guide catheter. The access assembly may be releasably coupled to a robotic drive system. The access assembly may be driven by the robotic drive system to achieve access to a desired point, such as to achieve supra-aortic access. The guide wire and the access catheter may then be decoupled from the access assembly, leaving the guide catheter in place. A procedure assembly may be provided, comprising at least a guidewire and a first procedure catheter. The procedure assembly may be releasably coupled to the robotic drive system; and a neurovascular procedure may be accomplished using the procedure assembly. A second procedure catheter may also be provided, for extending through the first procedure catheter to a treatment site.

The coupling the access assembly step may comprise magnetically coupling a hub on each of the guidewire, access catheter and guide catheter, to separate corresponding couplers carrying corresponding drive magnets independently movably carried by the drive table. The procedure assembly may comprise a guidewire, a first catheter and a second catheter. The guidewire and first catheter may be positioned concentrically within the second catheter. The procedure assembly may be advanced as a unit through at least a portion of the length of the guide catheter, and the procedure may comprise a neurovascular thrombectomy.

Additional features and advantages of the present invention are disclosed in Appendix A and Appendix B to U.S. Provisional Application No. 63/232,444, the entirety of each of which is hereby incorporated by reference herein.

BRIEF DESCRIPTION OF THE DRAWINGS

FIGS. 13A and 13B schematically illustrate a sensor for measuring elastic forces at the magnetic coupling between the hub and corresponding carriage.

FIG. 14 schematically illustrates a dual encoder torque sensor for use with a catheter of the present invention.

DETAILED DESCRIPTION OF THE PREFERRED EMBODIMENT

The present invention provides a system for advancing a guide catheter from a femoral artery or radial artery access into the ostium of one of the great vessels at the top of the aortic arch, thereby achieving supra-aortic access. A surgeon can then take over and advance interventional devices into the cerebral vasculature via the robotically placed guide catheter.

In some implementations of the invention, the system may additionally be configured to robotically gain intracranial vascular access and to perform an aspiration thrombectomy or other neuro vascular procedure.

A drive table is positioned over or alongside the patient, and configured to axially advance, retract, and in some cases rotate and/or laterally deflect two or three or more different (e.g., concentrically or side by side oriented) intravascular devices. Each device has a proximal end attached to a unique hub, sometimes referred to as a "puck". The hub is moveable along a path along the surface of the drive table to advance or retract the interventional device as desired. Each hub may also contain mechanisms to rotate or deflect the device as desired, and is connected to fluid delivery tubes (not shown) of the type conventionally attached to a catheter hub. Each hub is in electrical communication with an electronic control system, either via hard wired connection, RF wireless connection or a combination of both.

Each hub is independently movable across the surface of a sterile field barrier membrane carried by the drive table. Each hub is releasably magnetically coupled to a unique drive carriage on the table side of the sterile field barrier. The drive system independently moves each hub in a proximal or distal direction across the surface of the barrier, to move the corresponding interventional device approximately or distally within the patient's vasculature.

The carriages on the drive table which magnetically couple with the hubs to provides linear motion actuation are universal. Functionality of the catheters/guidewire are provided based on what is contained in the hubs and the shaft designs. This allows flexibility to configure the system to do a wide range of procedures using a wide variety of interventional devices on the same drive table.

Figure 1:
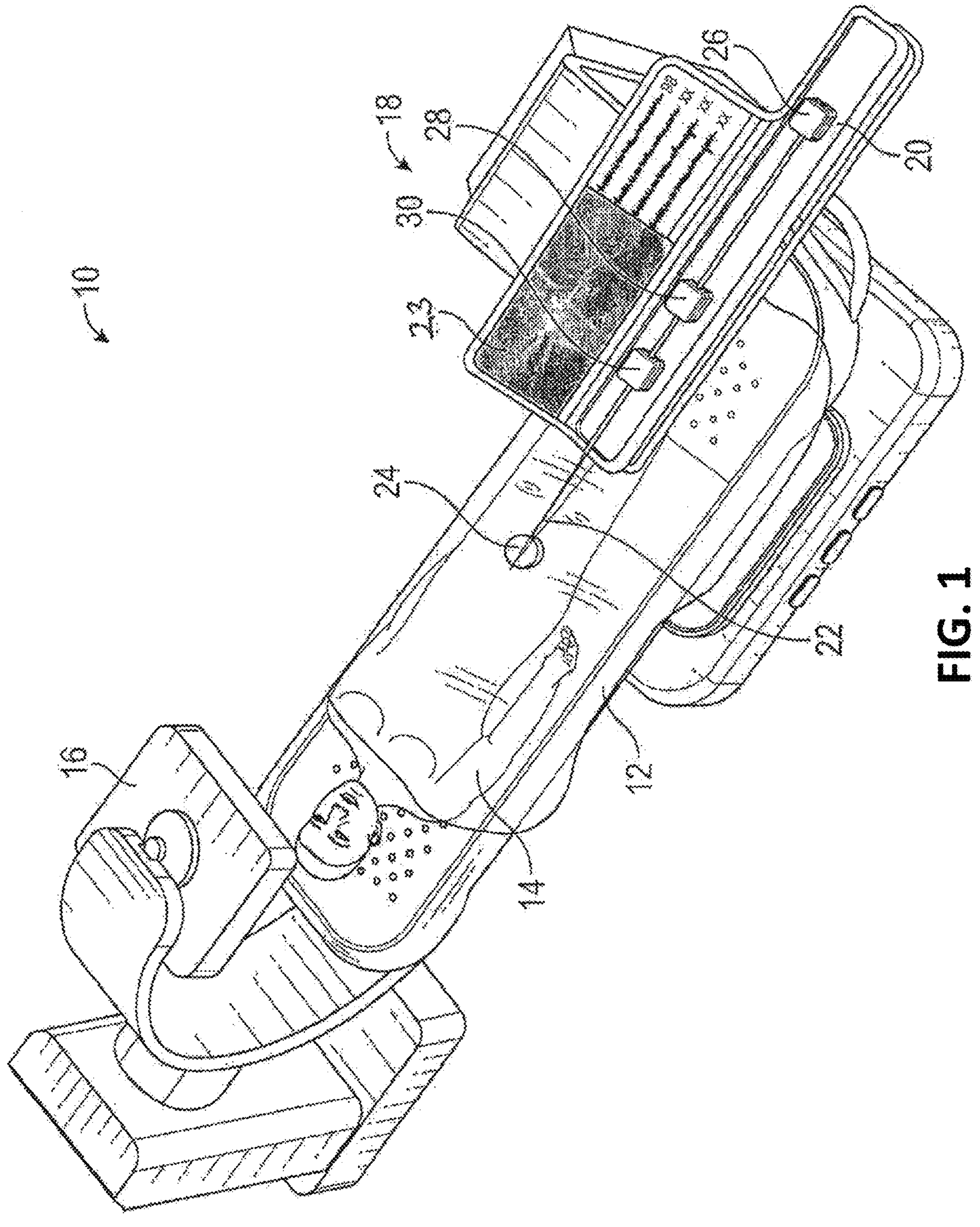
FIG. 1 is a schematic perspective view of an interventional setup having an imaging system, a patient support table, and a robotic drive system in accordance with the present invention.

FIG. 1 is a schematic perspective view of an interventional setup 10 having a patient support table 12 for supporting a patient 14. An imaging system 16 may be provided, along with a robotic interventional device drive system 18 in accordance with the present invention.

The drive system 18 may include a support table 20 for supporting, for example, a guidewire hub 26, an access catheter hub 28 and a guide catheter hub 30. In the present context, the term 'access' catheter can be any catheter having a lumen with at least one distally facing or laterally facing distal opening, that may be utilized to aspirate thrombus, provide access for an additional device to be advanced therethrough or there along, or to inject saline or contrast media or therapeutic agents.

More or fewer interventional device hubs may be provided depending upon the desired clinical procedure. Multiple interventional devices 22 extend between the support table 20 and (in the illustrated example) a femoral access point 24 on the patient 14. Depending upon the desired procedure, access may be achieved by percutaneous or cut down access to any of a variety of arteries or veins, such as the femoral artery or radial artery. Although disclosed herein primarily in the context of neuro vascular access and procedures, the robotic drive system and associated interventional devices can readily be configured for use in a wide variety of additional medical interventions, in the peripheral and coronary arterial and venous vasculature, gastrointestinal system, pulmonary airways, treatment sites reached via trans ureteral or urethral or fallopian tube navigation, or other hollow organs or structures in the body.

A display 23 such as for viewing fluoroscopic images, catheter data (e.g., fiber Bragg grating fiber optics sensor data or other force or shape sensing data) or other patient data may be carried by the support table 20 and or patient support 12. Alternatively, the physician input/output interface including display 23 may be remote from the patient, such as behind radiation shielding, in a different room from the patient, or in a different facility than the patient.

In the illustrated example, a guidewire hub 26 is carried by the support table 20 and is moveable along the table to advance a guidewire into and out of the patient 14. An access catheter hub 28 is also carried by the support table 20 and is movable along the table to advance the access catheter into and out of the patient 14. The access catheter hub may also be configured to rotate the access catheter in response to manipulation of a rotation control, and may also be configured to laterally deflect a deflectable portion of the access catheter, in response to manipulation of a deflection control.

Figure 2:
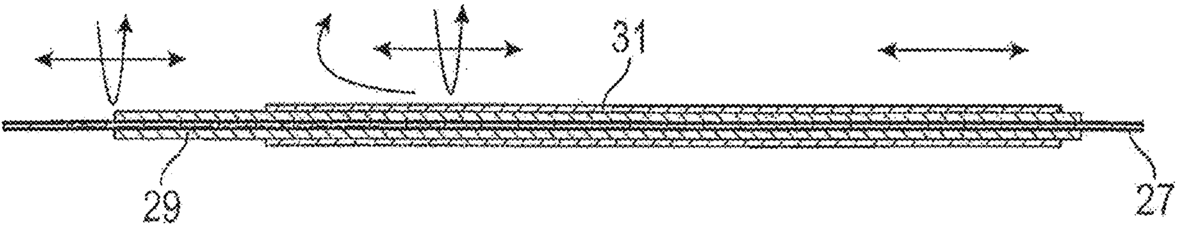
FIG. 2 is a longitudinal cross section showing the concentric relationship between a guidewire having two degrees of freedom, an access catheter having 3 degrees of freedom and a guide catheter having one degree of freedom.

FIG. 2 is a longitudinal cross section schematically showing the motion relationship between a guidewire 27 having two degrees of freedom (axial and rotation), an access catheter 29 having three degrees of freedom (axial, rotational and lateral deflection) and a guide catheter 31, having one degree of freedom (axial).

Figure 3A:
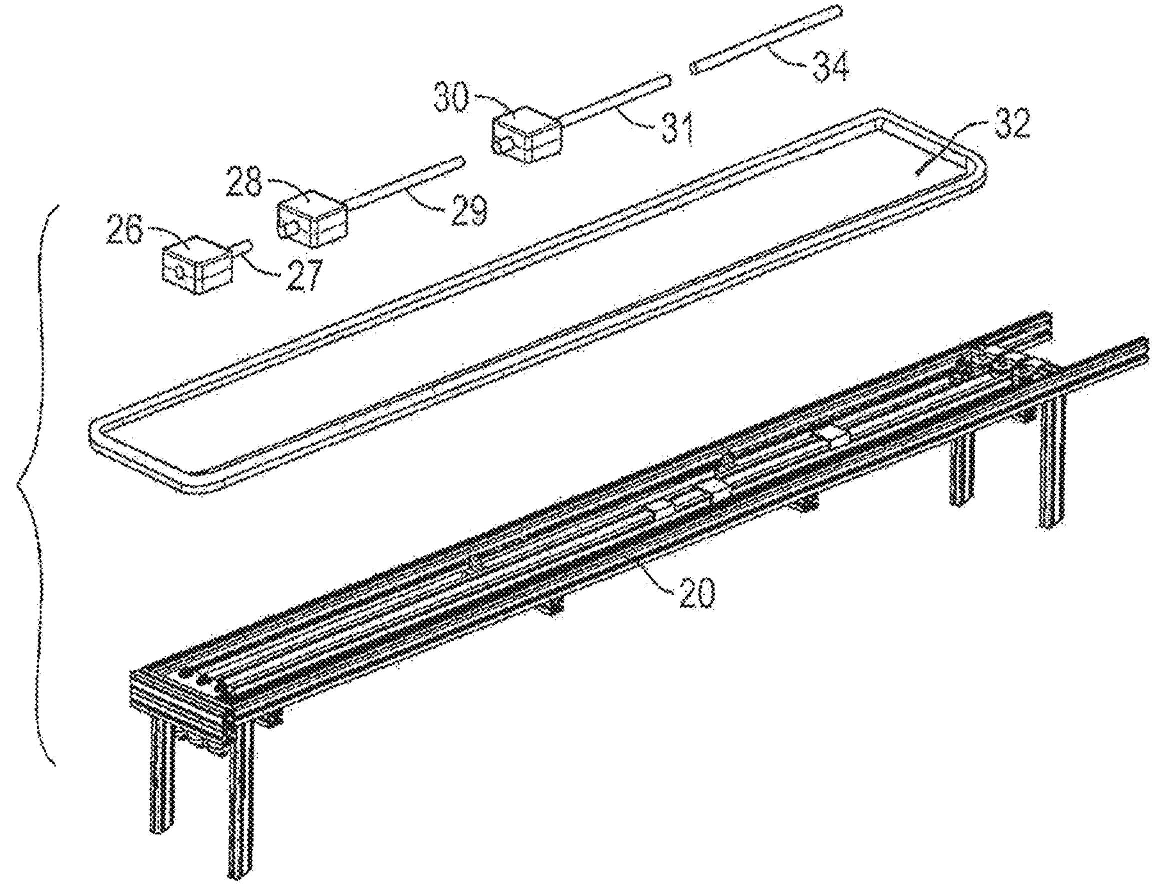
FIG. 3A is an exploded schematic view of interventional device hubs separated from a support table by a sterile barrier.

Referring to FIG. 3A, the support table 20 includes a drive mechanism described in greater detail below, to independently drive the guidewire hub 26, access catheter hub 28, and guide catheter hub 30. An anti-buckling feature 34 may be provided in a proximal anti buckling zone for resisting buckling of the portion of the interventional devices spanning the distance between the support table 20 and the femoral artery access point 24. The anti-buckling feature 34 may comprise a plurality of concentric telescopically axially extendable and collapsible tubes through which the interventional devices extend.

Alternatively, a proximal segment of one or more of the device shafts may be configured with enhanced stiffness to reduce buckling under compression. For example, a proximal reinforced segment may extend distally from the hub through a distance of at least about 5 cm or 10 cm but typically no more than about 130 cm or about 100 cm or about 50 cm or about 30 cm to support the device between the hub and the access point 24 on the patient. Reinforcement may be accomplished by embedding at least one or two or more axially extending elements into the wall, such as elongate wires or ribbons. Alternatively, thin tubular stiffening structures can be embedded within or carried over the outside of the device wall, such as a tubular polymeric extrusion or length of hypo-tube. Alternatively, a removable stiffening mandrel may be placed within a lumen in the proximal segment of the device, and proximally removed following distal advance of the hub towards the patient access site, to prevent buckling of the proximal shafts during distal advance of the hub. Alternatively, the wall thickness or diameter of the interventional device can be increased in the anti-buckling zone.

The interventional device hubs may be separated from the support table 20 by sterile barrier 32. Sterile barrier 32 may comprise a thin plastic membrane such as PET. This allows the support table 20 and associated drive system to reside on a non-sterile (lower) side of sterile barrier 32. The guidewire hub 26, access catheter hub 28, guide catheter hub 30 and the associated interventional devices are all on a sterile (top) side of the sterile barrier 32. The sterile barrier is preferably waterproof and can also serve as a tray used in the packaging of the interventional devices, discussed further below. The interventional devices can be provided individually or as a coaxially preassembled kit that is shipped and stored in the tray and enclosed within a sterile packaging.

FIGS. 3B-3F schematically illustrate an alternate sterile barrier in the form of a dual function sterile barrier for placement on the support table during the interventional procedure, and shipping tray, having one or more storage channels for carrying sterile interventional devices.

Figure 3B:
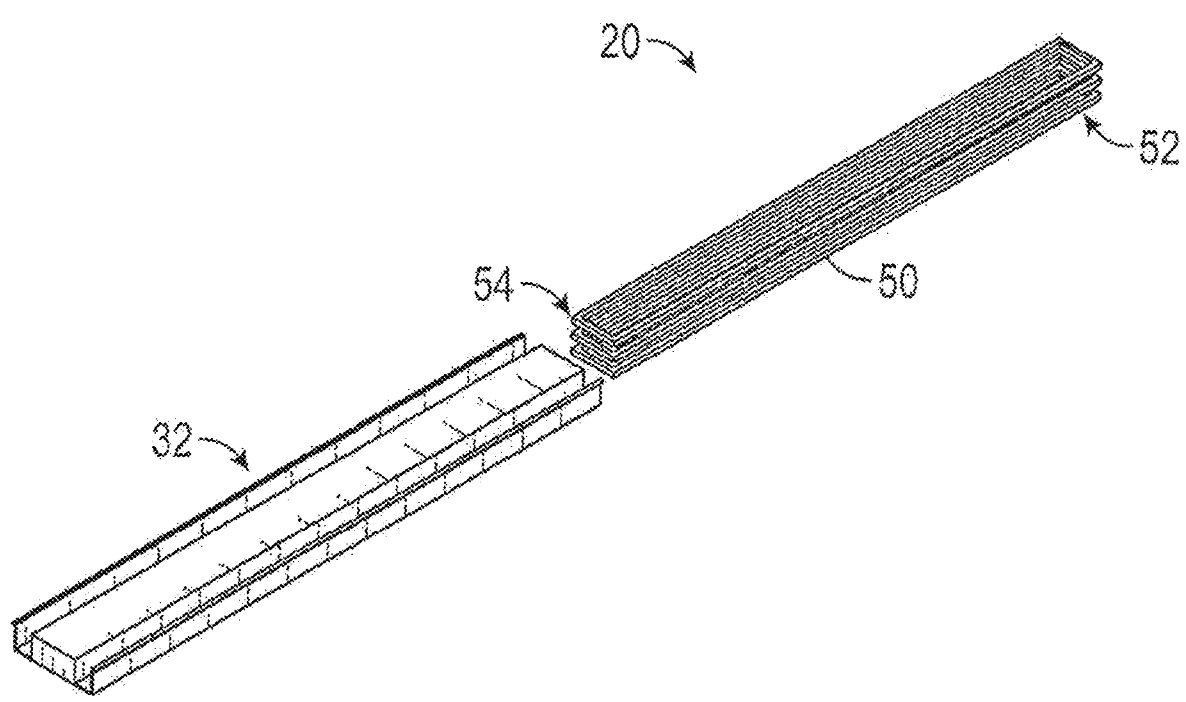
FIGS. 3B-3F Show an alternate sterile barrier in the form of a shipping tray having one or more storage channels for carrying interventional devices.
Figure 3C:
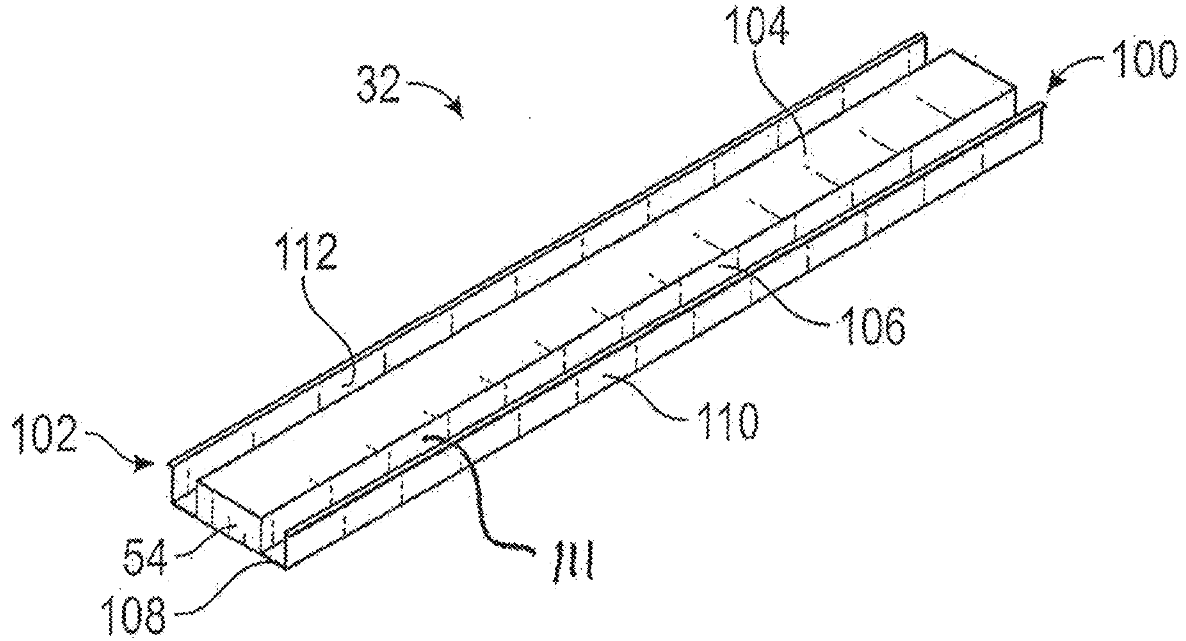

Referring to FIGS. 3B and 3C, there is illustrated a sterile barrier 32 in the form of a pre-shaped tray, for fitting over an elongate support table 20. The sterile barrier 32 extends between a proximal end 100 and a distal end 102 and includes an upper support surface 104 for supporting the interventional device hubs. In one implementation, the support surface 104 has an axial length greater than the length of the intended interventional devices, in a linear drive configuration. The length of support surface 104 will typically be at least about 150 cm or about 180 cm in a linear drive table. Shorter lengths may be utilized in a system configured to advance the drive couplers along an arcuate path.

At least a first channel 106 may be provided, extending axially at least a portion of the length of the support table 20. In the illustrated implementation, first channel 106 extends the entire length of the support table 20. Preferably, the first channel 106 has a sufficient length to hold the interventional devices, and sufficient width and depth to hold the corresponding hubs. First channel 106 is defined within a floor 108, outer side wall 110 and inner side wall 111, forming an upwardly facing concavity. Optionally, a second channel 112 may be provided. Second channel 112 may be located on the same side or the opposite side of the upper support surface 104 from the first channel 106. Two or three or more additional recesses such as additional channels or wells may be provided, to hold additional medical devices or supplies that may be useful during the interventional procedure.

Figure 3D:
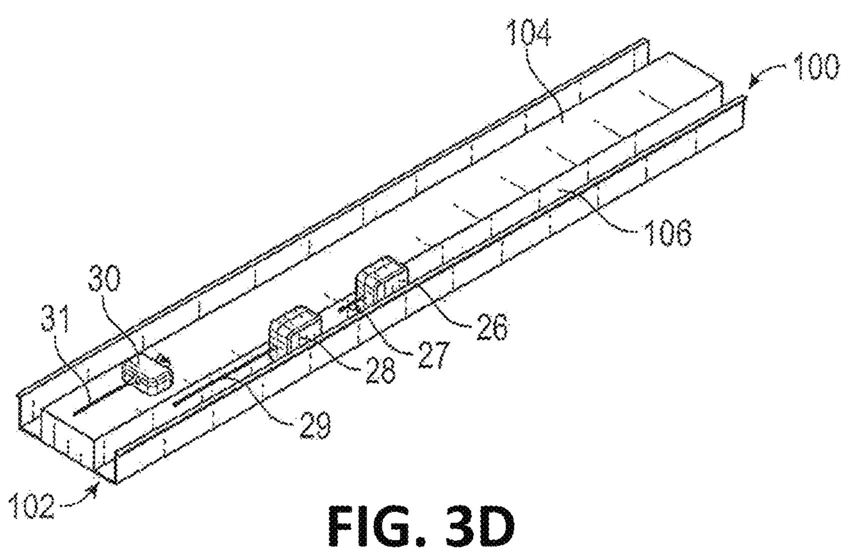

Referring to FIG. 3D, the guide catheter hub 30 is shown positioned on the upper support surface 104, and magnetically coupled to the corresponding coupler holding the drive magnets, positioned beneath the sterile barrier 32. The access catheter hub 28 and access catheter 29, and guide wire hub 26 and guide wire 27 are illustrated residing within the first channel 106 such as before introduction through the guide catheter 31 or following removal from the guide catheter 31. The length of the catheters has been cut down to simplify the drawing.

The interventional devices may be positioned within the channel 106 and enclosed in a sterile barrier for shipping. The sterile barrier containing the sterile interventional devices may be contained within a second, outer sealed container such as a membrane pouch, which may be a second, outer sterile barrier At the clinical site, an upper panel of the sterile barrier may be removed, or an outer tubular sterile barrier packaging may be opened and axially removed from the support table 20 and sterile barrier 32 assembly, exposing the sterile top side of the sterile barrier tray and any included interventional devices. The interventional devices may be separately carried in the channel, or preassembled into an access assembly or procedure assembly, discussed in additional detail below.

Figure 3E:
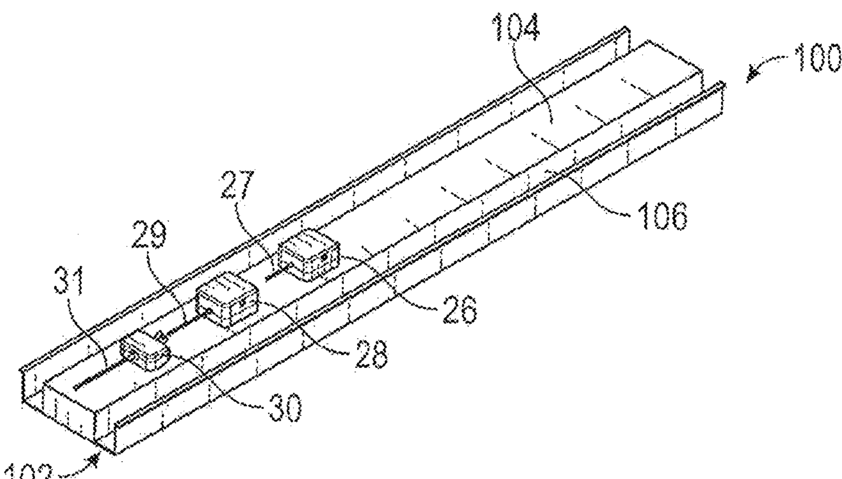
Figure 3F:
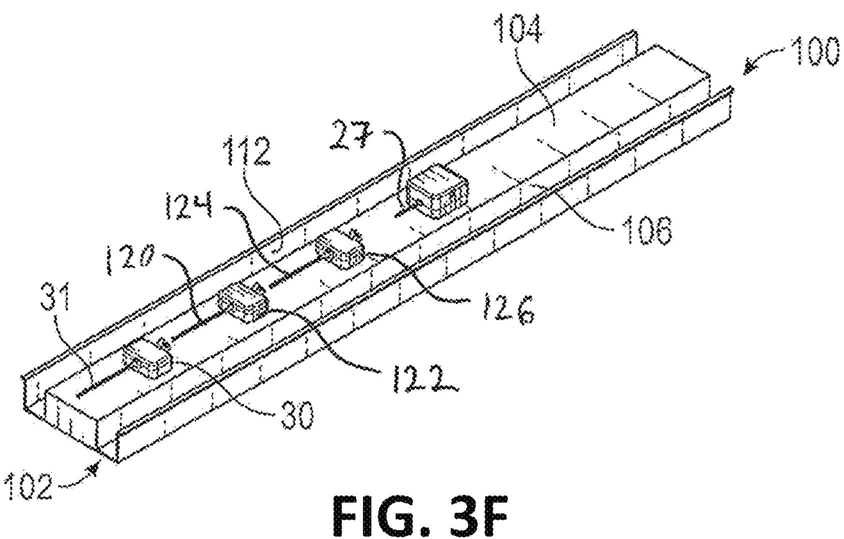

FIGS. 3D-3F illustrate the support table with sterile barrier in place, and in FIG. 3E the interventional devices configured in an access assembly for aortic access, following coupling of the access assembly to the corresponding carriages beneath the sterile barrier. The access assembly may be pre-assembled with the guidewire fully advanced through the access catheter which is in turn fully advanced through the guide catheter. This access assembly may be lifted out of the channel 106 as a unit and positioned on the support surface 104 for coupling to the respective drive magnets and introduction into the patient. The guide catheter hub 30 is the distal most hub. Access catheter hub 28 is positioned proximally of the guide catheter hub, so that the access catheter 29 can extend distally through the guide catheter. The guide wire hub 26 is positioned most proximally, in order to allow the guide wire 27 to advance through the access catheter 29 and guide catheter 31.

A procedure assembly is illustrated in FIG. 3F following introduction of the procedure assembly through the guide catheter 31 that was used to achieve supra-aortic access. In this implementation, guide catheter 31 remains the distal most of the interventional devices. A first procedure catheter 120 and corresponding hub 122 is illustrated extending through the guide catheter 31. An optional second procedure catheter 124 and corresponding hub 126 is illustrated extending through the first procedure catheter 120. The guide wire 27 extends through at least a portion of the second procedure catheter 124 in a rapid exchange version of second procedure catheter 124, or the entire length of second procedure catheter 124 in an over the wire implementation.

In one commercial execution, a preassembled access assembly (guide catheter, access catheter and guidewire) may be carried within a first channel on the sterile barrier tray and a preassembled procedure assembly (one or two procedure catheters and a guidewire) may be carried within the same or a different, second channel on the sterile barrier tray. One or two or more additional catheters or interventional tools may also be provided, depending upon potential needs during the interventional procedure.

Figures 4, 5A, 5B:
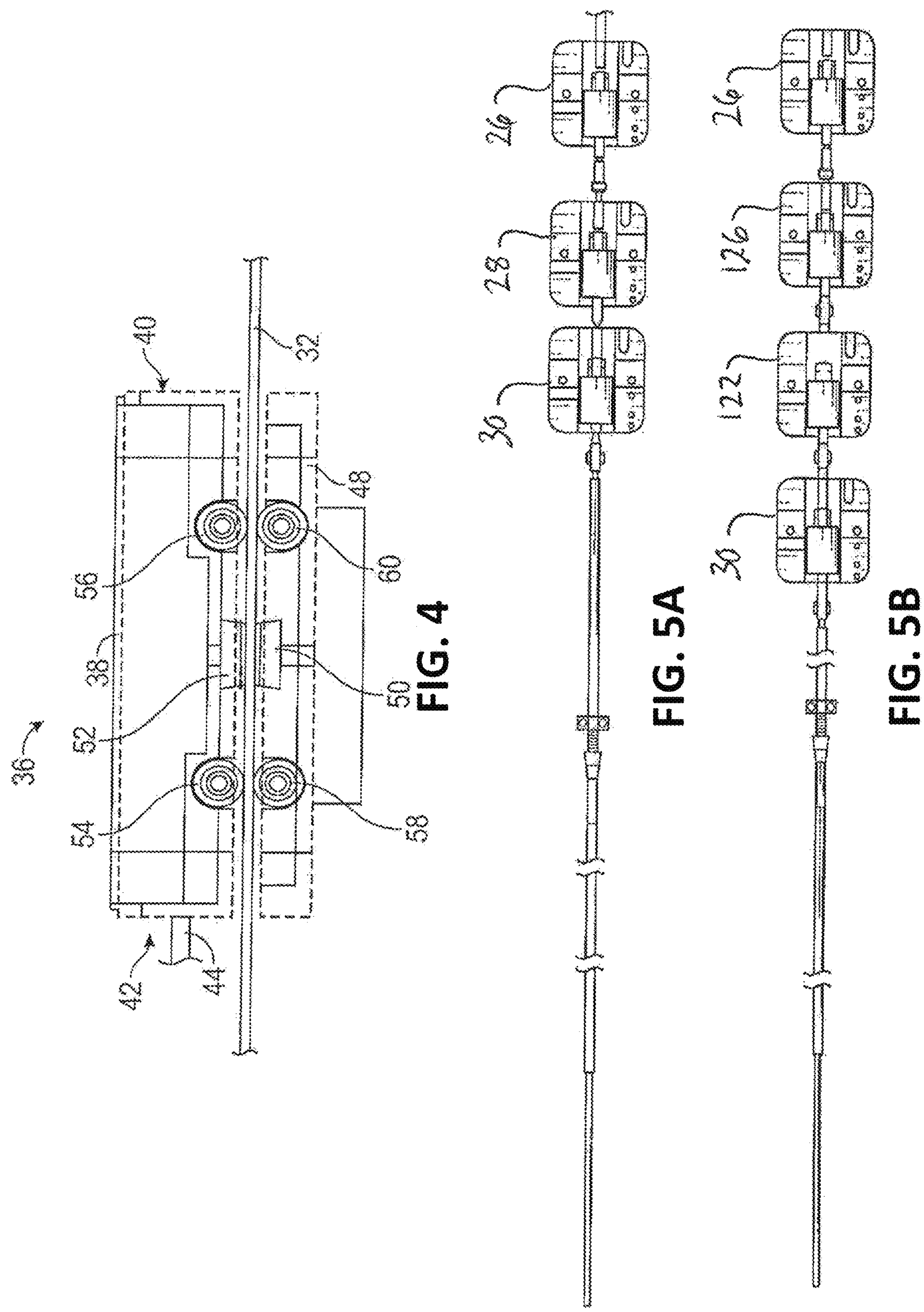
FIG. 4 is a schematic elevational cross section through a hub adapter having a drive magnet separated from an interventional device hub and driven magnet by a sterile barrier.
FIGS. 5A and 5B schematically illustrate a three interventional device and a four interventional device assembly.

Referring to FIG. 4, hub 36 may represent any of the hubs previously described. Hub 36 includes a housing 38 which extends between a proximal end 40 and a distal end 42. An interventional device 44, which could be any of the interventional devices disclosed herein, extends distally from the hub 36 and into the patient 14 (not illustrated). A hub adapter 48 or carriage acts as a shuttle by advancing proximally or distally along a track in response to operator instructions. The hub adapter 48 includes at least one drive magnet 50 configured to couple with a driven magnet 52 carried by the hub 36. This provides a magnetic coupling between the drive magnet 50 and driven magnet 52 through the sterile barrier 32 such that the hub 36 and associated interventional device is moved across the top of the sterile barrier 32 within the sterile field in response to movement of the hub adapter 48 outside of the sterile field. Movement of the hub adapter is driven by a drive system carried by the support table and described in additional detail below.

To reduce friction in the system, the hub 36 may be provided with at least a first roller 54 and a second roller 56 which may be in the form of wheels or rotatable balls or drums. The rollers space the sterile barrier 32 apart from the surface of the driven magnet 52 by at least about 0.008" and generally no more than about 0.03". In some implementations of the invention the space is within the range of from about 0.010" and about 0.016". The space between the drive magnet 50 and driven magnet 52 is generally no more than about 0.15" and in some implementations is no more than about 0.10" such as within the range of from about 0.085" to about 0.090". The hub adapter 48 may similarly be provided with at least a first hub adapter roller 58 and the second hub adapter roller 60, which may be positioned opposite the respective first roller 54 and second roller 56 as illustrated in FIG. 4.

Figure 6:
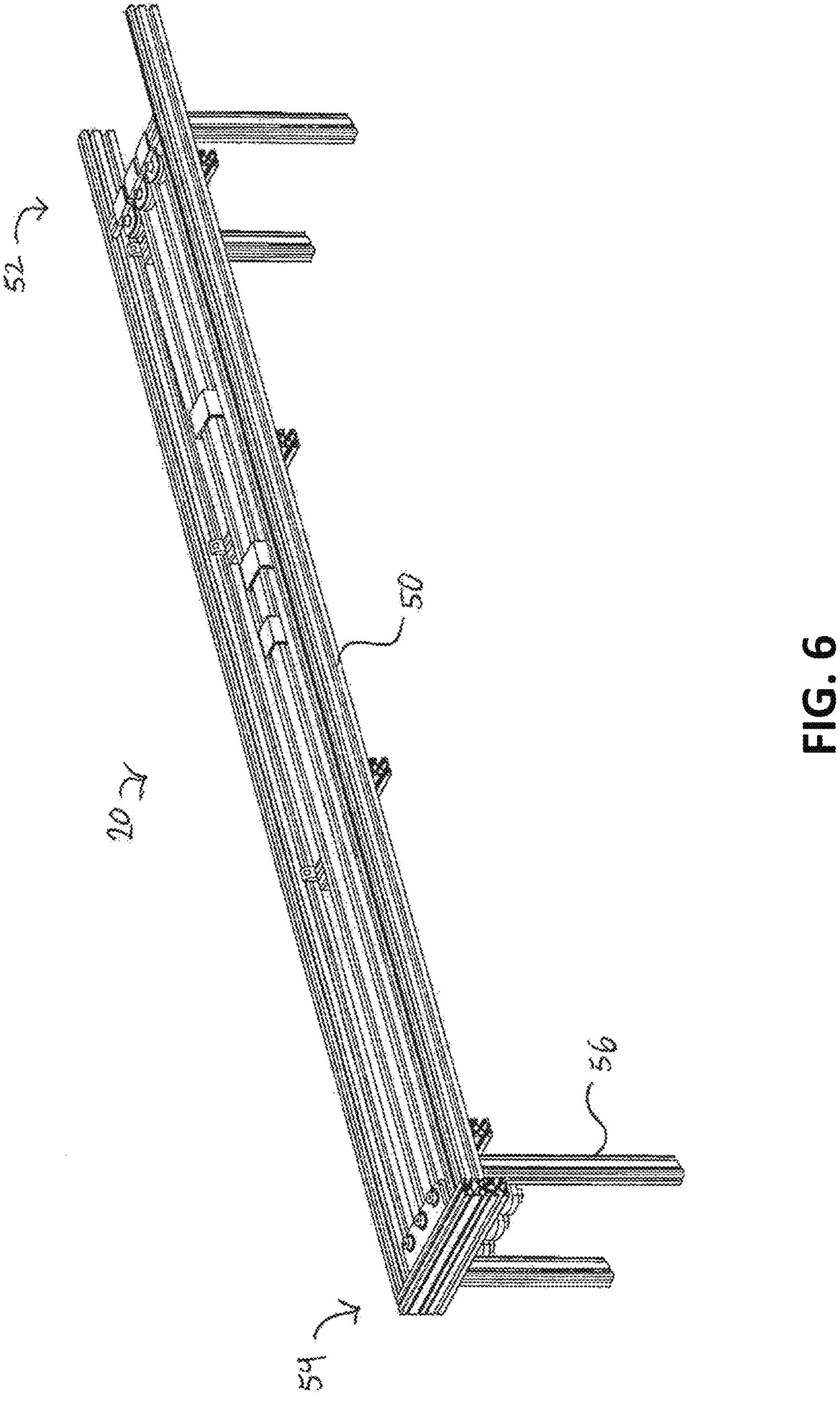
FIG. 6 is a perspective view of a support table.

Referring to FIG. 6, there is schematically illustrated one example of a low-profile linear drive support table 20. Support table 20 comprises an elongated frame 50 extending between a proximal end 52 and a distal end 54. At least one support table support 56 is provided to stabilize the support table 20 with respect to the patient (not illustrated). Support 56 may comprise one or more legs or preferably an articulating arm configured to allow movement and positioning of the frame 50 over or adjacent to the patient.

Figure 7:
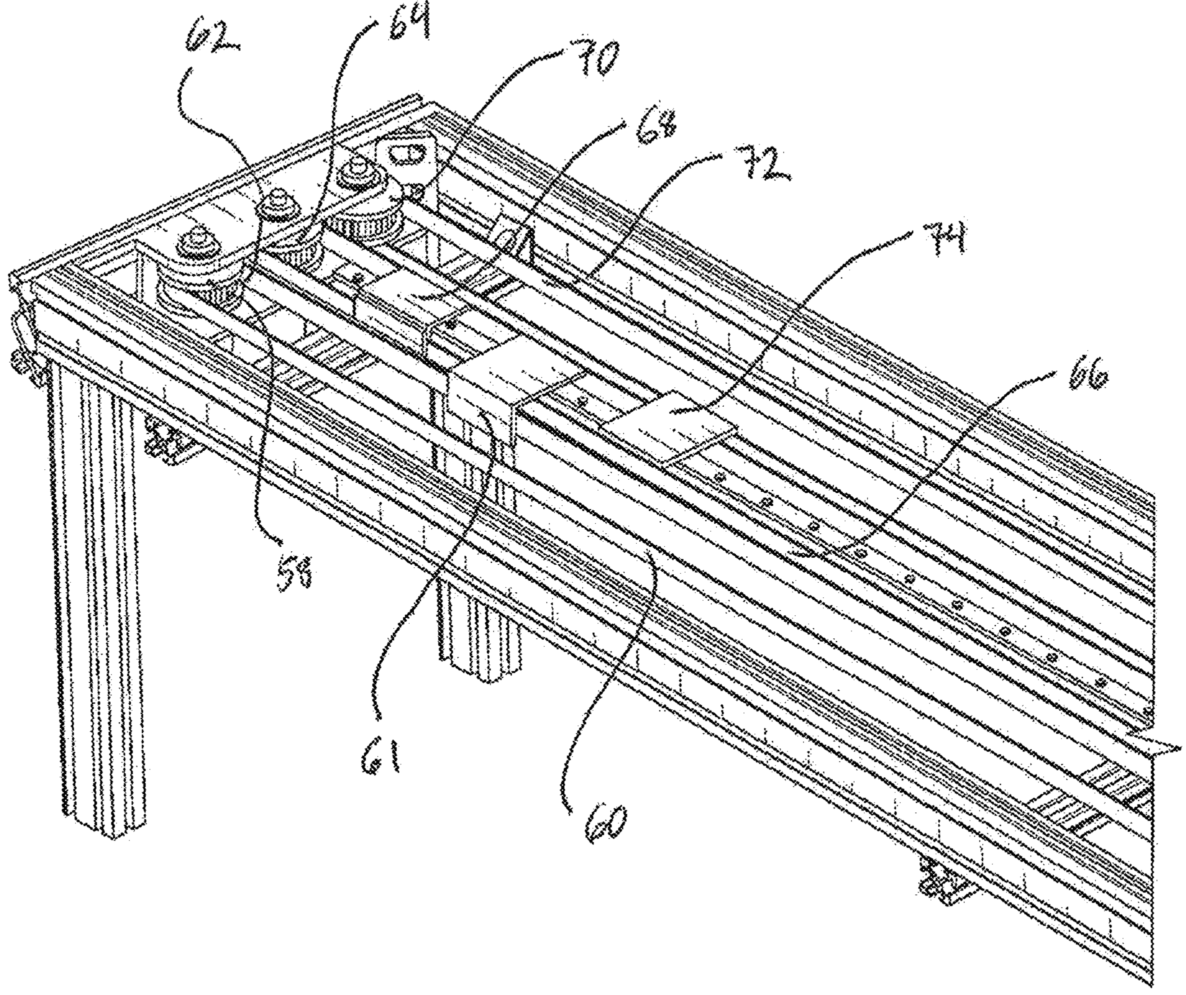
FIG. 7 is a close-up view of the motor drive end of a support table.

One example of a linear drive table 20 illustrated in FIG. 7 includes three distinct drives. However, two drives or four or more drives may be included depending upon the desired clinical performance. A first drive pulley 58 engages a first drive belt 60. A first carriage bracket 61 is secured to the first drive belt 60 such that rotation of the first drive pulley 58 causes rotation of the first drive belt 60 through an elongate closed loop path. The first carriage bracket 61 may be advanced in a proximal or distal direction along the longitudinal axis of the support table 20 depending upon the direction of rotation of the drive pully 58. In the illustrated implementation, the drive pulley 58 is provided with surface structures such as a plurality of drive pulley teeth 62 for engaging complementary teeth on the first drive belt 60.

A second drive pulley 64 may engage a second drive belt 66 configured to axially move a second carriage bracket 68 along an axial path on the support table 20. A third drive pulley 70 may be configured to drive a third drive belt 72, to advance a third carriage bracket 74 axially along the support table 20. Each of the carriage brackets may be provided with a drive magnet assembly discussed previously but not illustrated in FIG. 7, to form couplers for magnetically coupling to a corresponding driven magnet within the hub of an interventional device as has been discussed.

Figure 8:
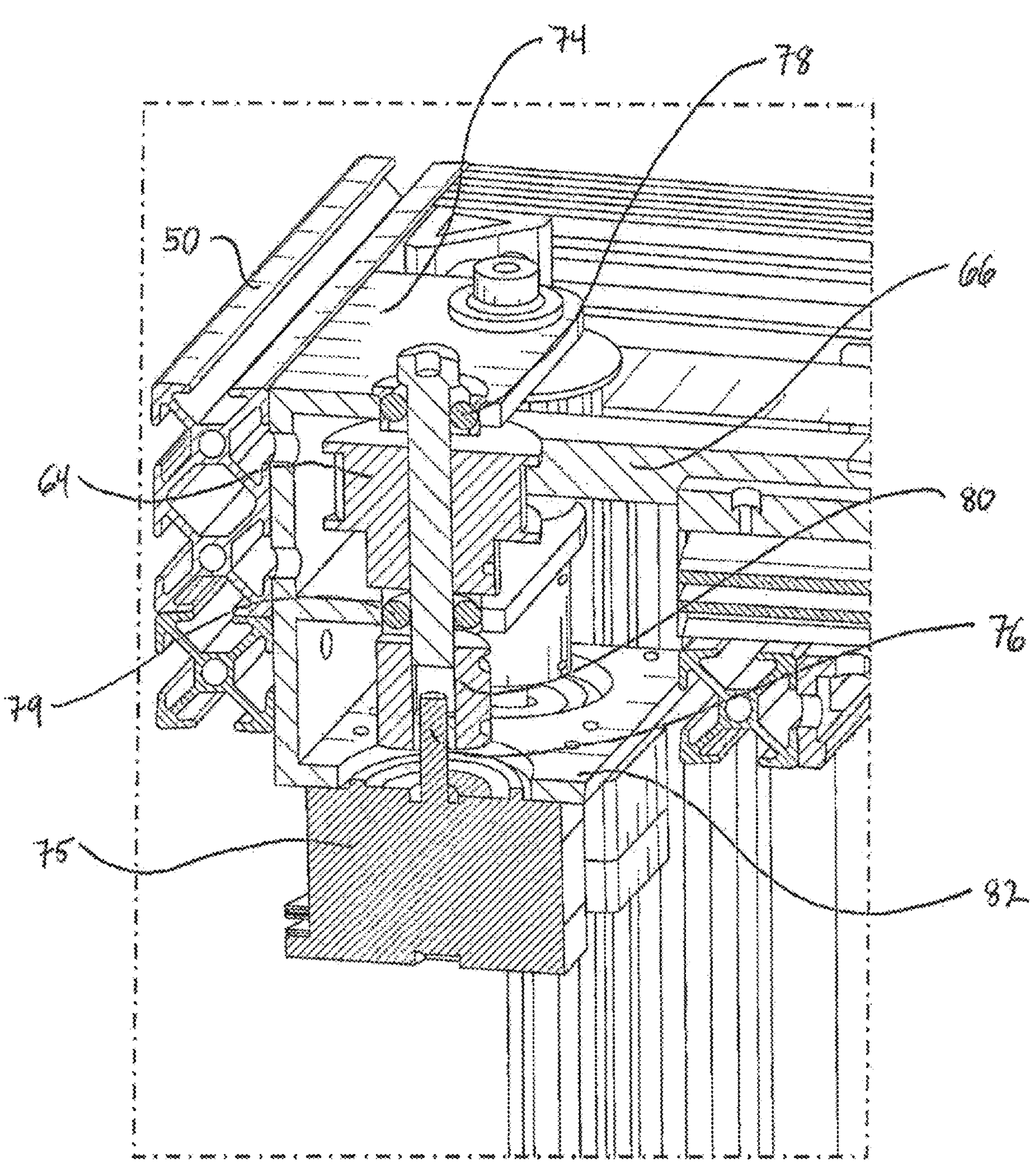
FIG. 8 is an elevational cross section through a motor and belt drive assembly.

A detail view of a drive system is shown schematically in FIG. 8. A drive support 74 may be carried by the frame 50 for supporting the drive assembly. The second drive pulley 64 is shown in elevational cross section as rotationally driven by a motor 75 via a rotatable shaft 76. The rotatable shaft 76 may be rotatably carried by the support 74 via a first bearing 78, a shaft coupling 80 and second bearing 79. Motor 75 may be stabilized by a motor bracket 82 connected to the drive support 74 and or the frame 50. The belt drive assemblies for the first drive belt 60 and third drive belt 72 maybe similarly constructed and are not further detailed herein.

Figure 9:
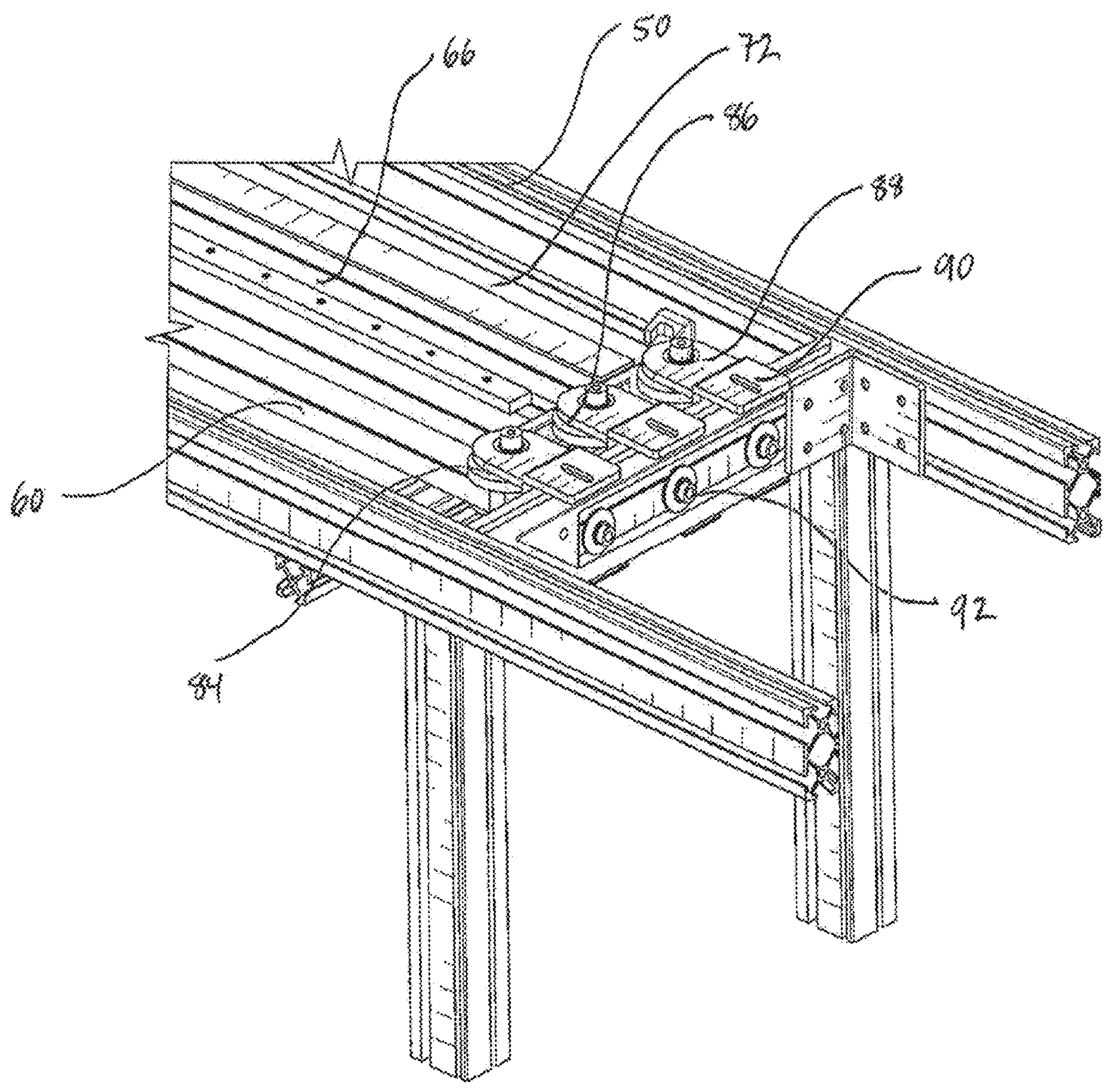
FIG. 9 is a close-up view of a pulley end of the support table.
Figure 10:
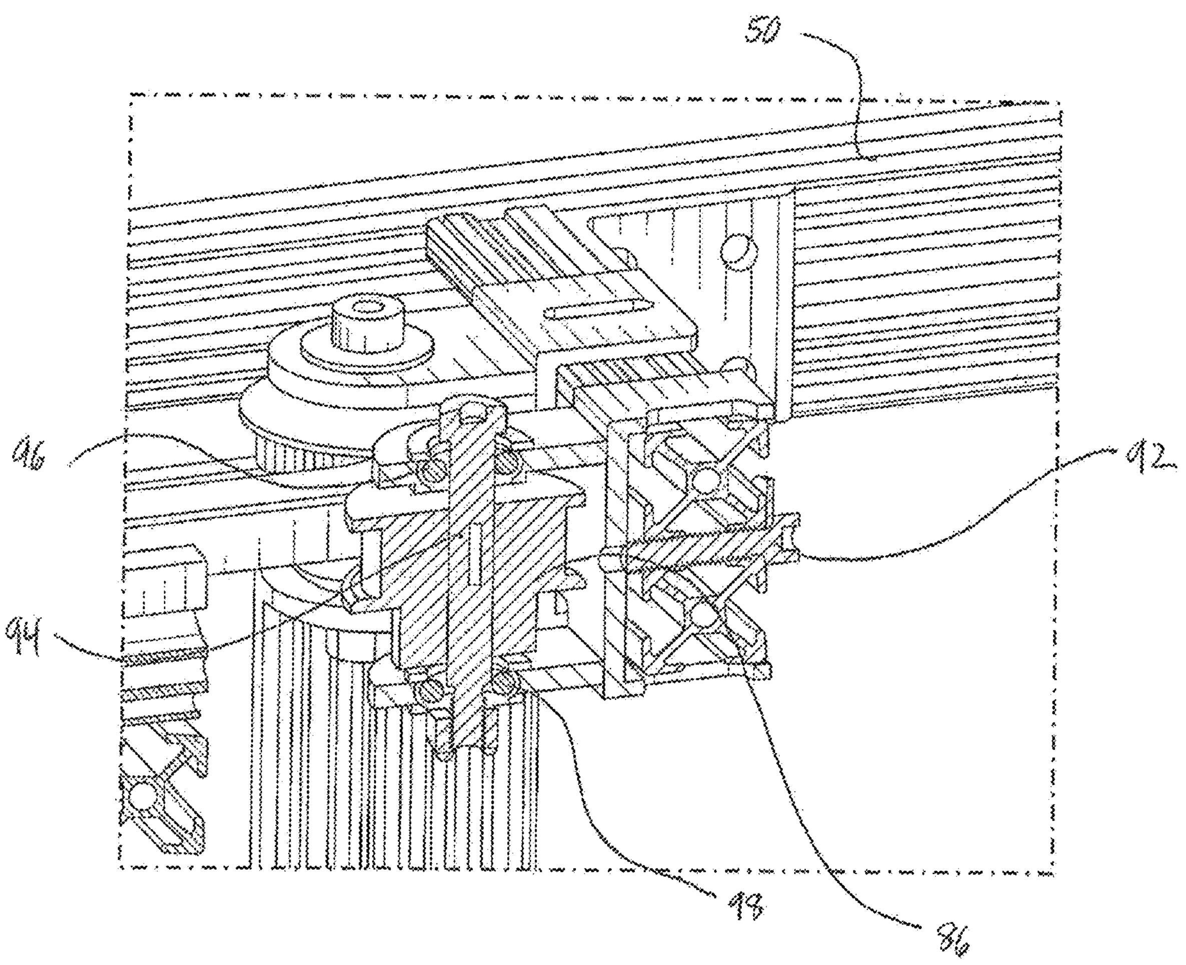
FIG. 10 is an elevational cross section through a belt pully.

Referring to FIGS. 9 and 10, each of the first second and third drive belts extends around a corresponding first idler pulley 84 second idler pulley 86 and third idler pulley 88. Each idler pulley may be provided with a corresponding tensioning bracket 90, configured to adjust the idler pulleys in a proximal or distal direction in order to adjust the tension of the respective belt. Each tensioning bracket 90 is therefore provided with a tensioning adjustment 92 such as a rotatable screw.

As seen in FIG. 10, the second idler pulley 86, for example, may be carried by a rotatable shaft 94, rotatably secured with respect to the mounting bracket by a first bearing 96 and second bearing 98.

Figure 11:
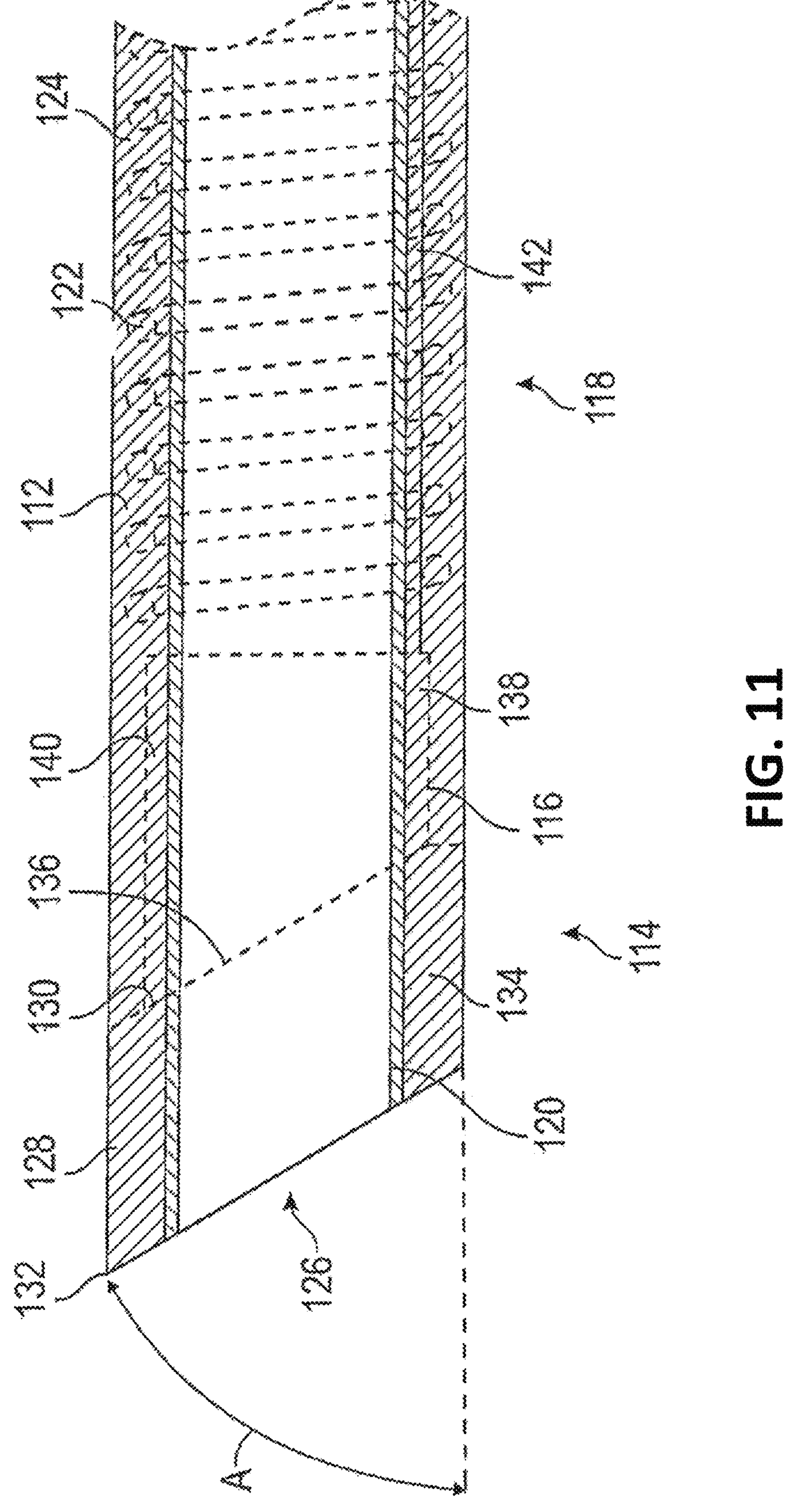
FIG. 11 is a side elevational cross-section through a distal portion of a catheter such as any of those shown in FIGS. 5A and 5B.

Any of the catheters illustrated, for example, in FIG. 5A, 5B or 11 generally comprise an elongate tubular body extending between a proximal end and a distal functional end. The length and diameter of the tubular body depends upon the desired application. For example, lengths in the area of from about 120 cm to about 140 cm or more are typical for use in femoral access percutaneous transluminal coronary applications. Intracranial or other applications may call for a different catheter shaft length depending upon the vascular access site.

Any of the catheters disclosed herein may be provided with an inclined distal tip. Referring to FIG. 11, distal catheter tip 110 comprises a tubular body 112 which includes an advance segment 114, a marker band 116 and a proximal segment 118. An inner tubular liner 120 may extend throughout the length of the distal catheter tip 110, and may comprise dip coated PTFE.

A reinforcing element 122 such as a braid or spring coil is embedded in an outer jacket 124 which may extend the entire length of the catheter.

The advance segment 114 terminates distally in an angled face 126, to provide a leading side wall portion 128 having a length measured between the distal end 130 of the marker band 116 and a distal tip 132. A trailing side wall portion 134 of the advance segment 114, has an axial length in the illustrated embodiment of approximately equal to the axial length of the leading side wall portion 128 as measured at approximately 180 degrees around the catheter from the leading side wall portion 128. The leading side wall portion 128 may have an axial length within the range of from about 0.1 mm to about 5 mm and generally within the range of from about 1 to 3 mm. The trailing side wall portion 134 may be equal to or at least about 0.1 or 0.5 or 1 mm or 2 mm or more shorter than the axial length of the leading side wall portion 128, depending upon the desired performance.

The angled face 126 inclines at an angle A within the range of from about 45 degrees to about 80 degrees from the longitudinal axis of the catheter. For certain implementations, the angle is within the range of from about 55 degrees to about 65 degrees from the longitudinal axis of the catheter. In one implementation the angle A is about 60 degrees. One consequence of an angle A of less than 90 degrees is an elongation of a major axis of the area of the distal port which increases the surface area of the port and may enhance clot aspiration or retention. Compared to the surface area of the circular port (angle A is 90 degrees), the area of the angled port is generally at least about 105%, and no more than about 130%, in some implementations within the range of from about 110% and about 125% and in one example is about 115% of the area of the corresponding circular port (angle A is 90 degrees).

In the illustrated embodiment, the axial length of the advance segment is substantially constant around the circumference of the catheter, so that the angled face 126 is approximately parallel to the distal surface 136 of the marker band 116. The marker band 116 has a proximal surface approximately transverse to the longitudinal axis of the catheter, producing a marker band 116 having a right trapezoid configuration in side elevational view. A short sidewall 138 is rotationally aligned with the trailing side wall portion 134, and has an axial length within the range of from about 0.2 mm to about 4 mm, and typically from about 0.5 mm to about 2 mm. An opposing long sidewall 140 is rotationally aligned with the leading side wall portion 128. Long sidewall 140 of the marker band 116 is generally at least about 10% or 20% longer than short sidewall 138 and may be at least about 50% or 70% or 90% or more longer than short sidewall 138, depending upon desired performance. Generally, the long sidewall 140 will have a length of at least about 0.5 mm or 1 mm and less than about 5 mm or 4 mm.

The marker band may be a continuous annular structure, or may have at least one and optionally two or three or more axially extending slits throughout its length. The slit may be located on the short sidewall 138 or the long sidewall 140 or in between, depending upon desired bending characteristics. The marker band may comprise any of a variety of radiopaque materials, such as a platinum/iridium alloy, with a wall thickness preferably no more than about 0.003 inches and in one implementation is about 0.001 inches.

The marker band zone of the assembled catheter may have a relatively high bending stiffness and high crush strength, such as at least about 50% or at least about 100% less than proximal segment 18 but generally no more than about 200% less than proximal segment 118. The high crush strength may provide radial support to the adjacent advance segment 114 and particularly to the leading side wall portion 128, to facilitate the functioning of distal tip 132 as an atraumatic bumper during transluminal advance and to resist collapse under vacuum. The proximal segment 118 preferably has a lower bending stiffness than the marker band zone, and the advance segment 114 preferably has even a lower bending stiffness and crush strength than the proximal segment 118.

The advance segment 114 may comprise a distal extension of the outer tubular jacket 124 and optionally the inner liner 120, without other internal supporting structures distally of the marker band 116. Outer jacket 124 may comprise extruded Tecothane. The advance segment 114 may have a bending stiffness and radial crush stiffness that is no more than about 50%, and in some implementations no more than about 25% or 15% or 5% or less than the corresponding value for the proximal segment 118.

The catheter may further comprise an axial tension element or support such as a ribbon or one or more filaments or fibers for increasing the tension resistance and/or influencing the bending characteristics in the distal zone. The tension support may comprise one or more axially extending mono strand or multi strand filaments 142. The one or more tension element 142 may be axially placed inside the catheter wall near the distal end of the catheter. The one or more tension element 142 may serve as a tension support and resist tip detachment or elongation of the catheter wall under tension (e.g., when the catheter is being proximally retracted through a kinked outer catheter or tortuous or narrowed vasculature).

At least one of the one or more tension element 142 may proximally extend along the length of the catheter wall from within about 1.0 cm from the distal end of the catheter to less than about 10 cm from the distal end of the catheter, less than about 20 cm from the distal end of the catheter, less than about 30 cm from the distal end of the catheter, less than about 40 cm from the distal end of the catheter, or less than about 50 cm from the distal end of the catheter.

The one or more tension element 142 may have a length greater than or equal to about 40 cm, greater than or equal to about 30 cm, greater than or equal to about 20 cm, greater than or equal to about 10 cm, or greater than or equal to about 5 cm.

At least one of the one or more tension element 142 may extend at least about the most distal 50 cm of the length of the catheter, at least about the most distal 40 cm of the length of the catheter, at least about the most distal 30 cm or 20 cm or 10 cm of the length of the catheter.

In some implementations, the tension element extends proximally from the distal end of the catheter along the length of the coil 24 and ends proximally within about 5 cm or 2 cm or less either side of a transition between a distal coil and a proximal braid. The tension element may end at the transition without overlapping with the braid.

The one or more tension element 142 may be placed near or radially outside the inner liner 120. The one or more tension element 142 may be placed near or radially inside the braid and/or the coil. The one or more tension element 142 may be carried between the inner liner 120 and the helical coil, and may be secured to the inner liner or other underlying surface by an adhesive prior to addition of the next outer adjacent layer such as the coil. Preferably, the tension element 142 is secured to the marker band 116 such as by adhesives or by mechanical interference. In one implementation, the tension element 142 extends distally beyond the marker band on a first (e.g., inside) surface of the marker band, then wraps around the distal end of the marker band and extends along a second (e.g., outside) surface in either or both a proximal inclined or circumferential direction to wrap completely around the marker band.

When more than one tension element 142 or filament bundles are spaced circumferentially apart in the catheter wall, the tension elements 142 may be placed in a radially symmetrical manner. For example, the angle between two tension elements 142 with respect to the radial center of the catheter may be about 180 degrees. Alternatively, depending on desired clinical performances (e.g., flexibility, trackability), the tension elements 142 may be placed in a radially asymmetrical manner. The angle between any two tension elements 142 with respect to the radial center of the catheter may be less than about 180 degrees, less than or equal to about 165 degrees, less than or equal to about 135 degrees, less than or equal to about 120 degrees, less than or equal to about 90 degrees, less than or equal to about 45 degrees or, less than or equal to about 15 degrees.

The one or more tension element 142 may comprise materials such as Vectran, Kevlar, Polyester, Meta-Para-Aramide, or any combinations thereof. At least one of the one or more tension element 142 may comprise a single fiber or a multi-fiber bundle, and the fiber or bundle may have a round or rectangular (e.g. ribbon) cross section. The terms fiber or filament do not convey composition, and they may comprise any of a variety of high tensile strength polymers, metals or alloys depending upon design considerations such as the desired tensile failure limit and wall thickness. The cross-sectional dimension of the one or more tension element 142, as measured in the radial direction, may be no more than about 2%, 5%, 8%, 15%, or 20% of that of the catheter 10.

The cross-sectional dimension of the one or more tension element 142, as measured in the radial direction, may be no more than about 0.001 inches, no more than about 0.002 inches, no more than about 0.004 inches, no more than about 0.006 inches, no more than about 0.008 inches, or about 0.015 inches.

The one or more tension element 142 may increase the tensile strength of the distal zone of the catheter before failure under tension (e.g. marker band detachment) to at least about 1 pound, at least about 2 pounds, at least about 3 pounds, at least about 4 pounds, at least about 5 pounds, at least about 6 pounds, at least about 7 pounds, at least about 8 pounds, or at least about 10 pounds or more.

Figure 12A:
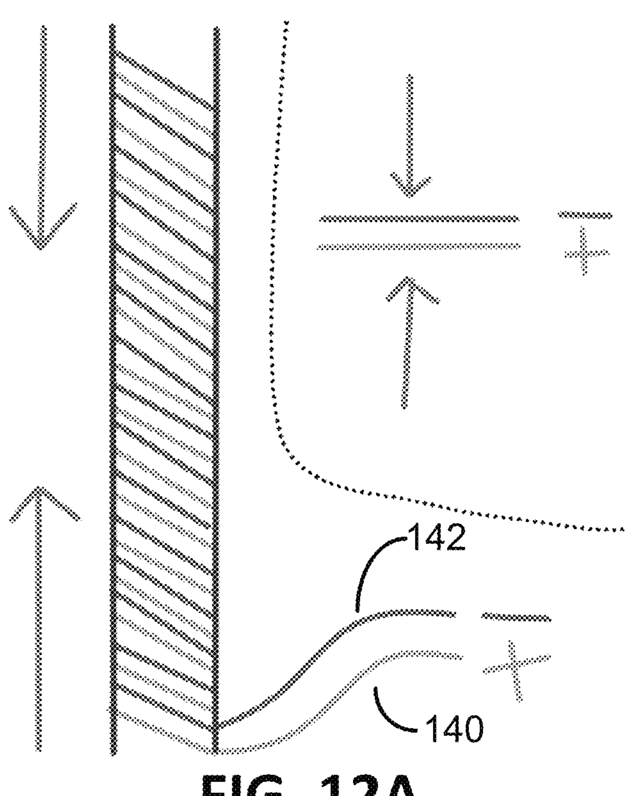
FIGS. 12A and 12B schematically illustrate a force sensor integrated into the sidewall of the catheter.

Any of a variety of sensors may be provided on any of the catheters, hubs, carriages, or table, depending upon the desired data. For example, in some implementations of the invention, it may be desirable to measure axial tension or compression force applied to the catheter such as along a force sensing zone. The distal end of the catheter would be built with a similar construction as illustrated in FIG. 11, with a helical coil distal section. But instead of using a single helical coil of nitinol wire, a first conductor 140 and second conductor 142 are wrapped into intertwined helical coils and electrically isolated from each other such as by the plastic/resin of the tubular body. See FIG. 12A. Each coil is in electrical communication with the proximal hub by a unique electrical conductor such as a conductive trace or proximal extension of the wire.

Figure 12B:
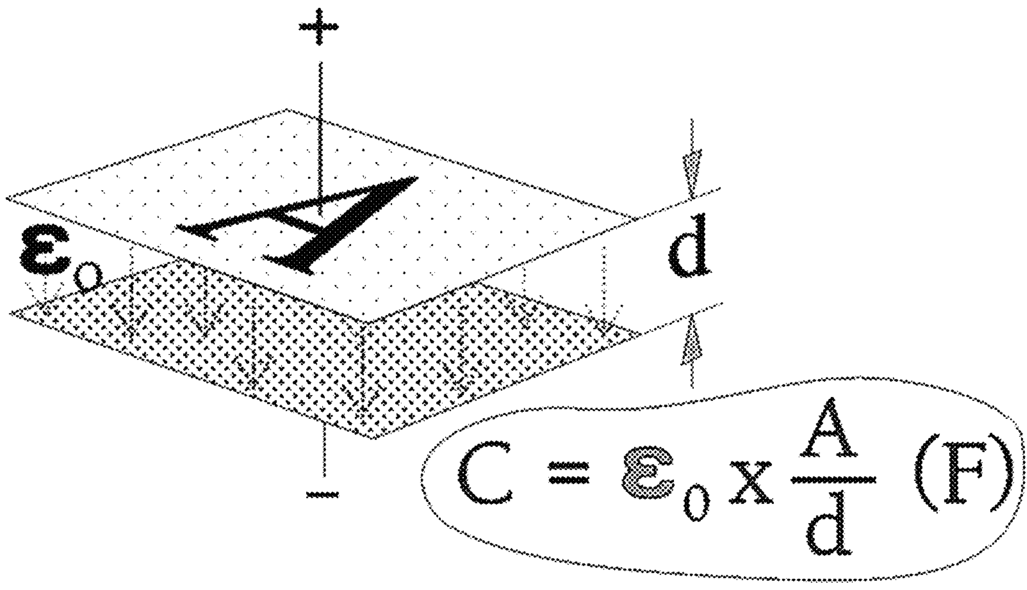

This construction of double, electrically isolated helical coils creates a capacitor. This is roughly equivalent to two plates of nitinol with a plastic layer between them, illustrated in FIG. 12B. The capacitance is inversely proportional to the distance between wires. The only variable that would be changing would be d, the distance between the plates. If an axial compressive force is applied to the catheter, the wires 140 and 142 will move closer together, thus increasing the capacitance. If an axial tensile force is applied, the wires will get further apart, decreasing the capacitance. This capacitance can be measured at the proximal end of the catheter, giving a measurement of the force at the helical capacitor. Although referred to as a capacitor, this sensor is measuring the electrical interaction between the two coils of wire. There may be a measurable change in inductance or other resulting change due to applied axial forces.

At least a first helical capacitor may have at least one or five or ten or more complete revolutions of each wire. A capacitor may be located within the distal most 5 or 10 or 20 cm of the catheter body to sense forces experienced at the distal end. At least a second capacitor may be provided within the proximal most 5 or 10 or 20 cm of the catheter body, to sense forces experienced at the proximal end of the catheter.

It may also be desirable to measure elastic forces across the magnetic coupling between the hub and corresponding carriage, using the natural springiness (compliance) of the magnetic coupling to measure the force applied to the hub. The magnetic coupling between the hubs and carriages creates a spring. When a force is applied to the hub, the hub will move a small amount relative to the carriage. See FIG. 13A. In robotics, this is called a series elastic actuator. This property can be used to measure the force applied from the carriage to the hub. To measure the force, the relative distance between the hub and the carriage (dx shown in FIG. 13A) is determined and characterize some effective spring constant k between the two components. See FIG. 13B.

The relative distance could be measured in multiple different ways.

One method for measuring the relative distance between the puck and carriage is a magnetic sensor (e.g., a Hall effect Sensor between hub and carriage). A magnet is mounted to either the hub or carriage, and a corresponding magnetic sensor is mounted on the other device (carriage or hub). The magnetic sensor might be a hall effect sensor, a magnetoresistive sensor, or another type of magnetic field sensor. Generally, multiple sensors may be used to increase the reliability of the measurement. This reduces noise and reduces interference from external magnetic fields.

Other non-contact distance sensors can also be used. These include optical sensors, inductance sensors, and capacitance sensors. Optical sensors would preferably be configured in a manner that avoids accumulation of blood or other fluid in the interface between the hubs carriages.

The magnetic coupling between the hub and the carriage has a break away threshold which may be about 300 grams or 1000 grams or more. The processor can be configured to compare the axial force applied to the catheter to a preset axial trigger force which if applied to the catheter is perceived to create a risk to the patient. If the trigger force is reached, the processor may be configured to generate a response such as a visual, auditory or tactile feedback to the physician, and/or intervene and shut down further advance of the catheter until a reset is accomplished. An override feature may be provided so the physician can elect to continue to advance the catheter at forces higher than the trigger force, in a situation where the physician believes the incremental force is warranted.

Force and or torque sensing fiber optics (e.g., Fiber Bragg Grating (FBG) sensors) may be built into the catheter side wall to measure the force and/or torque at various locations along the shaft of a catheter or alternatively may be integrated into a guidewire. The fiber measures axial strain, which can be converted into axial force or torque (when wound helically). At least a first FBG sensor can be integrated into a distal sensing zone, proximal sensing zone and/or intermediate sensing zone on the catheter or guidewire, to measure force and or torque in the vicinity of the sensor.

It may also be desirable to understand the three dimensional configuration of the catheter or guidewire during and/or following transvascular placement. Shape sensing fiber optics such as an array of FBG fibers to sense the shape of catheters and guidewires. By using multiple force sensing fibers that are a known distance from each other, the shape along the length of the catheter/guidewire can be determined.

A resistive strain gauge may be integrated into the body of the catheter or guidewire to measure force or torque. Such as at the distal tip and/or proximal end of the device.

Absolute position of the hubs (and corresponding catheters) along the length of the table may be determined in a variety of ways. For example, a non-contact magnetic sensor may be configured to directly measure the position of the hubs through the sterile barrier. The same type of sensor can also be configured to measure the position of the carriages. Each hub may have at least one magnet attached to it. The robotic table would have a linear array of corresponding magnetic sensors going the entire length of the table. A processor can be configured to determine the location of the magnet along the length of the linear sensor array, and display axial position information to the physician.

The foregoing may alternatively be accomplished using a non-contact inductive sensor to directly measure the position of the pucks through the sterile barrier. Each hub or carriage may be provided with an inductive "target" in it. The robotic table may be provided with an inductive sensing array over the entire working length of the table. As a further alternative, an absolute linear encoder may be used to directly measure the linear position of the hubs or carriages. The encoder could use any of a variety of different technologies, including optical, magnetic, inductive, and capacitive methods.

In one implementation, a passive (no electrical connections) target coil may be carried by each hub. A linear printed circuit board may run the entire working length of the table (e.g., at least about 5' or 6') configured to ping an interrogator signal which stimulates a return signal from the passive coil. The PCB is configured to identify the return signal and its location.

Axial position of the carriages may be determined using a multi-turn rotary encoder to measure the rotational position of the pulley, which directly correlates to the linear position of the carriage. Direct measurement of the location of the carriage may alternatively be accomplished by recording the number of steps commanded to the stepper motor to measure the rotational position of the pulley, which directly correlates to the linear position of the carriage.

The location of the catheters and guidewires within the anatomy may also be determined by processing the fluoroscopic image with machine vision, such as to determine the distal tip position, distal tip orientation, and/or guidewire shape. The processing may be done in real time to provide position/orientation data at up to 30 hz (the max speed of the fluoro), although this technique would only provide data while the fluoro is turned on.

Proximal torque applied to the catheter or guidewire shaft may be determined using a dual encoder torque sensor. Referring to FIG. 14, a first encoder 144 and a second encoder 146 may be spaced axially apart along the shaft 148, for measuring the difference in angle over a length of flexible catheter/tube. The difference in angle is interpolated as a torque, since the catheter/tube has a known torsional stiffness. As torque is applied to the shaft, the slightly flexible portion of the shaft will twist. The difference between the angles measured by the encoders ($d\theta$) tells us the torque. $T=k*d\theta$, where k is the torsional stiffness.

Confirming the absence of bubbles in fluid lines may also be accomplished using bubble sensors, particularly where the physician is remote from the patient. This may be accomplished using a non-contact ultrasonic sensor that measures the intensity and doppler shift of the reflected ultrasound through the sidewall of fluid tubing to detect bubbles and measure fluid flow rate or fluid level. An ultrasonic or optical sensor may be positioned adjacent an incoming fluid flow path within the hub, or in a supply line leading to the hub. To detect the presence of air bubbles in the infusion line (that is formed of ultrasonically or optically transmissive material) the sensor may include a signal source on a first side of the flow path and a receiver on a second side of the flow path to measure transmission through the liquid passing through the tube to detect bubbles. Alternatively, a reflected ultrasound signal may be detected from the same side of the flow path as the source due to the relatively high echogenicity of bubbles.

Preferably a bubble removal system is automatically activated upon detection of in line bubbles. A processor may be configured to activate a valve positioned in the flow path downstream of the bubble detector, upon the detection of bubbles. The valve diverts a column of fluid out of the flow path to the patient and into a reservoir. Once bubbles are no longer detected in the flow path and after the volume of fluid in the flow path between the detector and the valve has passed through the valve, the valve may be activated to reconnect the source of fluid with the patient through the flow path.

Figure 15:
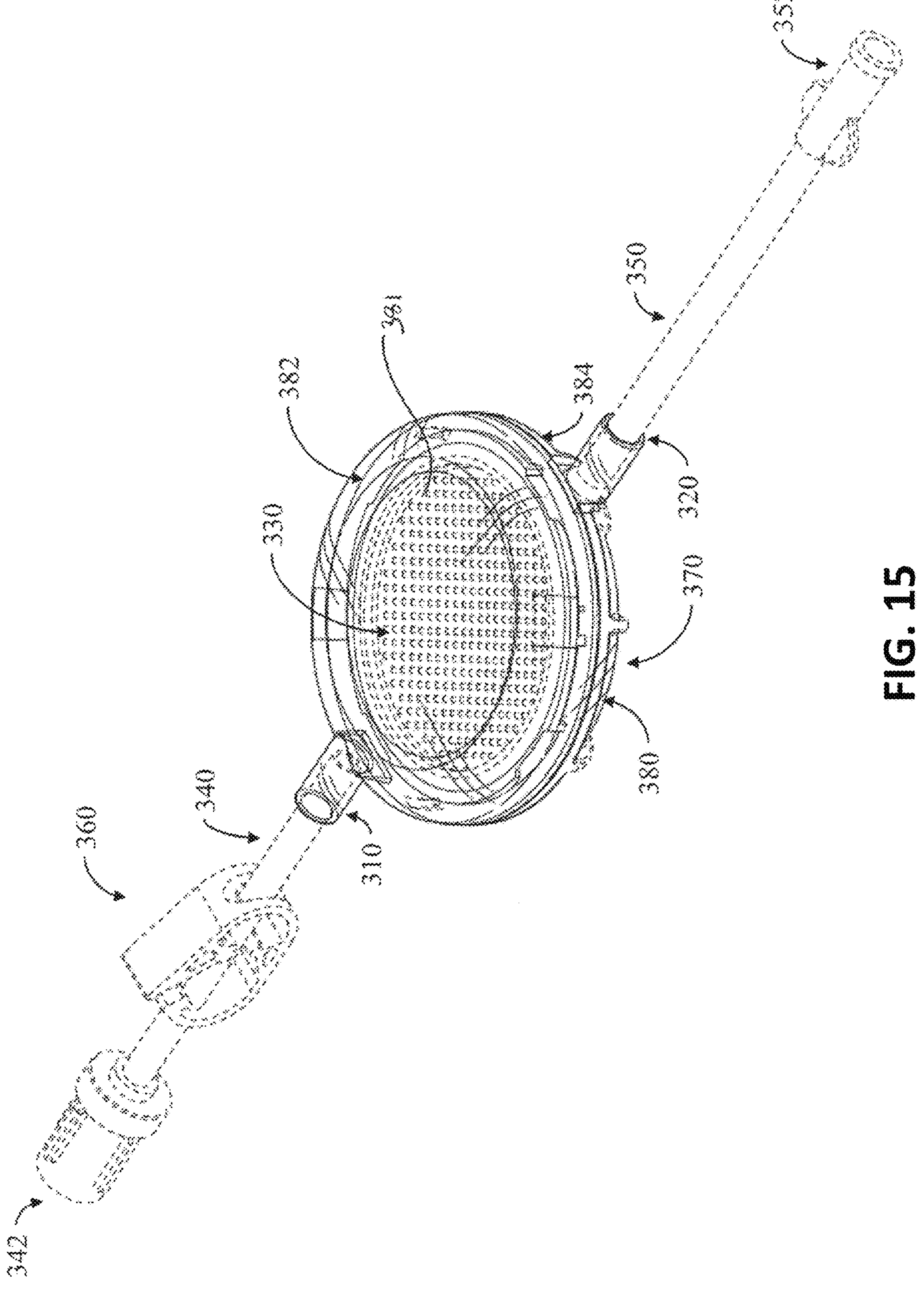
FIG. 15 illustrates a clot capture and visualization device that can be integrated into a hub and/or connected to an aspiration line.

It may additionally be desirable for the physician to be able to view aspirated clot at a location within the sterile field and preferably as close to the patient as practical for fluid management purposes. This may be accomplished by providing a clot retrieval device mounted on the hub, or in an aspiration line leading away from the hub in the direction of the pump. Referring to FIG. 15, one example of a clot retrieval device 370 can include a body 380 enclosing a chamber 381 which communicates with a first port 310 and a second port 320. In some examples, the body 380 can include a flush port (not illustrated) that is configured to allow the injection of saline or other fluid into the chamber 381 to improve clot visualization once it is trapped in the filter 330.

In some embodiments, the body 380 includes a housing having a top portion 382 and a bottom portion 384. The body 380 may include a filter 330 positioned in the chamber 381 between the top portion 382, and the bottom portion 384. In some examples, the first port 310 is configured to connect to a first end of a first tube 340 that is fluidly connected to a proximal end of an aspiration catheter. In an embodiment that is configured to be connected downstream from the hub, the first tube 340 includes a connector 342 positioned at a second end of the first tube 340 that is configured to engage or mate with a corresponding connector on or in communication with the hub. The first port 310 directly communicates with the chamber on the upstream (e.g., top side) of the filter, and the second port 320 directly communicates with the chamber on the downstream (e.g., bottom side) of the filter to facilitate direct visualization of material caught on the upstream side of the filter. In an implementation configured for remote operation, any of a variety of sensors may be provided to detect clot passing through the aspiration line and/or trapped in the filter, such as an optical sensor, ultrasound sensor or others known in the art.

In some embodiments, the second port 320 is configured to connect to a first end of a second tube 350 that is fluidly connected to an aspiration source (e.g., a pump). In some embodiments, the second tube 350 includes a connector 352 positioned at a second end of the second tube 350 that is configured to engage or mate with a corresponding connector on the pump. In some examples, the system 300 can include a clamp 360. The clamp 360 can be positioned over the first tube 340 to allow the user to engage the clamp and provide flow control over the clot retrieval device 370.

The body 380 can have a top surface spaced apart from a bottom surface by a tubular side wall. In the illustrated implementation, the top and bottom surfaces are substantially circular, and spaced apart by a cylindrical side wall having a diameter that is at least about three times, or five times or more than the axial length (transverse to the top and bottom surfaces) of the side wall, to produce a generally disc shaped housing. Preferably at least a portion of the top wall is optically transparent to improve clot visualization once it is trapped in the clot retrieval device 370. Additional details may be found in U.S. Patent Application No. 63/256,743, the entirety of each of which is hereby incorporated by reference herein.

The foregoing represents certain specific implementations of a drive table and associated catheters. a wide variety of different drive table constructions can be made, for supporting and axially advancing and retracting two or three or four or more drive magnet assemblies to robotically drive interventional devices, as will be appreciated by those of skill in the art in view of the disclosure herein.

EXAMPLE EMBODIMENTS

A supra-aortic vessel access robotic control system comprising one or more of the following:

- a guidewire hub configured to adjust each of an axial position and a rotational position of a guidewire;
- a guide catheter hub configured to adjust a guide catheter in an axial direction; and
- a second catheter hub configured to adjust each of an axial position and a rotational position of a second catheter, and also to laterally deflect a distal deflection zone of the second catheter.

A control system as described in any embodiment herein, wherein the second catheter is an aspiration catheter.

A control system as described in any embodiment herein, wherein the second catheter is an embolic deployment catheter.

A control system as described in any embodiment herein, wherein the second catheter is configured to deploy embolic coils.

A control system as described in any embodiment herein, wherein the second catheter is a stent deployment catheter.

A control system as described in any embodiment herein, wherein the second catheter is configured to deploy a stentriever.

A control system as described in any embodiment herein, wherein the second catheter is a flow diverter deployment catheter.

A control system as described in any embodiment herein, wherein the second catheter is a diagnostic angiographic catheter.

A control system as described in any embodiment herein, further comprising a driven magnet on the guidewire hub configured to cooperate with a drive magnet such that the driven magnet moves in response to movement of the drive magnet.

A control system as described in any embodiment herein, wherein the drive magnet is axially movably carried by a support table.

A control system as described in any embodiment herein, wherein the drive magnet moves outside of the sterile field separated from the driven magnet by a barrier, and the driven magnet is within the sterile field.

A control system as described in any embodiment herein, wherein the barrier comprises a polymer membrane.

A control system as described in any embodiment herein, further comprising a control console located remotely from the support table.

A control system as described in any embodiment herein, wherein the position of the driven magnet is movable in response to manipulation of a guidewire drive control on the console.

A control system as described in any embodiment herein, further comprising a processor for controlling the position of the driven magnet, and the processor is in wired communication with the control console.

A control system as described in any embodiment herein, further comprising a processor for controlling the position of the driven magnet, and the processor is in wireless communication with the control console.

A control system as described in any embodiment herein, wherein the driven magnet will remain engaged with the drive magnet until an applied force reaches a disruption force threshold above which the driven magnet will become decoupled from the drive magnet.

A control system as described in any embodiment herein, wherein the disruption force threshold is at least about 300 grams.

A control system as described in any embodiment herein, further comprising a sensor configured to measure the applied force between the driven magnet and the drive magnet.

A control system as described in any embodiment herein, further comprising a processor configured to compare an applied force to the disruption force threshold.

A control system as described in any embodiment herein, wherein the processor is configured to adjust a rate of movement of the drive magnet when the applied force reaches a preset value below the disruption force threshold.

A control system as described in any embodiment herein, wherein the sensor comprises a strain gauge.

A control system as described in any embodiment herein, wherein the processor is configured to halt movement of the drive magnet when the applied force reaches a preset value below the disruption force threshold.

A robotically driven interventional device comprising one or more of the following:

- an elongate, flexible body, having a proximal end and a distal end;
- a hub on the proximal end
- at least one rotatable roller on a first surface of the hub; and
- at least one magnet on the first surface of the hub.

A robotically driven interventional device as described in any embodiment herein, wherein the roller extends further away from the first surface than the magnet.

A robotically driven interventional device as described in any embodiment herein, further comprising at least a second roller.

A robotically driven interventional device as described in any embodiment herein, further comprising a rotational drive within the hub, for rotating the interventional device with respect to the hub.

A robotically driven interventional device as described in any embodiment herein, further comprising a retraction mechanism in the hub, for proximally retracting a pull element extending through the interventional device.

A robotically driven interventional device as described in any embodiment herein, wherein the pull element comprises a pull wire.

A robotically driven interventional device as described in any embodiment herein, wherein the pull element comprises a pull tube.

A robotically driven interventional device as described in any embodiment herein, wherein a shape of a portion of the tubular body changes in response to proximal retraction of the pull element.

A robotically driven interventional device as described in any embodiment herein, wherein a stiffness characteristic of a portion of the tubular body changes in response to proximal retraction of the pull element.

A robotically driven interventional device as described in any embodiment herein, further comprising a sensor on the elongate flexible body.

A robotically driven interventional device as described in any embodiment herein, wherein the sensor comprises an axial force sensor.

A robotically driven interventional device as described in any embodiment herein, wherein a distal portion of the flexible body includes at least a first electrical conductor spaced axially apart from and insulated from a second electrical conductor.

A robotically driven interventional device as described in any embodiment herein, wherein first electrical conductor and second electrical conductor are adjacent helical windings of conductive wire.

A robotically driven interventional device as described in any embodiment herein, wherein the sensor comprises an oxygen sensor.

A robotically driven interventional device as described in any embodiment herein, wherein the sensor comprises a catheter shape sensor.

A robotically driven interventional device as described in any embodiment herein, wherein the sensor comprises a catheter position sensor.

A robotically driven interventional device as described in any embodiment herein, wherein the flexible body comprises a guide catheter.

A robotically driven interventional device as described in any embodiment herein, wherein the flexible body comprises a guidewire.

A robotically driven interventional device as described in any embodiment herein, wherein the flexible body comprises an access catheter.

A robotically driven interventional device as described in any embodiment herein, wherein the flexible body comprises an aspiration catheter.

A robotically driven interventional device as described in any embodiment herein, comprising a fiber bragg grating sensor.

A robotically driven interventional device as described in any embodiment herein, further comprising a clot filter in fluid communication with the hub.

A robotically driven interventional device as described in any embodiment herein, wherein the clot filter is carried by the hub.

A robotically driven interventional device as described in any embodiment herein, wherein the clot filter has a transparent side wall to permit visual inspection of captured clot.

A robotically driven interventional device as described in any embodiment herein, further comprising a bubble detector in fluid communication with a flow path through the hub.

A robotically driven interventional device as described in any embodiment herein, wherein the bubble detector is carried by the hub.

A robotically driven interventional device as described in any embodiment herein, further comprising a valve in the flow path, and a processor configured to adjust the valve in response to detection of bubbles in the flow path.

A robotically driven interventional device as described in any embodiment herein, wherein bubbles are diverted out of the flow path in response to adjustment of the valve.

A sterile packaging assembly for transporting interventional devices to a robotic surgery site comprising one or more of the following:

- a sterile barrier having a hub support portion and configured to enclose a sterile volume; and
- at least a first interventional device within the sterile volume, the first interventional device including a hub and an elongate flexible body, the hub including at least one magnet and at least one roller configured to roll on the hub support portion.

A sterile packaging assembly as described in any embodiment herein, wherein the hub support portion is configured to reside on a support table adjacent a patient, with an upper surface of the hub support portion within a sterile field and a lower surface of the hub support portion outside of the sterile field.

A sterile packaging assembly as described in any embodiment herein, wherein the hub support portion is substantially horizontal when residing on the support table.

A sterile packaging assembly as described in any embodiment herein, wherein the hub support portion is inclined relative to a horizontal plane when residing on the support table.

A sterile packaging assembly as described in any embodiment herein, wherein the hub further comprises at least one fluid injection port.

A sterile packaging assembly as described in any embodiment herein, wherein the hub further comprises a wireless RF transceiver.

A sterile packaging assembly as described in any embodiment herein, further comprising a visual indicator on the hub, for indicating the presence of a clot.

A sterile packaging assembly as described in any embodiment herein, wherein the visual indicator comprises a clot collection chamber having a transparent window.

A sterile packaging assembly as described in any embodiment herein, further comprising a filter in the clot chamber.

A sterile packaging assembly as described in any embodiment herein, further comprising a sensor for detecting the presence of a clot.

A sterile packaging assembly as described in any embodiment herein, wherein the sensor comprises a pressure sensor.

A sterile packaging assembly as described in any embodiment herein, wherein the sensor comprises an optical sensor.

A sterile packaging assembly as described in any embodiment herein, wherein the hub support portion comprises an elongate polymeric membrane having a longitudinal axis.

A sterile packaging assembly as described in any embodiment herein, wherein the sterile barrier additionally comprises at least a first storage tray adjacent the hub support portion.

A sterile packaging assembly as described in any embodiment herein, comprising a first storage tray and a second storage tray adjacent the hub support portion.

A sterile packaging assembly as described in any embodiment herein, wherein the first storage tray is on a first side of the hub support portion, and the second storage tray is on a second side of the hub support portion.

A sterile packaging assembly as described in any embodiment herein, comprising a first storage tray and a second storage tray adjacent the hub support portion.

A sterile packaging assembly as described in any embodiment herein, wherein the first interventional device is contained within the first storage tray.

A sterile packaging assembly as described in any embodiment herein, wherein the first interventional device is a guide catheter.

A sterile packaging assembly as described in any embodiment herein, wherein the first interventional device is an access catheter.

A sterile packaging assembly as described in any embodiment herein, wherein the first interventional device is a guidewire.

A sterile packaging assembly as described in any embodiment herein, wherein the first interventional device is an aspiration catheter.

A sterile packaging assembly as described in any embodiment herein, comprising a supra-aortic vessel access assembly in the first storage tray.

A sterile packaging assembly as described in any embodiment herein, wherein the access assembly comprises a guidewire, an access catheter and a guide catheter.

A sterile packaging assembly as described in any embodiment herein, further comprising a procedure assembly within the sterile volume.

A sterile packaging assembly as described in any embodiment herein, wherein the procedure assembly comprises a guidewire and an aspiration catheter.

A sterile packaging assembly as described in any embodiment herein, wherein the procedure assembly is carried in a second storage tray.

A sterile packaging assembly as described in any embodiment herein, wherein the sterile barrier is magnetically permeable.

A sterile packaging assembly as described in any embodiment herein, wherein the sterile barrier is fluid impermeable.

A sterile packaging assembly as described in any embodiment herein, wherein the sterile barrier is radiofrequency permeable.

A sterile packaging assembly as described in any embodiment herein, wherein the sterile barrier is impermeable to microorganisms.

A sterile packaging assembly as described in any embodiment herein, wherein the sterile barrier is translucent.

A sterile packaging assembly as described in any embodiment herein, wherein the sterile barrier is transparent.

A sterile packaging assembly as described in any embodiment herein, wherein the hub support portion has a convex curvature such that fluid is configured to flow away from the hub support portion.

A sterile packaging assembly as described in any embodiment herein, wherein the hub support portion has a longitudinal axis and a transverse axis and the hub support portion is convex in an upward direction in the transverse axis.

A sterile packaging assembly as described in any embodiment herein, wherein the sterile barrier is contained within an outer packaging.

A sterile packaging assembly as described in any embodiment herein, wherein the sterile barrier comprises a non-compliant polymer.

A sterile packaging assembly as described in any embodiment herein, wherein the non-compliant polymer comprises Polyethylene terephthalate (PET) or a thermoplastic polyurethane.

A sterile packaging assembly as described in any embodiment herein, wherein the sterile barrier further comprises a removable cover portion that cooperates with the hub support portion to define the sterile volume.

A sterile packaging assembly as described in any embodiment herein, wherein the hub is releasably coupled to the hub support portion via the at least one magnet.

A method of performing a neurovascular procedure comprising one or more of the following steps:

- providing an access catheter having an access catheter hub;
- coupling the access catheter hub to a hub adapter, movably carried by a support table;
- driving the access catheter in response to movement of the hub adapter along the table until the access catheter is positioned to achieve supra-aortic vessel access;
- removing the access catheter and access catheter hub from the hub adapter; and
- coupling a procedure catheter hub having a procedure catheter to the hub adapter.

A method as described in any embodiment herein, further comprising advancing the procedure catheter hub to position a distal end of the procedure catheter at a neurovascular treatment site.

A method as described in any embodiment herein, wherein the driving the access catheter step comprises driving the access catheter distally through a guide catheter.

A method as described in any embodiment herein, wherein the driving the access catheter step includes the step of laterally deflecting a distal region of the access catheter to achieve supra-aortic vessel access.

A method as described in any embodiment herein, wherein the coupling step comprises magnetically coupling the access catheter hub to the hub adapter.

A method as described in any embodiment herein, wherein the access catheter hub and the hub adapter are separated by a sterile field barrier.

A method as described in any embodiment herein, further comprising coupling a guide catheter hub to a guide catheter adapter through the sterile barrier.

A method as described in any embodiment herein, further comprising coupling a guidewire hub to a guidewire adapter through the sterile barrier.

A method as described in any embodiment herein, further comprising axially moving a guidewire attached to the guidewire hub in response to axially moving the guidewire adapter.

A method as described in any embodiment herein, further comprising rotating the guidewire relative to the guidewire hub.

A method as described in any embodiment herein, wherein the procedure catheter comprises an aspiration catheter.

A method as described in any embodiment herein, further comprising the step of aspirating a clot.

A method as described in any embodiment herein, further comprising driving the access catheter in response to movement of the hub adapter along the table until the access catheter achieves supra-aortic vessel access.

A method as described in any embodiment herein, further comprising maintaining supra-aortic vessel access while removing the access catheter.

A method as described in any embodiment herein, further comprising maintaining supra-aortic vessel access while coupling a procedure catheter hub.

A method as described in any embodiment herein, wherein the coupling step comprises coupling at least a first magnet on the access catheter hub to a second magnet on the hub adapter to form a magnetic coupling.

A method as described in any embodiment herein, further comprising the step of measuring elastic force across the magnetic coupling.

A method as described in any embodiment herein, further comprising the step of determining force applied to the access catheter.

A method as described in any embodiment herein, wherein the determination of force is accomplished using an optical fiber embedded in a side wall of the catheter.

A method as described in any embodiment herein, further comprising the step of determining the location of the hub adapter relative to the table.

A method of performing a neurovascular procedure, comprising one or more of the following steps:

providing an access assembly comprising a guidewire, access catheter and guide catheter;

coupling the access assembly to a robotic drive system;

driving the access assembly to achieve supra-aortic vessel access;

decoupling the guide wire and the access catheter from the access assembly;

providing a procedure assembly comprising at least a guidewire and a procedure catheter;

coupling the procedure assembly to the robotic drive system; and performing a neurovascular procedure using the procedure assembly.

A method as described in any embodiment herein, wherein the coupling the access assembly comprises magnetically coupling a hub on each of the guidewire, access catheter and guide catheter, to separate corresponding drive magnets independently movably carried by a drive table.

A method as described in any embodiment herein, wherein the coupling the access assembly to a robotic drive system is accomplished without direct contact between the access assembly and the robotic drive system.

A method as described in any embodiment herein, wherein the procedure assembly comprises a first procedure catheter and a second procedure catheter.

A method as described in any embodiment herein, wherein the guidewire and first procedure catheter are positioned concentrically within the second procedure catheter.

A method as described in any embodiment herein, wherein the procedure assembly is advanced as a unit through at least a portion of the length of the guide catheter.

A method as described in any embodiment herein, wherein the procedure comprises a neurovascular thrombectomy.

A method as described in any embodiment herein, comprising axially advancing or retracting the guidewire.

A method as described in any embodiment herein, comprising rotating the guidewire with respect to a guidewire hub.

A method as described in any embodiment herein, comprising axially advancing or retracting the access catheter.

A method as described in any embodiment herein, comprising rotating the access catheter with respect to an access catheter hub.

A method as described in any embodiment herein, comprising laterally deflecting a deflection zone on the access catheter.

A method as described in any embodiment herein, wherein the hub on each of the guidewire, access catheter and guide catheter are separated from the corresponding drive magnets by a sterile field barrier.

A method as described in any embodiment herein, wherein driving the access assembly comprises rolling the hub on each of the guidewire, access catheter and guide catheter along the sterile field barrier in response to movement of the drive magnets.

A method as described in any embodiment herein, further comprising maintaining supra-aortic vessel access while decoupling at least one of the guide wire and the access catheter from the access assembly.

A method as described in any embodiment herein, further comprising maintaining supra-aortic vessel access while coupling the procedure assembly.

A method as described in any embodiment herein, further comprising determining relative movement between a magnet in a hub and a corresponding magnet carried by the drive table.

A method as described in any embodiment herein, further comprising determining the location of the hub relative to the drive table.

A method as described in any embodiment herein, further comprising determining axial force applied to the access catheter.

A method as described in any embodiment herein, further comprising determining rotational torque applied to the access catheter.

What is claimed is:

1. A sterile assembly for a robotic medical procedure, comprising:

a sterile barrier having a first support surface and a second support surface oriented along a plane non-parallel to the first support surface, wherein the first support surface and the second support surface extend from a proximal end of the sterile barrier to a distal end of the sterile barrier, and are configured to separate a sterile field from a non-sterile field; and at least a first interventional device within the sterile field, the first interventional device including a hub and an elongate flexible body, the hub including at least one magnet facing the sterile barrier and at least one surface contact between the hub and the second support surface, wherein the hub is configured to advance along the second support surface between the proximal end of the sterile barrier and the distal end of the sterile barrier.

2. A sterile assembly as in claim 1, wherein the sterile barrier is configured to reside on a support table adjacent a patient, with the second support surface within the sterile field.

3. A sterile assembly as in claim 2, wherein the second support surface is substantially horizontal when residing on the support table.

4. A sterile assembly as in claim 2, wherein the first support surface is inclined relative to a horizontal plane when residing on the support table.

5. A sterile assembly as in claim 2, wherein the sterile barrier comprises an elongate polymeric membrane having a longitudinal axis.

6. A sterile assembly as in claim 1, wherein the hub further comprises at least one fluid injection port.

7. A sterile assembly as in claim 1, wherein the hub further comprises a wireless RF transceiver.

8. A sterile assembly as in claim 1, further comprising a visual indicator on the hub, for indicating a presence of a clot.

9. A sterile assembly as in claim 8, wherein the visual indicator comprises a clot collection chamber having a transparent window.

10. A sterile assembly as in claim 9, further comprising a filter in the clot collection chamber.

11. A sterile assembly as in claim 1, further comprising a sensor for detecting a presence of a clot.

12. A sterile assembly as in claim 11, wherein the sensor comprises a pressure sensor.

13. A sterile assembly as in claim 11, wherein the sensor comprises an optical sensor.

14. A sterile assembly as in claim 1, further comprising a channel, wherein the first interventional device is contained along the channel, the channel comprising the first support surface.

15. A sterile assembly as in claim 1, wherein the first interventional device is a guide catheter.

16. A sterile assembly as in claim 1, wherein the first interventional device is an access catheter.

17. A sterile assembly as in claim 1, wherein the first interventional device is a guidewire.

18. A sterile assembly as in claim 1, wherein the first interventional device is an aspiration catheter.

19. A sterile assembly as in claim 1, comprising a supra-aortic vessel access assembly.

20. A sterile assembly as in claim 19, wherein the access assembly comprises a guidewire, an access catheter and a guide catheter.

21. A sterile assembly as in claim 20, further comprising a procedure assembly within the sterile field.

22. A sterile assembly as in claim 21, wherein the procedure assembly comprises a second guidewire and an aspiration catheter.

23. A sterile assembly as in claim 1, wherein the sterile barrier is magnetically permeable.

24. A sterile assembly as in claim 1, wherein the sterile barrier is fluid impermeable.

25. A sterile assembly as in claim 1, wherein the sterile barrier is radiofrequency permeable.

26. A sterile assembly as in claim 1, wherein the sterile barrier is impermeable to microorganisms.

27. A sterile assembly as in claim 1, wherein the sterile barrier is translucent.

28. A sterile assembly as in claim 1, wherein the sterile barrier is transparent.

29. A sterile assembly as in claim 1, wherein the second support surface has a convex curvature such that fluid is configured to flow away from the second support surface.

30. A sterile assembly as in claim 29, wherein the second support surface has a longitudinal axis and a transverse axis and the second support surface is convex in a direction in the transverse axis.

31. A sterile assembly as in claim 1, wherein the sterile barrier is contained within an outer packaging.

32. A sterile assembly as in claim 1, wherein the sterile barrier comprises a non-compliant polymer.

33. A sterile assembly as in claim 32, wherein the non-compliant polymer comprises Polyethylene terephthalate (PET) or a thermoplastic polyurethane.

34. A sterile assembly as in claim 1, wherein the sterile barrier further comprises a removable cover portion that cooperates with the second support surface to define a sterile volume.

35. A sterile assembly as in claim 1, wherein the hub is releasably coupled to the second support surface via the at least one magnet.

36. A sterile assembly as in claim 1, wherein the sterile barrier further comprises a third support surface oriented along a plane non-parallel to the second support surface, wherein the third support surface extends from the proximal end of the sterile barrier to the distal end of the sterile barrier.

37. A sterile assembly as in claim 1, wherein the first support surface is configured to support at least a portion of the hub.

38. A sterile assembly as in claim 1, wherein the sterile barrier comprises a channel, the channel comprising the first support surface.

39. A sterile assembly as in claim 1, further comprising at least a second interventional device within the sterile field, the second interventional device including a hub and an elongate flexible body, the hub of the second interventional device including at least one magnet facing the sterile barrier and at least one surface contact between the hub and the second support surface, wherein the hub is configured to advance along the second support surface between the proximal end of the sterile barrier and the distal end of the sterile barrier.

40. A sterile assembly as in claim 39, wherein the elongate flexible body of the second interventional device is configured to be received within a lumen of the elongate flexible body of the first interventional device.

* * * * *